(12) United States Patent
Brünn

(10) Patent No.: US 12,275,782 B2
(45) Date of Patent: *Apr. 15, 2025

(54) MEANS AND METHODS FOR THE DETERMINATION OF THE BIOLOGICAL ACTIVITY OF NEUROTOXIN POLYPEPTIDES IN CELLS

(71) Applicant: MERZ PHARMA Gmbh & CO. KGaA, Frankfurt am Main (DE)

(72) Inventor: Cornelia Brünn, Frankfurt am Main (DE)

(73) Assignee: MERZ PHARMA GmbH & CO. KGaA, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/621,418

(22) Filed: Mar. 29, 2024

(65) Prior Publication Data
US 2024/0270833 A1 Aug. 15, 2024

Related U.S. Application Data

(62) Division of application No. 14/901,123, filed as application No. PCT/EP2014/063531 on Jun. 26, 2014, now Pat. No. 11,976,110.

(30) Foreign Application Priority Data

Jun. 28, 2013 (EP) ..................................... 13174176

(51) Int. Cl.
| | |
|---|---|
| G01N 33/53 | (2006.01) |
| C07K 16/18 | (2006.01) |
| G01N 21/64 | (2006.01) |
| G01N 33/50 | (2006.01) |

(52) U.S. Cl.
CPC ......... *C07K 16/18* (2013.01); *G01N 21/6428* (2013.01); *G01N 33/5014* (2013.01); *G01N 33/5058* (2013.01); *G01N 33/5073* (2013.01); *C07K 2317/34* (2013.01); *G01N 2021/6441* (2013.01); *G01N 2333/33* (2013.01); *G01N 2333/952* (2013.01)

(58) Field of Classification Search
CPC .............. C07K 16/18; C07K 2317/34; G01N 21/6428; G01N 33/5014; G01N 33/5058; G01N 33/5073; G01N 2021/6441; G01N 2333/33; G01N 2333/952
See application file for complete search history.

(56) References Cited

U.S. PATENT DOCUMENTS

| | | |
|---|---|---|
| 7,229,605 B2 | 6/2007 | Holland et al. |
| 8,198,034 B2 | 5/2012 | Fernandez-Salas |
| 8,420,352 B2 | 4/2013 | Oyler |
| 8,609,413 B2 | 12/2013 | Suter |
| 8,778,623 B2 | 7/2014 | Johnson |
| 9,102,901 B2 | 8/2015 | Wang |
| 9,217,172 B2 | 12/2015 | Johnson |
| 9,579,362 B2 | 2/2017 | Nevalaita |
| 10,725,025 B2 | 7/2020 | Jatzke |
| 2003/0032891 A1 | 2/2003 | Jenkins |
| 2006/0099672 A1 | 5/2006 | Dolly |
| 2008/0032931 A1 | 2/2008 | Steward |

(Continued)

FOREIGN PATENT DOCUMENTS

| | | |
|---|---|---|
| EP | 1597584 | 2/2004 |
| EP | 2015065 | 4/2006 |

(Continued)

OTHER PUBLICATIONS

Armbruster, David, A., et al., "Limit of Blank, Limit of Detection and Limit of Quantitation", Clin. Biochem. Rev., vol. 29, Suppl (i), Aug. 2008, pp. s49-s52.

Arnon, Stephen, S., et al., "Botulinum toxin as a biological weapon, medical and public health management", JAMA, vol. 285, No. 8, Feb. 2

(56) References Cited

U.S. PATENT DOCUMENTS

| | | |
|---|---|---|
| 2010/0167286 A1 | 7/2010 | Reijo Pera |
| 2010/0216181 A1 | 8/2010 | Daigh |
| 2010/0233802 A1 | 9/2010 | Zhu |
| 2010/0279403 A1 | 11/2010 | Rajesh |
| 2011/0008397 A1 | 1/2011 | Cohen |
| 2011/0046092 A1 | 2/2011 | Suter |
| 2011/0053244 A1 | 3/2011 | Oyler |
| 2012/0122128 A1 | 5/2012 | Fernandez-Salas |
| 2012/0276063 A1 | 11/2012 | Meyer |
| 2012/0282647 A1 | 11/2012 | Mander |
| 2014/0248644 A1 | 9/2014 | Wang |
| 2015/0044709 A1 | 2/2015 | Eisele |
| 2016/0289731 A1 | 10/2016 | Eisele |
| 2017/0059558 A1 | 3/2017 | Eisele |
| 2018/0045733 A1 | 2/2018 | Eisele |
| 2018/0238861 A1 | 8/2018 | Jatzke |
| 2019/0023771 A1 | 1/2019 | Bruenn |

FOREIGN PATENT DOCUMENTS

| | | |
|---|---|---|
| EP | 1926744 | 6/2008 |
| GB | 2398636 | 8/2004 |
| GB | 2416849 | 2/2006 |
| WO | WO 9533850 | 12/1995 |
| WO | WO2004031773 | 4/2004 |
| WO | WO2005007185 | 1/2005 |
| WO | WO 2005/076785 | 8/2005 |
| WO | WO2006020208 | 2/2006 |
| WO | WO 2009/114748 | 9/2009 |
| WO | WO2010099539 | 9/2010 |
| WO | WO2010105234 | 9/2010 |
| WO | WO2011022438 | 2/2011 |
| WO | WO2011025852 | 3/2011 |
| WO | WO2011047265 | 4/2011 |
| WO | WO2011056971 | 5/2011 |
| WO | WO 2012123370 | 9/2012 |
| WO | WO2012135621 | 10/2012 |
| WO | WO2014079878 | 5/2014 |

OTHER PUBLICATIONS

Baldwin, Michael, R., et al., "Association of Botulinum neurotoxin serotypes A and B with synaptic vesicle protein complexes", Biochemistry, 46, 2007, pp. 3200-3210.
Barash and Arnon, J. Infect. Dis., (2014), vol. 209, No. 2, pp. 183-191.
Berntsson, Ronnie P.A. et al, Structure of dual receptor binding to botulinum neurotoxin B, Nature Communication, 2013, vol. 4(2058), pp. 1-13.
Boroff, Daniel., A., et al., Journal of Bacteriology, No. 1966, vol. 92, No. 5, p. 1580-1581, "Statistical analysis of a rapid in vivo method for the titration of the toxin of Clostridium botulinum".
Cai, Shuowei, et al., "Botulism diagnostics: from clinical symptoms to in vitro assays", Critical Reviews in Microbiology, 33, 2007, pp. 109-125.
Chang et al., Naunyn-Schmiedeberg's Arch. Pharmacol. vol. 282, p. 129-142 (1974).
Corada, Monica, et al., "Monoclonal antibodies directed to different regions of vascular endothelial cadherin extracellular domain affect adhesion and clustering of the protein and modulate endothelial permeability", Blood, vol. 97, No. 6, Mar. 15, 2001, pp. 1679-1684.
Couesnon, Aurélie, et al., "Expression of botulinum neurotoxins A and E, and associated non-toxin genes, during the transition phase and stability at high temperature: analysis by quantitative reverse transcription-PCR", Microbiology, 152, 20-06, pp. 759-770.
Creative Diagnostics; Product Literature for Anti-SNAP-25 monoclonal antibody, clone. C318M (DMAB4345), pp. 1-2; Retreived from the Internet on Jul. 28, 2020.
Dover, N. et al., J Infect Dis, (2014), vol. 209, No. 2, pp. 192-202.
Dressler, Dirk, et al., "Mouse diaphragm assay for detection of antibodies against botulinum toxin type B", Movement Disorders, vol. 20, No. 12, 2005, pp. 1617-1619.

Ekong, Theresa, A., et al., Microbiology, 1997, vol. 143, pp. 3337-3347, "Recombinanat SNAP-25 is an effective substrate for Clostridium botulinum type A toxin endopeptidase activity in vitro".
Ellies, M., (English translation) Laryngo-Rhino-Otol, 2003, vol. 82, pp. 713-714, "Tierexperimentelle und klinische untersuchungen zur sekretionshemmung der kopfspeicheldrüsen durch botulinum toxin A".
Ellies, M., Laryngo-Rhino-otol, 2003, vol. 82, pp. 713-714, "Tierexperimentelle und klinische untersuchungen zur sekretionshemmung der kopfspeicheldrüsen durch botulinum toxin A".
Evans, E.R., et al., Journal of Applied Microbiology, 2009, vol. 107, pp. 1384-1391, "An assay for botulinum toxin types A, B and F that requires both functional binding and catalytic activities within the neurotoxin".
Fan, Frank, et al., Assay and Drug Development Technologies, vol. 5, No. 1, 2007, pp. 127-136, "Bioluminescent assays for high-troughput screening".
Fernandez-Salas, Ester, et al., "Botulinum neurotoxin serotype a specific cell-based potency assay to replace the mouse bioassay", PLoS One, vol. 7, Iss. 11, Nov. 2012, e49516, pp. 1-13.
Fischer, Audrey, et al., "Single molecule detection of intermediates during botulinum neurotoxin translocation across membranes", PNAS, vol. 104, No. 25, Jun. 19, 2007, pp. 10447-10452.
Funakoshi Product Catalog, "Kit for semiquantifying two proteins on cultured cells". Published Mar. 2, 2009.
Gee, Kyle, R., et al., "Fluorogenic substrates based on fluorinated umbelliferones for continuous assays of phosphatases and β-galactosidases", Analytical Biochemistry, vol. 273, Iss. 1, Aug. 1999, pp. 41-48.
Göschel et al., Exp. Neurol., vol. 147, p. 1, 1997.
Gossen, Manfred, et al., Proc. Natl. Acad. Sci. USA, Jun. 1992, vol. 89, pp. 5547-5551, "Tight control of gene expression in mammalian cells by tetracycline-responsive promoters".
Habermann, E., Naunyn-Schmiedeberg's Arch. Pharmacol., 1974, vol. 281, pp. 47-56, "I-labeled neurotoxin from Clostridium botulinum A: preparation, binding to synaptosomes and ascent to the spinal cord".
Hemmerlein, Bernhard, et al., "Overexpression of Eag1 potassium channels in clinical tumours", Molecular Cancer, 5:41, 2006, pp. 1-13.
Hester, Mark E. et al, Molecular Therapy, vol. 19(10) pp. 1905-1912, Oct. 2011.
Hill et al., J Bacteriol., (2007), vol. 189, No. 3, pp. 818-832.
Hughes, R., et al., J. Physiol. 1962, vol. 160, pp. 221-233, "Influence of nerve-ending activity and of drugs on the rate of paralysis of rat diaphragm preparations by CL. botulinum type A toxin".
International Preliminary Report on Patentability for PCT/EP2013/074276 dated Jun. 4, 2015.
International Search Report With Written Opinion for PCT/EP2010/006967 of Jan. 24, 2011.
International Search Report and Written Opinion for PCT/US2012/057825 of Nov. 8, 2012.
International Search Report for PCT/EP2013/074276 of Feb. 13, 2014.
International Search Report in International Application No. PCT/EP2015/053403, dated Apr. 17, 2015.
Jacky, Birgitte P.S. et al, PLOS Pathogens, May 2013, vol. 9(5)e1003369, pp. 1-17, Identification of fibroblast growth factor receptor 3 (FGFR3) as a protein receptor for botulinum neurotoxin serotype A (BoNT/A).
James et al., Am. J. Physiol. Gastrointest. Liver Physiol. vol. 285, p. G291-G297 (2003).
Jamieson, et al. "Development and validation of cell-based ELISA for the quantification of trastuzumab in human plasma", Journal of Immunological Methods, 345:106-111, 2009.
Jones; R.G.A, et al., "Development of improved SNAP25 endopeptidase immuno-assays for botulinum type A and E toxins", Journal of Immunological Methods 329, 2008, pp. 92-101.
Jost, Wolfgang, H., et al., "Botulinum neurotoxin type A free of complexing proteins (Xeomin) in focal dystonia", Drugs, 67(5), 2007, pp. 669-683.
Karumbayaram, et al., Stem Cells, vol. 27, No. 4, p. 806-811, 2009.

(56) References Cited

OTHER PUBLICATIONS

Keller J., et al., Biochemistry, vol. 43, No. 2, p. 526-532, Jan. 20, 2004.
Keller, J.E., "Recovery from botulinum neurotoxin poisoning in vivo", Neuroscience, 139, 2006, pp. 629-637.
Keller, James E., et al., FEBS Letters 456, 1999, pp. 137-142, "Persistence of botulinum neurotoxin action in cultured spinal cord cells".
Kiris, et al., Stem Cell Res., vol. 6, No. 3, p. 195-205, May 2011.
Kondo, Hisashi, et al., Japan. J. Med. Sci. Biol., 1984, vol. 37, pp. 131-135, "Titration of botulinum toxins for lethal toxicity by intravenous injection into mice".
Krieglstein, Kerstin, et al., "Arrangement of disulfide bridges and positions of sulfhydryl groups in tetanus toxin", Eur. J. Biochem., 188, 1990, pp. 39-45.
Krieglstein, Kerstin, G., et al., "Covalent structure of botulinum neurotoxin type A: location of sulfhydryl groups, and disulfide bridges and identification of C-termini of light and heavy chains", Journal of Protein Chemistry, vol. 13, No. 1, 1994, pp. 49-57.
Krieglstein, Kerstin, G., et al., "Limited proteolysis of tetanus toxin", Eur. J. Biochem, 202, 1991, pp. 41-51.
Kroken, et al. J. Biolog. Chem., (2011), vol. 286, No. 30, 26828-26837.
Lamanna, Carl, et al., Infection and Immunity, Apr. 1970, vol. 1, No. 4, pp. 423-424 "Dependence of time to death on molecular size of botulinum toxin".
Malizio, Carl J., et al., Methods in Molecular Biology, 2000, vol. 145: Bactrial Toxins: methods and Protocols, pp. 27-39, "Purification of Clostridium botulinum type A neurotoxin".
McNutt, et al., Cell Based Assay for Neurotoxins, Chapter 12, pp. 247-271, Springer Science+Business Media Dordrecht, 2015, P. Gopalakrishnakone et al (eds) Biological Toxins and Bioterrorism, Toxicology.
McNutt, Patrick, et al, Biochemical and Biophysical Research Communications, 2011, vol. 405, pp. 85-90.
Meng, Yuan, et al., "Enhanced sensitivity and precision in an enzyme-linked immunosorbent assay with fluorogenic substrates compared with commonly used chromogenic substrates", Analytical Biochemistry, 345, 2005, pp. 227-236.
Miraglia, Loren, J., et al., Combinatorial Chemistry & High Throughtput Screening, 2011, vol. 14, pp. 648-657 "Seeing the light: luminescent reporter gene assays".
Monnier, G., et al., (English Translation) Readapt. Med. Phys. 2003, vol. 46, pp. 338-345 "Hypersialorrhée, hypersudation et toxine botulique sialorrhea, hyperhidrosis and botulinum toxin".
Monnier, G., et al., Readapt. Med. Phys. 2003, vol. 46, pp. 338-345 "Hypersialorrhée, hypersudation et toxine botulique sialorrhea, hyperhidrosis and botulinum toxin".
Needleman, Saul, B., et al., "A general method applicable to the search for similarities in the amino acid sequence of two proteins", J. Mol. Biol., 48, 1970, pp. 443-453.
Nuss, et al. "Botulinum Neurotoxin Serotype A Cleavage-Sensitive Antibodies", Journal of Biomolecular Screening, 15(1):42-52, 2-10.
Padlan, Eduardo, A., "X-ray crystallography of antibodies", Advances in Protein Chemistry, vol. 49, 1996, pp. 57-133.
Pearce L. Bruce, et al., Toxicon Elmsford, vol. 35, No. 9, p. 1373-1412, Sep. 1, 1997.
Pearce, L. Bruce, et al., "Measurement of botulinum toxin activity: evaluation of the lethality assay", Toxicology and Applied Pharmacology, 128, 1994, pp. 69-77.
Pellet, Sabine, et al., "Sensitive and quantitative detection of botulinum neurotoxin in neurons derived from mouse embryonic stem cells", Biochem. Biophys. Res. Commun., 404(1), Jan. 7, 2011, pp. 388-392.
Pellett, et al., FEBS Lett., vol. 581, No. 25, p. 4803-4808, 2007.
Pellett, et al., Journal of Pharmacological and Toxicological Methods, vol. 61, No. 3, p. 304-310, May 1, 2010.
Pellett, Sabina, Curr. Top. Microbiol. Immunol., 2013, 364:257-285.
Pellizzari, R., et al., Toxicology Letters, vol. 102-103, p. 191-197, Dec. 28, 1998.
Purkiss, et al. Clostridium botulinum Neurotoxins Act with a Wide Range of Potencies on SH-SY5Y Human Neuroblastoma Cells. NeuroToxicology 22:447-453, 2001.
R&D Systems Product Catalog, "Cell-Based ELISA", published 2007.
Rassetti-Escargueil C., et al, Journal of the International Society on Toxinology Apr. vol. 53, No. 5, p. 503-511, Apr. 2009.
Research and Diagnostic Antibodies catalog, 2005 (retrieved from http://www.rdabs.com/files/Antibodies/Monoclonal%20Abs.pdf).
Rheaume, et al. "A Highly Specific Monoclonal Antibody for Botulinum Neurotoxin Type A-Cleaved SNAP25" Toxins, 7:2354-2370, 2015.
Sawyer, Peptide Based Drug Design, ACS, (1995), pp. 378-422.
Schiavo, Giampietro, et al., Physiological Reviews, Apr. 2000, vol. 80, No. 2, pp. 717-765 "Neurotoxins. affecting neuroexocytosis".
Schokett, Penny, et al., Current Protocols in Molecular Biology 1997, Suppl. 60, pp. 16.14.1-16.14.9 "Inducible gene expression using an autoregulatory, tetracycline-controlled system".
Sheridan, R.E., et al, Applied Toxicology, vol. 19, Suppl. 1, p. S29-S33, Dec. 1999.
Sigma Catalog, 2006 (retrieved from web Jun. 19, 2020).
Silberstein, Stephen, "Botulinum neurotoxins: origins and basic mechanisms of action", Pain Practice, vol. 4, Iss. 1S, 2004, pp. S19-S26.
Staughan, Donald, W., "Progress in applying the three Rs to the potency testing of botulinum toxin type A", ATLA, 34, 2006, pp. 305-313.
Takahashi, K et al, Cell, vol. 131, Nov. 30, 2007, pp. 861-872, Induction of pluripotent stem cells from adult human fibroblasts by defined factors.
Tuuminen, Tamara, et al., "3-p-hydroxyphenylpropionic acid—a sensitive fluorogenic substrate for automated fluorometric enzyme immunoassays", Journal of Immunoassay, 12:1, 1991, pp. 29-46.
Vertiev, et al., "Effective expression of fragments of a botulinum neurotoxin type A gene, coding for the L-chain and H-chain in *E. coli*, with formation of products causing protective immunity to administration of the toxin", Mol Gen Mikrobiol Virusol. vol. 4, 2000, pp. 3-7.
Vlaev, et al. Appl Microbiol. Biotechnol., 2013, 97:5303-5313.
Whitemarsh, Regina, C.M., "Novel application of human neurons derived from induced pluripotent stem cells for highly sensitive botulinum neurotoxin detection", Toxicological Sciences, 126(2), 2012, pp. 426-435.
Williamson. L.C., et al., Journal of Biological Chemistry, American Society for Biochemisty and Molecular Biology, vol. 271, No. 13, p. 7694-7699, Mar. 29, 1996.
Wohlfarth, K., et al., Naunyn-Schmiedebergs Archives of Pharmacology, vol. 355, No. 3, p. 335-340, Mar. 1997.
Yang, et al. "Development of a quantitative cell-based ELISA, for a humanized anti-IL-2/IL-15 receptor β antibody (HuMikβ1), and correlation with functional activity using an antigen-transfected murine cell line", Journal of Immunological Methods, 311:71-80, 2006.
Yowler, et al. J. Biolog. Chem., 2002, vol. 277, pp. 32815-32819.
Yu, Junying, et al. , "Human induced pluripotent stem cells free of vector and transgene sequences", Science, 324(5928), May 8, 2009, pp. 797-801.
Zhu, et al. Cell & Developmental Biology, vol. 13, pp. 121-128, 2002.
Stahl, Journal of Biomolecular Screening, 12:370-377, 2007.

MEANS AND METHODS FOR THE DETERMINATION OF THE BIOLOGICAL ACTIVITY OF NEUROTOXIN POLYPEPTIDES IN CELLS

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 111,572 Bytes file named "MERZ_210_SEQ_US_DIV_SEQUENCE_LISTING.XML," created on 22 Mar. 2024.

The present invention pertains to a method for directly determining the biological activity of a Neurotoxin polypeptide in cells, comprising the steps of: a) incubating cells susceptible to Neurotoxin intoxication with a Neurotoxin polypeptide for a time and under conditions which allow for the Neurotoxin polypeptide to exert its biological activity; b) fixing the cells and, optionally, permeabilizing the cells with a detergent; c) contacting the cells with at least a first capture antibody specifically binding to the non-cleaved and Neurotoxin-cleaved substrate and with at least a second capture antibody specifically binding to the cleavage site of the Neurotoxin-cleaved substrate, under conditions which allow for binding of said capture antibodies to said substrates; d) contacting the cells with at least a first detection antibody specifically binding to the first capture antibody, under conditions which allow for binding of said first detection antibody to said first capture antibody, thus forming first detection complexes, and at least a second detection antibody specifically binding to the second capture antibody, under conditions which allow for binding of said second detection antibody to said second capture antibody, thus forming second detection complexes; e) determining the amount of the first and second detection complexes of step d), and f) calculating the amount of substrate cleaved by said Neurotoxin polypeptide in said cells by means of the second detection complexes, thereby determining the biological activity of said Neurotoxin polypeptide in said cells. The invention further provides for a kit for carrying out the method of the invention.

*Clostridium botulinum* and *Clostridium tetani* produce highly potent Neurotoxins, i.e. Botulinum toxins (BoNTs) and Tetanus toxin (TeNT), respectively. These Clostridial Neurotoxins (CNTs) specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by the bacterial protease(s). Active Neurotoxin consists of two chains, an N-terminal light chain of approx. 50 kDa and a heavy chain of approx. 100 kDa linked by a disulfide bond. CNTs structurally and functionally consist of three domains, i.e. the catalytic light chain, the heavy chain encompassing the translocation domain (N-terminal half) and the receptor binding domain (C-terminal half); see, e.g., Krieglstein 1990, Eur. J. Biochem. 188, 39; Krieglstein 1991, Eur. J. Biochem. 202, 41; Krieglstein 1994, J. Protein Chem. 13, 49. The Botulinum Neurotoxins are synthesized as molecular complexes comprising the 150 kDa Neurotoxin protein and associated non-toxic proteins. The complex sizes differ based on the Clostridial strain and the distinct Neurotoxin serotypes ranging from 300 kDa, over 500 kDa, and 900 kDa. The non-toxic proteins in these complexes stabilize the Neurotoxin and protect it against degradation; see Silberstein 2004, Pain Practice 4, S19-S26.

*Clostridium botulinum* secretes seven antigenically distinct serotypes designated A to G of the Botulinum Neurotoxin (BoNT). All serotypes together with the related Tetanus Neurotoxin (TeNT) secreted by *Clostridium tetani*, are $Zn^{2+}$-endoproteases that block synaptic exocytosis by cleaving SNARE proteins; see Couesnon, 2006, Microbiology, 152, 759. CNTs cause the flaccid muscular paralysis seen in botulism and tetanus; see Fischer 2007, PNAS 104, 10447.

Despite its toxic effects, Botulinum toxin complex has been used as a therapeutic agent in a large number of diseases. Botulinum toxin serotype A was approved for human use in the United States in 1989 for the treatment of strabism, blepharospasm, and other disorders. It is commercially available as Botulinum toxin A (BoNT/A) protein preparation, for example, under the trade name BOTOX (Allergan, Inc.) or under the trade name DYSPORT/RELOXIN (Ipsen, Ltd). An improved, complex-free Botulinum toxin A preparation is commercially available under the trade name XEOMIN (Merz Pharmaceuticals, LLC). For therapeutic applications, the preparation is injected directly into the muscle to be treated. At physiological pH, the toxin is released from the protein complex and the desired pharmacological effect takes place. The effect of Botulinum toxin is only temporary, which is the reason why repeated administration of Botulinum toxin may be required to maintain a therapeutic affect.

The Clostridial Neurotoxins weaken voluntary muscle strength and are effective therapy for strabism, focal dystonia, including cervical dystonia, and benign essential blepharospasm. They have been further shown to relief hemifacial spasm, and focal spasticity, and moreover, to be effective in a wide range of other indications, such as gastrointestinal disorders, hyperhidrosis, and cosmetic wrinkle correction; see Jost 2007, Drugs 67, 669.

During the manufacturing process of Clostridial Neurotoxins, the qualitative and quantitative determination of said Neurotoxins as well as the quality control of the biologically active Neurotoxin polypeptides is of particular importance. In addition, governmental agencies accept only simple, reliable, and validated Botulinum toxin activity assays. At present the mouse $LD_{50}$ bioassay, a lethality test, remains the "gold standard" used by pharmaceutical manufacturers to analyze the potency of their preparations; see Arnon et al. (2001), JAMA 285, 1059-1070. However, in recent years, considerable effort has been undertaken to seek for alternative approaches to alleviate the need for animal testing and all the disadvantages, costs and ethical concerns associated with this type of animal-based assays. In addition, the regulatory agencies are engaging pharmaceutical companies to apply the three "Rs" principle to the potency testing of Botulinum Neurotoxins: "Reduce, Refine, Replace": see Straughan, Altern. Lab. Anim. (2006), 34, 305-313. As a consequence, cell-based test systems have been developed in order to provide reasonable alternatives to methods using live animals. Yet, only three cellular test systems are available for the determination of Neurotoxin biological activity thus far which have been shown to be sufficiently sensitive to Neurotoxin polypeptides. These cell-based test systems include the use of primary neurons isolated from rodent embryos which are differentiated in vitro (Pellett et al. (2011), Biochem. Biophys. Res. Commun. 404, 388-392), neuronal differentiated induced pluripotent stem cells (Whitemarsh et al. (2012), Toxicol. Sci. 126, 426-35), and a subclone of the SiMa cell line (WO 2010/105234 A1).

However, the isolation of primary neurons requires the killing of animals and is laborious and time consuming. Further, test systems using different primary neurons show large variances. Similarly, the generation of neuronal differentiated induced pluripotent stem cells is difficult and time consuming. In addition, storage of such cells is very problematic. Assays using tumor cell lines are frequently not sensitive enough to BoNT. Moreover, complex differentiation protocols are required for said tumor cell lines which result in large variances and/or high failure rates of assays using said cell lines.

Assays for determining the biological activity of Clostridial Neurotoxins described in the art include Western blot analysis in which the Neurotoxin activity is quantified by the amount of cleaved Neurotoxin substrate in cell lysates. In other assays, the activity of Clostridial Neurotoxins is measured by an electrochemiluminescence (ECL) sandwich ELISA; see WO 2009/114748 A1. Also in this case, the biological activity of the Clostridial Neurotoxin is determined by the detection of cleaved Clostridial Neurotoxin substrate after isolation from the cell lysate. Further, the Neurotoxin substrate has to be concentrated, in both assays.

In light of the above, further test systems for the determination of Neurotoxin polypeptide activity acceptable to governmental agencies and/or providing for an alternative to animal-based test systems are highly desirable.

Thus, the technical problem underlying the present invention may be seen as the provision of means and methods complying with the aforementioned needs. The technical problem is solved by the embodiments characterized in the claims and herein below.

The present invention relates, in a first aspect, to a method for directly determining the biological activity of a Neurotoxin polypeptide in cells, comprising the steps of:
a) incubating cells susceptible to Neurotoxin intoxication with a Neurotoxin polypeptide for a time and under conditions which allow for the Neurotoxin polypeptide to exert its biological activity;
b) fixing the cells and, optionally, permeabilizing the cells with a detergent;
c) contacting the cells with at least a first capture antibody specifically binding to the non-cleaved and Neurotoxin-cleaved substrate and with at least a second capture antibody specifically binding to the cleavage site of the Neurotoxin-cleaved substrate, under conditions which allow for binding of said capture antibodies to said substrates;
d) contacting the cells with at least a first detection antibody specifically binding to the first capture antibody, under conditions which allow for binding of said first detection antibody to said first capture antibody, thus forming first detection complexes and at least a second detection antibody specifically binding to the second capture antibody, under conditions which allow for binding of said second detection antibody to said second capture antibody, thus forming second detection complexes;
e) determining the amount of the first and second detection complexes of steps d); and
f) calculating the amount of substrate cleaved by said Neurotoxin polypeptide in said cells by means of the second detection complexes, thereby determining the biological activity of said Neurotoxin polypeptide in said cells.

The method of the invention allows for the direct determination of the biological activity of a Neurotoxin polypeptide in cells. This means that no lysis of the cells and no isolation or concentration of the cleaved Neurotoxin substrate from cell lysates is necessary any longer, as in the methods described in the art. For example, in the Western blot analysis-based assay of the art, the Neurotoxin substrate is concentrated by the separation and concentration of the components of the respective sample in the SDS polyacrylamide gel. In the aforementioned ECL sandwich ELISA described in the art, the concentration of the Neurotoxin substrate is carried out by using antibodies which bind specifically to the cleaved Neurotoxin substrate on a microtiter plate to which the cell lysate is added. The cleaved Neurotoxin substrate is isolated from the lysate by binding of the mentioned antibody which results in a concentration of said cleaved Clostridial Neurotoxin substrate. In contrast, the cleaved Neurotoxin substrate, as exemplified for SNAP-25, can be directly detected in the cell, in the method of the invention. To this end, cells which are susceptible to Neurotoxin intoxication as defined in more detail elsewhere herein are incubated with a Neurotoxin polypeptide for a time and under conditions which allow for the Neurotoxin polypeptide to exert its biological activity. In a next step, the cells are fixed, for example, by addition of a fixation agent such as methanol, ethanol, acetone, formaldehyde or mixtures of the mentioned fixation agents. Optionally, the cells can be permeabilized by using at least one detergent as defined elsewhere herein such as Triton X-100, Tween 20, Saponin, Digitonin or n-Octyl-β-glucopyranoside. The detergent can be comprised in an appropriate buffer such as PBS. Thereafter, the cells are contacted with at least a first capture antibody which specifically binds to the non-cleaved and Neurotoxin-cleaved substrate and with at least a second capture antibody specifically binding to the cleavage site of the Neurotoxin-cleaved substrate, under conditions which allow for binding of said capture antibodies to said substrates. Herein, the first capture antibody is able to determine the total content or amount of Neurotoxin substrate in the cells, by binding specifically to an appropriate epitope present in both the non-cleaved and Neurotoxin-cleaved Neurotoxin substrate. The second capture antibody recognizes and binds specifically to an epitope present only in the cleaved Neurotoxin substrate, for example, by binding specifically to the Neurotoxin-cleaved site in the Neurotoxin substrate. Alternatively, the cells can be contacted with a mixture of said first and second capture antibodies, i.e. cells are contacted with at least a first capture antibody and at least a second capture antibody simultaneously, under the mentioned conditions. In the next step, the cells are contacted with at least a first detection antibody specifically binding to the first capture antibody under conditions which allow for binding of said first detection antibody to said first capture antibody, thus forming first detection complexes. In a subsequent step, the cells are contacted with at least a second detection antibody specifically binding to the second capture antibody, under conditions which allow for binding of said second detection antibody to said second capture antibody, thus forming second detection complexes.

Alternatively, the cells can be contacted with a mixture of said first and second detection antibodies, i.e. the cells are contacted with at least a first detection antibody and at least a second detection antibody simultaneously, under the mentioned conditions. Alternatively, after permeabilization of the cells, they can be contacted with a mixture of said first and second capture antibodies and said first and second detection antibodies simultaneously, under the mentioned conditions. In the next step, the amounts of the first and second detection complexes are determined. Finally, the amount of substrate cleaved by said Neurotoxin polypeptide in said cells is calculated by means of the second detection complexes. Thereby, the biological activity of said Neurotoxin polypeptide is determined directly in the cells.

In the following, the method of the invention is described in more detail. For cell culture, the cells susceptible to Neurotoxin intoxication as defined herein, such as neuronal cells, SiMa cells or iPS-derived neurons, are first seeded on 96 well microtiter plates. SiMa cells are differentiated to a neuronal phenotype, for example, according to the procedures disclosed in WO 2010/105234, and iPS-derived neurons are differentiated to a neuronal phenotype, e.g., according to assays described in WO 2012/135621. Then, the cells are intoxicated with a Neurotoxin polypeptide, such as BoNT/A, for about 72 hours. In the subsequent step, the cells are fixed on the microtiter plate, prior to the ELISA assay. For fixing the cells, for example ice-cold methanol (−20° C.) can be added to the cells for 20 minutes at −20° C.

For performing the ELISA assay, the cells are first washed. As a wash buffer, e.g., 0.1% Triton X-100 in 10 mM PBS buffer (pH 7.4) can be used. Thereafter, endogenous proteases are quenched by a quenching buffer such as 0.6% $H_2O_2$ in 10 mM PBS (pH 7.4), followed by another wash step. In the following step, free binding sites on the microtiter plate are blocked by an appropriate blocking buffer such as, for instance, 2% BSA in 10 mM PBS buffer (pH 7.4) and 0.05% Triton X-100. Then, the cells are permeabilized, by using an appropriate detergent. As a permeabilization buffer, e.g., 0.5% Triton X-100 in 10 mM PBS buffer can be utilized. Permeabilization allows the diffusion of the antibodies through the pores formed in the cells. Thereafter, the cells are washed by washing buffer as mentioned above.

In the next step, the permeabilized cells are incubated, e.g., with a mixture of two different antibodies. The mixture comprises a first capture antibody specifically binding to the non-cleaved and Neurotoxin-cleaved substrate and a second capture antibody specifically binding to the cleavage site of the Neurotoxin-cleaved substrate. Said first and second capture antibodies can also be applied subsequently. For example, the first capture antibody can specifically bind to both non-cleaved and Neurotoxin-cleaved SNAP-25, thereby allowing for the quantification of the total amount or content of SNAP-25 in the cells. Further, this first capture antibody can be used for the normalization of the amount of cleaved SNAP-25 in the cells, upon evaluation as described herein. The second capture antibody specifically binds to the cleavage site of the Neurotoxin-cleaved substrate and therefore allows the determination and detection of the cleaved Neurotoxin substrate, such as BoNT/A-cleaved SNAP-25.

The following detection of the total Neurotoxin substrate and the Neurotoxin-cleaved Neurotoxin substrate in the method of the invention can be carried out directly on the microtiter plate or cell culture dish, i.e. within the cells. Advantageously, it is therefore not necessary to prepare cell extracts and to isolate and/or concentrate the Neurotoxin substrate from the cell lysate in the method of the invention, as in the methods described in the art. Thereafter, the cells are washed in order to remove excess antibody not bound to the respective antigen. In the subsequent step, the permeabilized cells are contacted with at least a first detection antibody and at least a second detection antibody. Said antibodies can be applied as a mixture, i.e. simultaneously, or subsequently. The first detection antibody specifically binds to the first capture antibody. Thereby, first detection complexes are being formed. The first detection antibody can be directed against the species from which the first capture antibody is derived from. For example, in case the rabbit polyclonal anti-SNAP-25 antibody S9684 (Sigma) is used as a first capture antibody specifically binding to the non-cleaved and BoNT/A-cleaved substrate SNAP-25, an anti-rabbit alkaline phosphatase-conjugated antibody can be used as a first detection antibody. The second detection antibody specifically binds to the second capture antibody. Thereby, second detection complexes are being formed. The second detection antibody can be directed against the species from which the second capture antibody is derived from. For instance, in case the mouse monoclonal antibody (mAb) 20-2-5 of the invention described elsewhere herein is used as a second capture antibody specifically binding to the BoNT/A-cleaved SNAP-25, an anti-mouse horseradish peroxidase (HRP)-conjugated antibody can be used as a second detection antibody. It is evident to those skilled in the art that the first detection antibody and the second detection antibody are conjugated with different enzymes in order to allow for the specific detection of the respective first and second capture antibody as used in the method of the invention. For instance, the HRP-based detection as described elsewhere herein can be used for the BoNT/A-cleaved SNAP-25 and the alkaline phosphatase-based detection for the total (BoNT/A-cleaved and non-cleaved) SNAP-25. Thereafter, the cells are washed again. In a subsequent step, a fluorogenic HRP substrate is added to the cells. As a HRP substrate, e.g., Amplex UltraRed (Invitrogen) can be used which is excited at 540 nm and which emits at 600 nm. Incubation with the HRP substrate is carried out for a time sufficient for sufficient conversion of substrate by the horseradish peroxidase. Subsequent to the incubation with the HRP substrate, for example, the AP substrate DiFMUP (6,8-difluoro-4-methylumbelliferyl phosphate; excitation 360 nm; emission 450 nm) can be added to the HRP substrate and the cells are incubated with a mixture of said two substrates. Incubation with said AP substrate is carried out for a time which allows for sufficient conversion of substrate by the alkaline phosphatase. As known in the art, a substrate has to be converted in an amount which is sufficient so that the measured signal is at least as high as the mean value of the blank plus three standard deviations of the mean, according to the definition of limit of detection. The limit of detection can be determined as described in the literature; see, e.g., Armbruster and Pry, Clinical Biochem. Rev. 2008, 29 (Supplement 1): S49-S52. Because the pH optimum of the alkaline phosphatase is in the alkaline region, the corresponding substrate buffer is strongly alkaline. If the alkaline phosphatase substrate is added to the HRP substrate, the reaction of the horseradish peroxidase is stopped by the alkaline pH and the alkaline phosphatase converts DiFMUP. Converted HRP substrate is not influenced by the alkaline pH. Finally, the fluorescence of the two substrates is measured as follows:

Amplex UltraRed: Excitation 540 nm; emission 600 nm
DiFMUP: Excitation 360 nm; emission 450 nm As appreciated by those skilled in the art, only those fluorogenic substrates are appropriate for detection of the first and second capture antibody in the method of the invention which exhibit different excitation/emission wave lengths of the used substrates. Only in this case, they allow for the specific detection of each antigen, i.e. the total Neurotoxin substrate (such as non-cleaved and Neurotoxin-cleaved SNAP-25) and the cleaved Neurotoxin substrate (such as Neurotoxin-cleaved SNAP-25). Thereby, it is possible to quantify the total content of Neurotoxin substrate and the content of cleaved Neurotoxin substrate in every well or cell culture dish at the same time. In light of this, it is advantageously possible to automatize the method of the invention. As set forth elsewhere herein it is envisaged that the fluorogenic substrates chosen for the method of the invention exhibit a sufficient shift between the excitation/emission spectra in order to allow for the specific detection of the respective substrate. This requirement is fulfilled, for example, for the HRP substrate Amplex and its derivatives and for the AP substrate DiFMUP. Whereas, in an optimal case, there is no overlap between the excitation/emission spectra of the used fluorogenic substrates, it has been experienced that an overlap of up to 30% in the peak area of the excitation spectra of the used fluorogenic substrates is tolerable.

As further acknowledged by those skilled in the art, the method of the present invention allows for the direct detection and quantification of Neurotoxin substrate cleaved by the Neurotoxin polypeptide in the cells, thereby determining the biological activity of said Neurotoxin polypeptide in said cells. Advantageously, the method of the invention does not require the preparation of cell lysates or extracts and the isolation or concentration of the cleaved Neurotoxin substrate from the cell lysates/extracts, which is necessary for the methods known in the art. As a consequence of this, sample material can be saved. Further, the sample preparation and the number of samples can be reduced by the method of the invention since the amount of total Neurotoxin substrate and the amount of cleaved Neurotoxin substrate in the sample can be determined at the same time. In the assays described in the art, the samples have to be subdivided in order to detect both antigens, i.e. total Neurotoxin substrate and cleaved Neurotoxin substrate, separately from each other. The method of the invention renders the subdivision of the sample unnecessary. Thereby, inhomogeneities resulting from the subdivision of samples can be avoided and sample material can be saved. Furthermore, antigens can be degraded in the assays described in the art which can falsify the detection of the cleaved Neurotoxin substrate. This is because in the assays described in the art, the cells are incubated with detergent-containing lysis buffers which, however, are not able to inactivate the Neurotoxin polypeptide or other endogenous proteases resulting in degradation of the Neurotoxin substrate upon longer storage of the samples. Stronger lysis buffers cannot be used in the ECL sandwich ELISA described in the prior art due to the required use of the cell lysate in said assay. This is because the aggregation of the above-mentioned antigens can result in unspecific adsorption of the antigens to the plastic surface of the cell culture dishes or microtiter plates which in turn disturbs the detection of the antigens by appropriate antibodies. Since the antibodies for the detection of the antigens get into contact with the lysate, too, the antibodies can also aggregate. In this case, no reliable and accurate detection of the antigen is possible anymore. The present inventors have experienced such degradation reactions by using Western blot assays for the detection of the biological activity of Neurotoxin activity described in the art. Upon longer storage of lysates at −20° C., in comparison to fresh lysate samples the detection signal of total SNAP-25 has been found to be strongly reduced and the ratio of cleaved Neurotoxin substrate SNAP-25 to un-cleaved Neurotoxin substrate SNAP-25 had shifted due to degradation processes during the freezing. It has been found by the present inventors that the degradation of the Neurotoxin substrate and/or the instability of the samples can be avoided by directly fixing the cells on the cell culture dish because both the Neurotoxin substrate and the Neurotoxin or other endogenous proteases are inactivated immediately by aggregation on the cell culture dish. This can be achieved by using, for example, fixing of the cells by methanol or other fixatives or fixation agents known in the art, such as ethanol, acetone, formaldehyde or mixtures thereof or other fixation agents described herein. The analysis of the stability of, e.g., parental SiMa cells (human neuroblastoma cells; DSMZ no.: ACC 164) and iPS-derived neurons (Whitemarsh et al. (2012), Toxicol. Sci. 126, 426-35) using this fixation method did not reveal any differences between fresh and cell culture dishes stored seven days in the refrigerator.

As used herein, the singular forms "a", "an" and "the" include both singular and plural reference unless the context clearly dictates otherwise. By way of example, "a cell" refers to one or more than one cell.

As used herein, the term "about" when qualifying a value of a stated item, number, percentage, or term refers to a range of plus or minus 10 percent, 9 percent, 8 percent, 7 percent, 6 percent, 5 percent, 4 percent, 3 percent, 2 percent or 1 percent of the value of the stated item, number, percentage, or term. Preferred is a range of plus or minus 10 percent.

The terms "comprising", "comprises" and "comprised of" as used herein are synonyms with "including", "includes" or "containing", "contains", and are inclusive or open-ended and do not exclude additional, non-recited members, elements or method steps. Evidently, the term "comprising" encompasses the term "consisting of". More specifically, the term "comprise" as used herein means that the claim encompasses all the listed elements or method steps, but may also include additional, unnamed elements or method steps. For example, a method comprising steps a), b) and c) encompasses, in its narrowest sense, a method which consists of steps a), b) and c). The phrase "consisting of" means that the composition (or device, or method) has the recited elements (or steps) and no more. In contrast, the term "comprises" can encompass also a method including further steps, e.g., steps d) and e), in addition to steps a), b) and c).

In case numerical ranges are used herein such as "in a concentration between 1 and 5 micromolar", the range includes not only 1 and 5 micromolar, but also any numerical value in between 1 and 5 micromolar, for example, 2, 3 and 4 micromolar.

The term "in vitro" as used herein denotes outside, or external to, the animal or human body. The term "in vitro" as used herein should be understood to include "ex vivo". The term "ex vivo" typically refers to tissues or cells removed from an animal or human body and maintained or propagated outside the body, e.g., in a culture vessel. The term "in vivo" as used herein denotes inside, or internal to, the animal or human body.

The term "Neurotoxin polypeptide" as used herein denotes *Clostridium botulinum* and *Clostridium tetani* Neurotoxins, i.e. Botulinum toxins (BoNTs) and Tetanus toxin (TeNT). More specifically, said term encompasses BoNT/A, BoNT/B, BoNT/C1, BONT/D, BONT/E, BoNT/F, BoNT/G, and Tetanus Neurotoxin (TeNT). The Neurotoxin polypeptide and, in particular, its light chain and heavy chain are derivable from one of the antigenically different serotypes of Botulinum Neurotoxins indicated above. In an aspect, said light and heavy chain of the neurotoxin polypeptide are the light and heavy chain of a neurotoxin selected from the group consisting of: BoNT/A, BoNT/B, BoNT/C1, BONT/D, BONT/E, BONT/F. BoNT/G or TeNT. In another aspect, the polynucleotide encoding said Neurotoxin polypeptides comprises a nucleic acid sequence as shown in SEQ ID NO: 1 (BoNT/A), SEQ ID NO: 3 (BoNT/B), SEQ ID NO: 5 (BoNT/C1), SEQ ID NO: 7 (BoNT/D), SEQ ID NO: 9

(BoNT/E), SEQ ID NO: 11 (BoNT/F), SEQ ID NO: 13 (BoNT/G) or SEQ ID NO: 15 (TeNT). Moreover, encompassed is, in an aspect, a polynucleotide comprising a nucleic acid sequence encoding an amino acid sequence as shown in any one of SEQ ID NO: 2 (BoNT/A), SEQ ID NO: 4 (BoNT/B), SEQ ID NO: 6 (BoNT/C1), SEQ ID NO: 8 (BoNT/D), SEQ ID NO: 10 (BoNT/E), SEQ ID NO: 12 (BoNT/F), SEQ ID NO: 14 (BoNT/G) or SEQ ID NO: 16 (TeNT). Further encompassed is in an aspect of the means and methods of the present invention, a Neurotoxin polypeptide comprising or consisting of an amino acid sequence selected from the group consisting of: SEQ ID NO: 2 (BoNT/A), SEQ ID NO: 4 (BoNT/B), SEQ ID NO: 6 (BoNT/C1), SEQ ID NO: 8 (BoNT/D), SEQ ID NO: 10 (BoNT/E), SEQ ID NO: 12 (BoNT/F), SEQ ID NO: 14 (BoNT/G) and SEQ ID NO: 16 (TeNT).

In another aspect, the said polynucleotide is a variant of the aforementioned polynucleotides comprising one or more nucleotide substitutions, deletions and/or additions which in still another aspect may result in a polypeptide having one or more amino acid substitutions, deletions and/or additions. Moreover, a variant polynucleotide of the invention shall in another aspect comprise a nucleic acid sequence variant being at least 40%, at least 50%, at least 60%, at least 70%, at least 75%, at least 80%, at least 85%, at least 90%, at least 95%, at least 96%, at least 97%, at least 98% or at least 99% identical to the nucleic acid sequence as shown in any one of SEQ ID NOs: 1, 3, 5, 7, 9, 11, 13 or 15 or a nucleic acid sequence variant which encodes an amino acid sequence being at least 40%, at least 50%, at least 60%, at least 70%, at least 75%, at least 80%, at least 85%, at least 90%, at least 95%, at least 96%, at least 97%, at least 98% or at least 99% identical to the amino acid sequence as shown in any one of SEQ ID NOs: 2, 4, 6, 8, 10, 12, 14, or 16. The term "identical" as used herein refers to sequence identity characterized by determining the number of identical amino acids between two nucleic acid sequences or two amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215, 403). The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wisconsin, USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. In an aspect, each of the aforementioned variant polynucleotides encodes a polypeptide retaining one or more and, in another aspect, all of the biological properties of the respective Neurotoxin polypeptide, i.e. the BoNT/A, BONT/B, BONT/C1, BONT/D, BONT/E, BONT/F, BoNT/G or Tetanus Neurotoxin (TeNT). Those of skill in the art will appreciate that full biological activity is maintained only after proteolytic activation, even though it is conceivable that the unprocessed precursor can exert some biological functions or be partially active. "Biological properties" as used herein refers to (a) receptor binding, (b) internalization, (c) translocation across the endosomal membrane into the cytosol, and/or (d) endoproteolytic cleavage of proteins involved in synaptic vesicle membrane fusion. In vivo assays for assessing biological activity include the mouse LD50 assay and the ex vivo mouse hemidiaphragm assay as described by Pearce et al. (Pearce 1994, Toxicol. Appl. Pharmacol. 128: 69-77) and Dressler et al. (Dressler 2005, Mov. Disord. 20:1617-1619, Keller 2006, Neuroscience 139: 629-637). The biological activity is commonly expressed in Mouse Units (MU). As used herein, 1 MU is the amount of neurotoxic component, which kills 50% of a specified mouse population after intraperitoneal injection, i.e. the mouse i.p. LD50. In a further aspect, the variant polynucleotides can encode Neurotoxins having improved or altered biological properties, e.g., they may comprise cleavage sites which are improved for enzyme recognition or may be improved for receptor binding or any other property specified above.

Accordingly, the term "biological activity of a Neurotoxin polypeptide" as used herein means the biological properties characteristic for a Neurotoxin polypeptide, namely, a) receptor binding, (b) internalization, (c) translocation across the endosomal membrane into the cytosol, and/or (d) endoproteolytic cleavage of proteins involved in synaptic vesicle membrane fusion. It is envisaged that the Neurotoxin polypeptide as used herein exhibits at least one of the properties a) to d) mentioned above, preferably endoproteolytic cleavage of proteins involved in synaptic vesicle membrane fusion, or two or three or all four biological properties listed in a) to d).

Aspects of the present disclosure comprise, in part, a cell from an established cell line. As used herein, the term "cell" refers to any eukaryotic cell susceptible to Neurotoxin intoxication by a Neurotoxin such as, e.g., BoNT/A, or any eukaryotic cell that can uptake a Neurotoxin. The term cell encompasses cells from a variety of organisms, such as, e.g., murine, rat, porcine, bovine, equine, primate and human cells; from a variety of cell types such as, e.g., neuronal and non-neuronal; and can be isolated from or part of a heterogeneous cell population, tissue or organism. As used herein, the term "established cell line" is synonymous with "immortal cell line," or "transformed cell line" and refers to a cell culture of cells selected for indefinite propagation from a cell population derived from an organism, tissue, or organ source. By definition, an established cell line excludes a cell culture of primary cells. As used herein, the term "primary cells" are cells harvested directly from fresh tissues or organs and do not have the potential to propagate indefinitely. For example, primary neuronal cells can be used in the method of the invention. An established cell line can comprise a heterogeneous population of cells or a uniform population of cells. An established cell line derived from a single cell is referred to as a clonal cell line. An established cell line can be one whose cells endogenously express all component necessary for the cells to undergo the overall cellular mechanism whereby a Neurotoxin, such as BoNT/A, proteolytically cleaves a substrate, such as SNAP-25, and encompasses the binding of a Neurotoxin to a Neurotoxin receptor, such as BoNT/A, to a BoNT/A receptor, the internalization of the neurotoxin/receptor complex, the translocation of the Neurotoxin light chain from an intracellular vesicle into the cytoplasm and the proteolytic cleavage of a Neurotoxin substrate. Alternatively, an established cell line can be one whose cells have had introduced from an exogenous source at least one component necessary for the cells to undergo the overall cellular mechanism whereby a Neurotoxin, such as BoNT/A, proteolytically cleaves a substrate, such as SNAP-25, and encompasses the binding of a Neurotoxin to a receptor, such as BoNT/A to a BoNT/A receptor, the internalization of the neurotoxin/receptor complex, the translocation of the Neurotoxin light chain from an intracellular vesicle into the cytoplasm and the proteolytic cleavage of a Neurotoxin substrate. Also referred to as a genetically-engineered cell line, cells from such an established cell line may, e.g., express an exogenous FGFR2, an exogenous FGFR3, an exogenous SV2, an exogenous Neurotoxin substrate such as SNAP-25, or any combination thereof.

The term "cell(s) susceptible to Neurotoxin intoxication" as denoted herein means a cell that can undergo the overall cellular mechanisms whereby a Neurotoxin polypeptide (e.g., BoNT/A) cleaves a Neurotoxin substrate (e.g., the BoNT/A substrate SNAP-25) and encompasses the binding of the Neurotoxin to its corresponding receptor (e.g., binding of BoNT/A to the BoNT/A receptor), the internalization of the Neurotoxin/receptor complex, the translocation of the Neurotoxin light chain from an intracellular vesicle into the cytoplasm and the proteolytic cleavage of the Neurotoxin substrate. Assays for determining the biological activity of Neurotoxin polypeptides are well known in the art and also described elsewhere herein; see, e.g., Pellett et al. (2011), Biochem. Biophys. Res. Commun. 404, 388-392; Whitemarsh et al. (2012), Toxicol. Sci. 126, 426-35. Accordingly, a "cell susceptible to Neurotoxin intoxication" as used herein means a Neurotoxin sensitive cell. The mentioned term comprises a cell or a cell line, for example, an isolated, primary cell or a cell line thereof or a cell of an established cell line or an established cell line, for example, tumor cells or tumor cell lines which are capable of differentiating to neuronal cells, such as neuroblastoma cells or neuroblastoma cell lines as defined elsewhere herein. For example, said neuroblastoma cell line can be a SiMa cell line which is commercially available from DSMZ (ACC 164). Specific clones of the cell line SiMa are furthermore disclosed in WO 2010/105234. Other neuroblastoma cell lines which can be used in the method of the invention can be obtained from ATCC or DSMZ, under the following ATCC or DSMZ numbers: Cell line N1E-115 under CRL-2263, cell line Neuro2a under CCL-131, cell line SH-SY5Y under CRL-2266, cell line PC12 under CRL-1721, cell line MHH-NB-11 under ACC 157 (DSMZ) and cell line SK-N-BE(2) under CRL-2271. Other tumor cells which are susceptible to Neurotoxin intoxication are P-19 cells (murine embryonal carcinoma cell line) (DSMZ no. ACC 316). Further encompassed by cells susceptible to Neurotoxin intoxication are induced pluripotent stem cell (iPS)-derived neurons, preferably human induced pluripotent stem cell (iPS)-derived neurons; see, e.g., Whitemarsh et al. (2012), loc. cit. Such human iPS-derived neurons are also commercially available, for instance, from Cellular Dynamics. Methods of generating iPS cells are described, for example, in Yu et al. (Science 2009 May 8; 324(5928): 797-801. Epub 2009), WO 2011/056971 and WO 2011/025852. In some aspects, iPS are differentiated into neurons using suitable methods, e.g., those described in WO 2012/135621 and U.S. Patent Applications US 2010/0279403 and US 2010/0216181.

The term "fixing the cells" means fixing the cells using methods described in the art. Generally, fixation is a chemical process by which biological tissues are preserved from decay, thereby preventing autolysis. Fixation terminates any ongoing biochemical reactions, and may also increase the mechanical strength or stability of the treated tissues. Fixation preserves a sample of biological material such as a tissue or cells as close to its natural state as possible in the process of preparing said tissue or cells for examination or analysis. To this end, a fixative usually acts to disable intrinsic biomolecules—particularly proteolytic enzymes—which otherwise digests or damages the sample. Further, a fixative typically protects a sample from extrinsic damage. Fixatives are toxic to most common microorganisms including bacteria that might exist in a tissue or cell culture or which might otherwise colonize the fixed tissue or cell culture. In addition, many fixatives chemically alter the fixed material to make it less palatable either indigestible or toxic to opportunistic microorganisms. Finally, fixatives often alter the cells or tissues on a molecular level to increase their mechanical strength or stability. This increased strength and rigidity can help preserve the morphology such as shape and structure of the sample as it is processed for further analysis. It is evident to those skilled in the art that the choice of fixative and fixation protocol may depend on the additional processing steps and final analyses that are planned. For example, immunohistochemistry uses antibodies that bind specifically to a specific protein target, the antigen. Prolonged fixation can chemically mask these targets and prevent antibody binding. In these cases, for example, a quick fixation method using cold formalin can be used. Alternatively, the cells can be fixed by adding ice-cold methanol (−20° C.). Besides aldehydes such as formaldehyde or glutaraldehyde and alcohols such as ethanol or methanol, oxidizing agents, Hepes-glutamic acid buffer-mediated organic solvent protection effect (HOPE) fixative, acetone, or mixtures thereof, such as a mixture of methanol and acetone, methanol and ethanol, paraformaldehyde and Triton X-100, or paraformaldehyde and methanol, can be used in fixation protocols. In one aspect of the method of the invention, fixing the cells is carried out by the addition of a fixation agent selected from the group consisting of: methanol, ethanol, acetone, formaldehyde or mixtures thereof. To ensure and/or support free access of the antibody to its antigen, the cells can, optionally, be permeabilized by using an appropriate permeabilization buffer comprising at least one detergent, such as Triton X-100. A permeabilization buffer which can be used in the method of the invention is, e.g., 0.5% Triton X-100 in 10 mM PBS buffer. In other aspects of the methods of the invention, the cells can be permeabilized by using a permeabilization buffer such as PBS comprising at least one detergent selected from Tween 20, Saponin. Digitonin or n-Octyl-β-glucopyranoside. In other aspects, mixtures of two or more of the detergents mentioned herein can be used in the said permeabilization buffer. In general, fixation strengths and times are considerably shorter for cells than on the thicker, structurally complex tissue sections. For immunocytochemistry, sample preparation essentially entails fixing the target cells to the slide, cell culture dish or microtiter plate. Perfect fixation would immobilize the antigens, while retaining authentic cellular and subcellular architecture and permitting unhindered access of antibodies to all cells and subcellular compartments. Wide ranges of fixatives as exemplified above are commonly used, and the correct choice of method will depend on the nature of the antigen being examined and on the properties of the antibody used. Fixation methods fall generally into two classes: organic solvents and cross-linking reagents. Organic solvents such as alcohols and acetone remove lipids and dehydrate the cells, while precipitating the proteins on the cellular architecture. Cross-linking reagents such as paraformaldehyde form intermolecular bridges, normally through free amino groups, thus creating a network of linked antigens. Cross-linkers preserve cell structure better than organic solvents, but may reduce the antigenicity of some cell components, and often require the addition of a permeabilization step as indicated above, to allow access of the antibody to the specimen. Fixation with both methods may denature protein antigens, and for this reason, antibodies prepared against denatured proteins may be more useful for cell staining. The appropriate fixation method should be chosen according to the relevant application. Fixing methods of cells are well described in the art (see, e.g., Methods in cell biology, Volume 37: Antibodies in cell biology; Edited by David J. Asai; 1993, Academic Press Inc.).

The term "contacting" as used in accordance with the method of the invention means bringing the cells and the respective antibodies in physical proximity as to allow physical and/or chemical interaction. Suitable conditions which allow for specific interaction are well known to the person skilled in the art. Evidently, said conditions will depend on the antibodies and the cells to be applied in the method of the present invention and can be adapted routinely by the person skilled in the art. Moreover, a time being sufficient to allow interaction can also be determined by the skilled worker without further ado. It is to be understood that between the individual steps of contacting the cells and the respective antibodies recited in the method of the present invention, washing steps may be performed in order to obtain suitable conditions for contacting. For example, after contacting the cells with at least a first capture antibody specifically to the non-cleaved and Neurotoxin-cleaved substrate and with at least a second capture antibody specifically binding to the cleavage site of the Neurotoxin-cleaved substrate in step c) of the method of the invention, a washing step can be incorporated to remove the remaining solution and/or excess first and second capture antibody, prior to applying the first detection antibody and/or second detection antibody. Similarly, after bringing the cells into contact with the first and/or second detection antibody in the method of the invention, a wash step can be included. An appropriate wash buffer is, for example, 0.1% Triton X-100 in 10 mM PBS buffer (pH 7.4). More specifically, the term "contacting" as used herein, refers to bringing the cells into contact with at least a first capture antibody specifically binding to the non-cleaved and Neurotoxin-cleaved substrate and with at least a second capture antibody specifically binding to the cleavage site of the Neurotoxin-cleaved substrate, under conditions which allow for binding of said capture antibodies to said substrates, in step c) of the method of the invention. The first and second capture antibody can be applied to the cells simultaneously, for example, as a mixture, or subsequently. "Contacting" further refers to bringing into contact the cells with at least a first detection antibody specifically binding to the first capture antibody, under conditions which allow for binding of said first detection antibody to said first capture antibody, and at least a second detection antibody specifically binding to the second capture antibody, under conditions which allow for binding of said second detection antibody to said second capture antibody, in step d) of the method of the invention. Thereby, first and second detection complexes are being formed. Alternatively, the first and second detection antibodies can also be applied subsequently.

As used herein, the term "antibody" refers to a molecule generated by an immune system that was made in response to a particular antigen that specifically binds to that antigen, and includes both naturally occurring antibodies and non-naturally occurring antibodies. An "antibody" as used herein encompasses a monoclonal antibody, a polyclonal antibody, a single chain antibody, a dimer or a multimer, a chimerized antibody, a bispecific antibody, a bispecific single chain antibody, a multispecific antibody, a synthetic antibody, a humanized antibody, a bifunctional antibody, a cell-associated antibody like an Ig receptor, a linear antibody, a diabody, a minibody, or a fragment of any of said antibodies. Fragments of said antibodies include, e.g., Fab, Fv, or scFv fragments, or chemically modified derivatives of any of these fragments. Antibodies can be manufactured by using methods which are described in the art; see, for example, Harlow and Lane "Antibodies, A Laboratory Manual", CSH Press, Cold Spring Harbor, 1988. Monoclonal antibodies can be prepared by the techniques originally described in Köhler 1975, Nature 256, 495, and Galfré 1981, Meth. Enzymol. 73, 3. Said techniques comprise the fusion of mouse myeloma cells to spleen cells derived from immunized mammals. Antibodies can be further improved by techniques well known in the art. For example, surface plasmon resonance as employed in the Biacore system can be used to increase the efficiency of phage antibodies which bind to the epitope; see, e.g., Schier 1996, Human Antibodies Hybridomas 7, 97; Malmborg 1995. J. Immunol. Methods 183, 7. Antibodies as used herein also comprise functional equivalents of antibodies, i.e. agents which are capable of specifically binding to the desired epitopes or parts of the Neurotoxin substrates. In an aspect, such functional equivalents comprise binding proteins specifically binding to Neurotoxin substrates or domains thereof which are capable of mediating the said specific binding. An antibody as used herein can be a full-length immunoglobulin molecule comprising the VH and VL domains, as well as a light chain constant domain (CL) and heavy chain constant domains, CH1, CH2 and CH3, or an immunologically active fragment of a full-length immunoglobulin molecule, such as, e.g., a Fab fragment, a F(ab')$_2$ fragment, a Fc fragment, a Fd fragment, or a Fv fragment. An antibody can be derived from any vertebrate species (e.g., human, goat, horse, donkey, murine, rat, rabbit, or chicken), and can be of any type (e.g., IgG, IgE, IgM, IgD, or IgA), class (e.g., IgA, IgD, IgE. IgG, or IgM) or subclass (IgG1, IgG2, IgG3, IgG4, IgA1 or IgA2). For general disclosure on the structure of naturally occurring antibodies, non-naturally occurring antibodies, and antigenic compound-binding fragments thereof, see, e.g., Plueckthun in The Pharmacology of Monoclonal Antibodies, vol. 113, Rosenburg and Moore eds., Springer-Verlag, New York, pp. 269-315 (1994); Borrabeck, Antibody Engineering 2d ed. (Oxford University Press). Naturally-occurring antibodies are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The complete antigen-recognition and antigen-binding site is contained within the variable domains of the antibody, i.e., the Fv fragment. This fragment includes a dimer of one heavy chain variable domain (VH) and one light chain variable domain (VL) in tight, non-covalent association. Each domain comprises four framework regions (FR), which largely adopting a beta-sheet configuration, connected by three hypervariable regions, which form loops connecting, and in some cases form part of, the beta-sheet structure. Each hypervariable region comprises an amino acid sequence corresponding to a complementarity determining region (CDRs). Collectively, it the three-dimensional configuration of the six CDR regions that define an antigen-binding site on the surface of the VH-VL dimer that confers antigen-binding specificity. See e.g., Cyrus Chothia, et al., Conformations of Immunoglobulin Hypervariable Regions, Nature 342(6252): 877-883 (1989); Elvin A. Kabat, et al Sequences of Proteins of Immunological Interest, 5th Ed. Public Health Service, National Institutes of Health, Bethesda, Md. (1991). The constant domains of the antibody are not involved directly in binding an antibody to an antigen, but exhibit various effector functions, such as participation of the antibody in antibody dependent cellular cytotoxicity.

"Selective binding" or "specific binding" as used herein includes binding properties such as, e.g., binding affinity, binding specificity, and binding avidity; see, e.g., David J. King, Applications and Engineering of Monoclonal Antibodies, pp. 240 (1998). Binding affinity refers to the length of time the antibody resides at its epitope binding site, and can be viewed as the strength with which an antibody binds its epitope. Binding affinity can be described an antibody's equilibrium dissociation constant (KD), which is defined as the ratio Kd/Ka at equilibrium. Ka is the antibody's association rate constant and Kd is the antibody's dissociation rate constant. Binding affinity is determined by both the association and the dissociation and alone neither high association nor low dissociation can ensure high affinity. The association rate constant (Ka), or on-rate constant (Kon), measures the number of binding events per unit time, or the propensity of the antibody and the antigen to associate reversibly into its antibody-antigen complex. The association rate constant is expressed in $M^{-1} s^{-1}$, and is symbolized as follows: [Ab]×[Ag]×Kon. The larger the association rate constant, the more rapidly the antibody binds to its antigen, or the higher the binding affinity between antibody and antigen. The dissociation rate constant (Kd), or off-rate constant (Koff), measures the number of dissociation events per unit time propensity of an antibody-antigen complex to separate (dissociate) reversibly into its component molecules, namely the antibody and the antigen. The dissociation rate constant is expressed in $s^{-1}$, and is symbolized as follows: [Ab+Ag]×Koff. The smaller the dissociation rate constant, the more tightly bound the antibody is to its antigen, or the higher the binding affinity between antibody and antigen. The equilibrium dissociation constant (KD) measures the rate at which new antibody-antigen complexes formed equals the rate at which antibody-antigen complexes dissociate at equilibrium. The equilibrium dissociation constant is expressed in M, and is defined as Koff/Kon=[Ab]×[Ag]/[Ab+Ag], where [Ab] is the molar concentration of the antibody, [Ag] is the molar concentration of the antigen, and [Ab+Ag] is the of molar concentration of the antibody-antigen complex, where all concentrations are of such components when the system is at equilibrium. The smaller the equilibrium dissociation constant, the more tightly bound the antibody is to its antigen, or the higher the binding affinity between antibody and antigen. Thus, in one aspect of the method of the invention, the first capture antibody specifically binding to the non-cleaved and Neurotoxin-cleaved substrate can have an association rate constant of, e.g., less than $1\times10^5 M^{-1} s^{-1}$, less than $1\times10^6 M^{-1} s^{-1}$, less than $1\times10^7 M^{-1} s^{-1}$ or less than $1\times10^8 M^{-1} s^{-1}$. In another aspect, the first capture antibody specifically binding to the non-cleaved and Neurotoxin-cleaved substrate can have an association rate constant of, e.g., more than $1\times10^5 M^{-1} s^{-1}$, more than $1\times10^6 M^{-1} s^{-1}$, more than $1\times10^7 M^{-1} s^{-1}$ or more than $1\times10^8 M^{-1} s^{-1}$. In a further aspect, the first capture antibody specifically binding to the non-cleaved and Neurotoxin-cleaved substrate can have a disassociation rate constant of, e.g., less than $1\times10^{-3} M^{-1} s^{-1}$, less than $1\times10^4 M^{-1} s^{-1}$, less than $1\times10^5 M^{-1} s^{-1}$ or less than $1\times10^{-6} M^{-1} s^{-1}$. In a still further aspect, the first capture antibody specifically binding to the non-cleaved and Neurotoxin-cleaved substrate can have a disassociation rate constant of, e.g., more than $1\times10^{-3} M^{-1} s^{-1}$, more than $1\times10^4 M^{-1} s^{-1}$, more than $1\times10^{-5} M^{-1} s^{-1}$ or more than $1\times10^{-6} M^{-1} s^{-1}$. In a further aspect, the second capture antibody specifically binding to the specifically binding to the cleavage site of the Neurotoxin-cleaved substrate can have an association rate constant of, e.g., less than $1\times10^5 M^{-1} s^{-1}$, less than $1\times10^6 M^{-1} s^{-1}$, less than $1\times10^7 M^{-1} s^{-1}$ or less than $1\times10^8 M^{-1} s^{-1}$. In another aspect, the second capture antibody specifically binding to the specifically binding to the cleavage site of the Neurotoxin-cleaved substrate can have an association rate constant of, e.g., more than $1\times10^5 M^{-1} s^{-1}$, more than $1\times10^6 M^{-1} s^{-1}$, more than $1\times10^7 M^{-1} s^{-1}$ or more than $1\times10^8 M^{-1} s^{-1}$. In a further aspect, the second capture antibody specifically binding to the specifically binding to the cleavage site of the Neurotoxin-cleaved substrate can have a disassociation rate constant of, e.g., less than $1\times10^{-3} M^{-1} s^{-1}$, less than $1\times10^4 M^{-1} s^{-1}$, less than $1\times10^{-5} M^{-1} s^{-1}$ or less than $1\times10^{-6} M^{-1} s^{-1}$. In a still further aspect, the second capture antibody specifically binding to the specifically binding to the cleavage site of the Neurotoxin-cleaved substrate can have a disassociation rate constant of, e.g., more than $1\times10^{-3} M^{-1} s^{-1}$, more than $1\times10^4 M^{-1} s^{-1}$, more than $1\times10^5 M^{-1} s^{-1}$ or more than $1\times10^{-6} M^{-1} s^{-1}$.

A target antigen such as the Neurotoxin-cleaved or non-cleaved Neurotoxin substrates SNAP-25, VAMP/Synaptobrevin, or Syntaxin generally has one or more binding sites, also called epitopes, which are recognized by the CDR-formed antigen-binding site of the antibody. As used herein, an "epitope" is synonymous with "antigenic determinant" and refers to the site on a target antigen, such as, e.g., a peptide, polypeptide, polysaccharide or lipid-containing molecule, capable of specific binding to an immunoglobulin or T-cell receptor or otherwise interacting with a molecule. Each antibody that specifically binds to a different epitope has a different structure. Thus, one antigen may have more than one corresponding antibody. "Specific binding" as referred to herein can be tested by various well known techniques including, e.g., competition experiments and Western blots. An epitope as used in accordance with the invention relates to the antigenic determinant in the Neurotoxin substrates, e.g. SNAP-25, VAMP/Synaptobrevin, or Syntaxin which is recognized by the antibody. As used herein, the term "specifically" means selectively and refers to having a unique effect or influence or reacting in only one way or with only one thing. As used herein, the term "specifically binds" or "selectively binds" when made in reference to an antibody or binding protein or binding domain, refers to the discriminatory binding of the antibody or binding protein/domain to the indicated target epitope such that the antibody or binding protein/domain does not substantially cross react with non-target epitopes. The minimal size of a peptide epitope, as defined herein, is about five amino acid residues, and a peptide epitope typically comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 30 amino acid residues. A peptide epitope may be a linear or a discontinuous epitope. A discontinuous epitope comprises amino acid residues that are not adjacent in the primary structure of the peptide but are brought together into an epitope by way of the secondary, tertiary or quaternary structure of the peptide. Furthermore, it is also noted that an epitope may comprise a portion of a molecule other than an amino acid sequence such as, e.g., carbohydrate moiety, lipid moiety like glycolipids or lipoproteins, or a chemically modified amino acid moiety like a phosphorylated amino acid.

According to the method of the present invention, the "first capture antibody" specifically binds to an epitope comprised by the non-cleaved and Neurotoxin-cleaved substrate. Said Neurotoxin substrates can be, example, for SNAP-25, VAMP/Synaptobrevin, or Syntaxin. For instance, SNAP-25 is a known substrate of BONT/A, BONT/C1 and BoNT/E. VAMP/Synaptobrevin is a substrate of BoNT/B, BONT/D. BONT/F, BoNT/G and TeNT, whereas Syntaxin is a substrate of BoNT/C1. Said first capture antibody allows for the determination of the total amount, i.e. complete content of the respective Neurotoxin substrate in the cells. For example, in SNAP-25, having a total length of 205 amino acid residues, the cleavage site for BoNT/A is localized between amino acid residues Gln 197 and Arg 198. Accordingly, an antibody specifically binding to an epitope positioned N-terminally to the BoNT/A cleavage site, i.e. an epitope localized between amino acid residues 1 and 198 of SNAP-25 can be used as first capture antibody. For example, said antibody can specifically bind to an N-terminal epitope or an epitope positioned in the mid-part of SNAP-25. For BoNT/C1, an epitope positioned N-terminally to the BoNT/C1 cleavage site (Arg 198-Ala 199), i.e. between amino acid residues 1 and 199 of SNAP-25 can be used as first capture antibody. For BoNT/E, an epitope positioned N-terminally to the BoNT/E cleavage site(Arg 180-Ile 181), i.e. between amino acid residues 1 and 181 of SNAP-25 can be used as first capture antibody. If VAMP is used as a Neurotoxin substrate, an epitope positioned N-terminally to the BoNT/B cleavage site (Gln 76-Phe 77), i.e. between amino acid residues 1 and 77 of VAMP can be used as first capture antibody. An epitope positioned N-terminally to the BoNT/D cleavage site (Lys 59-Leu 60), i.e. between amino acid residues 1 and 60 of VAMP2 can be used as first capture antibody. An epitope positioned N-terminally to the BoNT/F cleavage site (Gln 58-Lys 59), i.e. between amino acid residues 1 and 59 of VAMP2 can be used as first capture antibody. An epitope positioned N-terminally to the BoN/G cleavage site (Ala 81-Ala 82), i.e. between amino acid residues 1 and 82 of VAMP2 can be used as first capture antibody. If Syntaxin is used as a substrate, an epitope positioned N-terminally to the BoN/C1 cleavage site (Lys 253-Ala 254), i.e. between amino acid residues 1 and 254 of Syntaxin 1a can be used as first capture antibody.

A neurotoxin cleavage site recognized and cleaved by the BoNT/A protease, in an aspect of the invention, is derived from a protein that is sensitive to cleavage by BoNT/A. In an aspect, such a protein is human SNAP-25A or SNAP-25B or a homolog, paralog or ortholog thereof from rat, mouse, bovine, *Danio, Carassius, Xenopus, Torpedo, Strongylocentrotus, Loligo, Lymnaea* or *Aplysia*. Suitable cleavage sites derived from said proteins are disclosed, e.g., in EP 1 926 744 B1.

A neurotoxin cleavage site recognized and cleaved by the BoNT/B protease, in an aspect of the invention, is derived from a protein that is sensitive to cleavage by BoNT/B. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the BoNT/C1 protease, in an aspect of the invention, is derived from a protein that is sensitive to cleavage by BoNT/C1. In an aspect, such a protein is human and mouse Syntaxin 1A, Syntaxin 1B1, Syntaxin 2-1, Syntaxin 2-2, Syntaxin 2-3, Syntaxin 3A or Syntaxin 1B2, bovine or rat Syntaxin 1A, Syntaxin 1B1 or Syntaxin 1B2, rat Syntaxin 2 or Rat syntaxin 3, mouse Syntaxin 1A, Syntaxin 1B1, Syntaxin 1B2, Syntaxin 2, Syntaxin 3A, Syntaxin 3B or Syntaxin 3C, chicken Syntaxin 1A or Syntaxin 2; *Xenopus* Syntaxin 1A or Syntaxin 1B, *Danio* Syntaxin 1A, Syntaxin 1B or Syntaxin 3, *Torpedo* Syntaxin 1A or Syntaxin 1B, *Strongylocentrotus* Syntaxin 1A or Syntaxin 1B, *Drosophila* Syntaxin 1A or Syntaxin 1B, *Hirudo* Syntaxin 1A or Syntaxin 1B, *Loligo* Syntaxin 1A or Syntaxin 1B, *Lymnaea* Syntaxin 1A or Syntaxin 1B or any ortholog, paralog or homolog thereof. Suitable cleavage sites derived from said proteins are disclosed in EP 1 926 744 B1.

A neurotoxin cleavage site recognized and cleaved by the BoNT/D protease, in an aspect of the invention, is derived from a protein that is sensitive to cleavage by BoNT/D. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the BoNT/E protease, in an aspect of the invention, is derived from a protein that is sensitive to cleavage by BoNT/E. In an aspect, such a protein is, such a protein is human SNAP-25A or B or a homolog, paralog or ortholog thereof from rat, mouse, bovine, *Danio, Carassius, Xenopus, Torpedo, Strongylocentrotus, Loligo, Lymnaea* or *Aplysia*. Suitable cleavage sites derived from said proteins are disclosed in EP 1 926 744 B1.

A neurotoxin cleavage site recognized and cleaved by the BoNT/F protease, in an aspect of the invention, is derived from a protein that is sensitive to cleavage by BoNT/F. In an aspect, such a protein is, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the BoNT/G protease, in an aspect of the invention, is derived from a protein that is sensitive to cleavage by BoNT/G. In an aspect, such a protein is, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

A neurotoxin cleavage site recognized and cleaved by the TeNT protease, in an aspect of the invention, is derived from a protein that is sensitive to cleavage by TeNT. In an aspect, such a protein is human or mouse VAMP-1, VAMP-2 and VAMP-3/cellubrevin, bovine VAMP-2, rat VAMP-2 or VAMP-3, chicken VAMP-1, VAMP-2 or VAMP-3, *Torpedo* VAMP-1, *Strongylocentrotus* VAMP, *Drosophila* sybA, synB, synC, synD, or syn, *Hirudo* VAMP, *Xenopus* VAMP-2 or VAMP-3, *Danio* VAMP-1 or VAMP-2, *Loligo* VAMP, *Lymnaea* VAMP, *Aplysia* VAMP or *Caenorhabditis* SNB1-like or any ortholog, paralog or homolog thereof. Suitable cleavage sites derived from said proteins are disclosed in EP 1 926 744 B1.

Examples for appropriate antibodies which can be used as first capture antibodies in the method of the invention include, for example, the rabbit polyclonal anti-SNAP-25 antibody S9684 (Sigma) (Fernández-Salas E, Wang J, Molina Y, Nelson J B, Jacky B P S, et al. (2012) Botulinum Neurotoxin Serotype a Specific Cell-Based Potency Assay to Replace the Mouse Bioassay. PLOSONE7(11): e49516. doi: 10.1371/journal.pone.0049516), the rabbit polyclonal anti-SNAP25 antibody PA5-19708 (Pierce Antibodies), the rabbit polyclonal anti-SNAP25 antibody PA5-19701 (Pierce Antibodies), the VAMP/Synaptobrevin antibody sc-13992 (Santa Cruz Biotechnology) or #104 203 (Synaptic Systems), or the Syntaxin antibody ADI-VAM-SV013 (Enzo Life Sciences).

In one aspect, the first capture antibody that recognizes the non-cleaved and Neurotoxin-cleaved substrate in order to determine the total amount of Neurotoxin substrate in the cell is used for normalization, as shown in the following Examples.

The "second capture antibody" as used herein specifically binds to the cleavage site of the Neurotoxin-cleaved substrate. Accordingly, said second capture antibody recognizes selectively the Neurotoxin substrate cleaved by the Neurotoxin, for example, the BoNT/A SNAP-25-cleaved product. In contrast, said second capture antibody is not able to bind to the non-cleaved Neurotoxin substrate, such as, e.g., non-cleaved SNAP-25. Examples for appropriate antibodies which can be used as second capture antibodies in the method of the invention include, for example, the mouse monoclonal antibodies of the invention as indicated below, the mouse monoclonal antibody MC-6053 (R&D Systems) which recognizes the BoNT/A-cleaved SNAP-25 ((Baldwin and Barbieri 2007, Biochemistry 46, 3200-3210), as well as the mouse monoclonal antibody DMAB4345 (Creative Diagnostics).

The present invention provides in a further aspect, novel monoclonal antibodies specifically binding to the cleavage site of the Neurotoxin-cleaved SNAP-25, i.e. to Neurotoxin-cleaved SNAP-25 only, whereas they do not bind to non-cleaved SNAP-25. Said monoclonal antibodies have been generated and characterized as described in the following Examples and have been found particularly suitable as second capture antibodies for the method of the invention, due to their high affinity and specificity for Neurotoxin-cleaved SNAP-25. Preferably, the monoclonal antibodies of the invention recognize and specifically bind to the epitope SNAP-25$_{190-197}$ "TRIDEANQ" shown in SEQ ID NO: 74 and/or to SNAP-25$_{197}$, i.e. Neurotoxin (e.g., BoNT/A)-cleaved SNAP-25. More preferably, the monoclonal antibodies of the invention recognize and specifically bind to the epitope SNAP-25$_{191-197}$ "RIDEANQ" shown in SEQ ID NO: 75 and/or to SNAP-25$_{197}$, to the epitope SNAP-25$_{192-197}$ "IDEANQ" of the sequence shown in SEQ ID NO: 76 and/or to SNAP-25$_{197}$, or to the epitope SNAP-25$_{193-197}$ "DEANQ" shown in SEQ ID NO: 77 and/or to SNAP-25$_{197}$.

In one aspect, the present invention relates to an antibody or a fragment thereof, which specifically binds to the cleavage site of the BoNT/A-cleaved SNAP-25 and which comprises a heavy chain variable region (VH) comprising an amino acid sequence shown in SEQ ID NO. 18 and/or a light chain variable region (VL) comprising an amino acid sequence shown in SEQ ID NO. 19. Further encompassed by the invention are antibodies or fragments thereof which comprise one, two or three complementarity determining regions (CDRs) of said heavy chain and/or light chain variable region(s). The corresponding CDRH1. CDRH2 and CDRH3 sequences are shown in SEQ ID NOs. 20 to 22, respectively, whereas the corresponding CDRL1, CDRL2 and CDRL3 sequences are shown in SEQ ID NOs. 23 to 25, respectively. The mentioned sequences correspond to mouse monoclonal antibody 20-2-5 as shown in the following Examples. In addition, the present invention pertains to an antibody or a fragment thereof, which specifically binds to the cleavage site of the BoNT/A-cleaved SNAP-25 and which comprises a heavy chain variable region (VH) comprising an amino acid sequence shown in SEQ ID NO. 26 and/or a light chain variable region (VL) comprising an amino acid sequence shown in SEQ ID NO. 27. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 28 to 30, respectively, whereas the corresponding CDRL1, CDRL2 and CDRL3 sequences are shown in SEQ ID NOs. 31 to 33, respectively. The mentioned sequences correspond to mouse monoclonal antibody 5-10-5 as shown in the following Examples. Further, the present invention relates to an antibody or a fragment thereof, which specifically binds to the cleavage site of the BONT/A-cleaved SNAP-25 and which comprises a heavy chain variable region (VH) comprising an amino acid sequence shown in SEQ ID NO. 34 and/or a light chain variable region (VL) comprising an amino acid sequence shown in SEQ ID NO. 35. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 36 to 38, respectively, whereas the corresponding CDRL1, CDRL2 and CDRL3 sequences are shown in SEQ ID NOs. 39 to 41, respectively. The mentioned sequences correspond to mouse monoclonal antibody 1-10-4 as shown in the following Examples. The present invention pertains also to an antibody or a fragment thereof, which specifically binds to the cleavage site of the BoNT/A-cleaved SNAP-25 and which comprises a heavy chain variable region (VH) comprising an amino acid sequence shown in SEQ ID NO. 42 and/or a light chain variable region (VL) comprising an amino acid sequence shown in SEQ ID NO. 43. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 44 to 46, respectively, whereas the corresponding CDRL1, CDRL2 and CDRL3 sequences are shown in SEQ ID NOs. 47 to 49, respectively. The mentioned sequences correspond to mouse monoclonal antibody 16-5-4 as shown in the following Examples. In addition, the present invention relates to an antibody or a fragment thereof, which specifically binds to the cleavage site of the BoNT/A-cleaved SNAP-25 and which comprises a heavy chain variable region (VH) comprising an amino acid sequence shown in SEQ ID NO. 50 and/or a light chain variable region (VL) comprising an amino acid sequence shown in SEQ ID NO. 51. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 52 to 54, respectively, whereas the corresponding CDRL1, CDRL2 and CDRL3 sequences are shown in SEQ ID NOs. 55 to 57, respectively. The mentioned sequences correspond to mouse monoclonal antibody 6-3-8 as shown in the following Examples. The present invention pertains further to an antibody or a fragment thereof, which specifically binds to the cleavage site of the BONT/A-cleaved SNAP-25 and which comprises a heavy chain variable region (VH) comprising an amino acid sequence shown in SEQ ID NO. 58 and/or a light chain variable region (VL) comprising an amino acid sequence shown in SEQ ID NO. 59. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 60 to 62, respectively, whereas the corresponding CDRL1, CDRL2 and CDRL3 sequences are shown in SEQ ID NOs. 63 to 65, respectively. The mentioned sequences correspond to mouse monoclonal antibody 18-3-3 as shown in the following Examples. Moreover, the present invention concerns an antibody or a fragment thereof, which specifically binds to the cleavage site of the BoNT/A-cleaved SNAP-25 and which comprises a heavy chain variable region (VH) comprising an amino acid sequence shown in SEQ ID NO. 66 and/or a light chain variable region (VL) comprising an amino acid sequence shown in SEQ ID NO. 67. Further encompassed by the invention are antibodies or fragments thereof which comprise one, two or three complementarity determining regions (CDRs) of said heavy chain and/or light chain variable region(s). The corresponding CDRH1, CDRH2 and CDRH3 sequences are shown in SEQ ID NOs. 68 to 70, respectively, whereas the corresponding CDRL1, CDRL2 and CDRL3 sequences are shown in SEQ ID NOs. 71 to 73, respectively. The mentioned sequences correspond to mouse monoclonal antibody 14-12-1 as shown in the following Examples.

The term “first detection antibody” as used herein is an antibody specifically binding to the first capture antibody. Said first detection antibody allows for the specific detection of the first capture antibody. By measuring the amount of bound first detection antibody, the amount of first detection complexes can be determined since the amount of bound first detection antibody in the first detection complex correlates with the amount of first capture antibody (and accordingly the amount of total, i.e. cleaved and non-cleaved Neurotoxin substrate) comprised by the first detection complex. For example, an appropriate species-specific antibody can be used as a first detection antibody: If a mouse antibody has been used as a first capture antibody, said first detection antibody can be an anti-mouse antibody specifically binding to the mouse antibody. The first detection antibody can be, for instance, an alkaline phosphatase (AP)-conjugated antibody, a horseradish-peroxidase (HRP)-conjugated antibody or an antibody conjugated to a fluorescence dye. Conjugation of enzymes to antibodies, for example, by using glutaraldehyde is well known in the art.

Enzyme linked immunosorbent assays (ELISA) have been used to quantitate a wide range of compounds and pathogens for almost 40 years. Initially, radioactivity was used to quantitate the assays, but radioimmunoassays (RIA) have been replaced with assays utilizing enzymes to obtain colorimetric results. Recently new substrates have been developed to produce fluorescent and luminescent products. The basic tenet of the new assays remains the same as colorimetric assays. The substrate is converted into a measurable compound by the enzymatic activity of proteins conjugated to an antibody, which confers specificity.

Commonly used enzyme conjugates in ELISA are alkaline phosphatase or horseradish peroxidase. Accordingly, in one aspect, the first detection antibody can be, for instance, conjugated to alkaline phosphatase or horseradish peroxidase. Further examples of enzyme conjugates which can be used as a first detection antibody in the method of the invention include glucose oxidase which uses glucose as substrate, tyrosinase which converts the substrate 1-(4-Methyl-coumarin-7-yl)-3-(4-hydroxyphenyl)urea) (PAP-AMC) (Stratis Avrameas, Immunochemistry, Volume 6, Issue 1, January 1969, Pages 43-48, IN9-IN11, 49-52) or β-galactosidase which converts the substrate 6,8-difluoro-4-methylumbelliferyl β-d-galactopyranoside(DiFMUG) (Gee et al., Analytical Biochemistry, Volume 273, Issue 1. August 1999, pages 41-48). Upon addition of a substrate, said substrate is converted by the enzyme to a detectable form. For example, alkaline phosphatase catalyzes the cleavage of esters of phosphoric acid. If an alkaline phosphatase (AP)-conjugated antibody is used as a first detection antibody, an appropriate substrate such as a 4-methylumbelliferryl phosphate derivative, e.g., 6,8-Difluoro-4-methylumbelliferyl phosphate (DiFMUP), or fluorescein diphosphate (FDP). 6,8-difluoro-4-methylumbelliferyl phosphate (DiFMUP) is converted by the AP to a detectable form, i.e. the fluorogenic product 6,8-difluoro-4-methylumbelliferone. Said substrate is provided, e.g., by Molecular Probes. Fluorescence intensities of this reaction product of DiFMUP can be measured using excitation/emission maxima of about 358/450 nm. Further substrates which can be used for this purpose are 9H-(1,3-dichloro-9,9-dimethylacridin-2-one-7-yl) phosphate (DDAO-phosphate; Invitrogen), fluorescein diphosphate (FDP; Sigma Aldrich) or 4-methylumbelliferyl phosphate (MUP; Invitrogen). DDAO-phosphate is converted by the AP to the fluorogenic product dimethylacridinone (DDAO), having an excitation/emission maxima of about 646/659 nm. If FDP is used as substrate for the AP, the reaction product is fluorescein, having an excitation/emission maximum of about 490/514 nm. For MUP, the corresponding reaction product is 4-methylumbelliferone (7-hydroxy-4-methylcoumarin), having an excitation/emission maxima of about 360/449 nm. Also these substrates are commercially available, e.g. from Molecular Probes. Alternatively, horseradish peroxidase can be used as enzyme conjugate in the first detection antibody of the method of the invention. Horseradish peroxidase (HRP) catalyzes the reduction of hydrogen peroxide ($H_2O_2$) to water ($H_2O$). In the presence of specific substrates, which act as hydrogen donors, the action of HRP converts colorless or non-fluorescent molecules into colored and/or fluorescent moieties respectively. For instance, Amplex® Red (Life Technologies) is a substrate for use with HRP containing assays. Amplex Red, in the presence of peroxidase enzyme, reacts with $H_2O_2$ in a 1:1 stoichiometry to produce resorufin, a red fluorescent compound which has an absorption and fluorescence emission maxima of 563 nm and 587 nm, respectively. Another example for a HRP substrate is Amplex® UltraRed (Life Technologies). It has been reported that Amplex® UltraRed reagent (excitation/emission of ~570/585 nm) improves upon the performance of the Amplex® Red reagent, offering brighter fluorescence and enhanced sensitivity on a per-mole basis in horseradish peroxidase or horseradish peroxidase-coupled enzyme assays. Fluorescence of the oxidized Amplex® UltraRed reagent (Amplex® UltroxRed reagent) is also less sensitive to pH, and the substrate and its oxidation product exhibit greater stability that the Amplex® Red reagent in the presence of hydrogen peroxide ($H_2O_2$) or thiols such as dithiothreitol (DTT). Further appropriate HRP substrates which can be used in the method of the invention include, e.g., 10-Acetyl-3,7-Dihydroxyphenoxazine (ADHP; AnaSpec) or 3-(4-Hydroxyphenyl) propionic acid (HPPA; AnaSpec) (Tuuminen et al. 1991, J. Immunoassay 12, 29-46).

Alternatively, the first detection antibody can carry an appropriate, detectable label which allows for the detection of the first capture antibody. Labeling may be done by direct or indirect methods. Direct labeling involves binding of the label directly (covalently or non-covalently) to the first detection antibody. Indirect labeling involves binding (covalently or non-covalently) of an agent which specifically binds to the first detection antibody and which carries a detectable label. Such an agent may be, e.g., a secondary (higher order) antibody which specifically binds to the first detection antibody. The secondary antibody in such a case will be coupled to a detectable label. It will be understood that further higher order antibodies can be used in addition for detection of the first detection complex. The higher order antibodies are often used to increase the signal. Suitable higher order antibodies may also include the well-known streptavidin-biotin system (Vector Laboratories, Inc.), and the well-known Dako LSAB™2 and LSAB™+ (labeled streptavidin-biotin), or Dako PAP (Peroxidase Anti-Peroxidase). In a further aspect, the said label of the first detection antibody is a fluorescent dye, i.e. the first antibody is conjugated to a fluorescent dye. In this case, the fluorescence can be directly measured by a fluorescence reader. Typical fluorescent labels include fluorescent proteins such as GFP and its derivatives, Cy dyes such as Cy3, or Cy5, Texas Red, Fluorescein, and the Alexa dyes, e.g. Alexa 568.

The "second detection antibody" as used herein is an antibody specifically binding to the second capture antibody. The second detection antibody can be, for instance, conjugated to an enzyme such as alkaline phosphatase, horseradish peroxidase, glucose oxidase or tyrosinase. Accordingly, in one aspect, the second detection antibody is an alkaline phosphatase (AP)-conjugated antibody, a horseradish-peroxidase (HRP)-conjugated antibody, an glucose oxidase-conjugated antibody or a tyrosinase-conjugated antibody. Said second detection antibody allows for the specific detection of the second capture antibody. By measuring the amount of bound second detection antibody, the amount of second detection complexes can be determined since the amount of bound second detection antibody in the second detection complex correlates with the amount of second capture antibody (and accordingly the amount of cleaved Neurotoxin substrate) comprised by the first detection complex. For example, if a rabbit antibody has been used as a second capture antibody, an anti-rabbit antibody can be used as a second detection antibody. The second detection antibody can carry an enzyme as set forth above or a label such as a fluorescent dye (i.e. the second detection antibody is conjugated to a fluorescent dye) as mentioned elsewhere herein with respect to the first detection antibody. In one aspect of the method of the invention, the enzyme conjugated to the first detection antibody differs from the enzyme conjugated to the second detection antibody in order to allow the specific detection of the respective first and second capture antibody in the method of the invention. For instance, if the first detection antibody is an AP-conjugated antibody, the second detection antibody can be a horseradish peroxidase (HRP)-conjugated antibody or vice versa. Further, the excitation/emission spectra of the fluorogenic substrates of the AP and HRP do not substantially overlap but differ from each other, i.e. they show a clear shift so as to allow the distinction of the fluorescence intensities generated by the respective product. For example, DiFMUP exhibits excitation/emission at ~358/450 nm, whereas Amplex UltraRed exhibits excitation/emission of ~570/585 nm, thereby allowing for accurate measurements of the fluorescence intensities generated by the conversion of said fluorogenic substrates by the respective enzyme. In a further aspect, the alkaline phosphatase (AP)-conjugated antibody is used as a first detection antibody for the antigen which is present in excess in the cell, i.e. for the measurement of the amount of the total (non-cleaved and cleaved) Neurotoxin substrate, such as total SNAP-25, in the cell. The horseradish peroxidase (HRP)-conjugated antibody is used as a second detection antibody for the antigen which is present in the cell in a lower amount, i.e. for the measurement of the amount of the cleaved Neurotoxin substrate, such as BoNT/A cleaved SNAP-25, in the cell. As known in the art, HRP substrates are more sensitive than AP substrates meaning that lower amounts of analytes can be detected. If an HRP antibody is used as secondary antibody for the detection of cleaved SNAP-25, lower amounts of cleaved SNAP-25 are detectable. In turn, lower amounts of BoNT/A can be determined, thereby increasing the sensitivity of the assay. Because the AP antibody measures the total amount of SNAP-25 in the cell, high sensitivity for the substrate is not required, due to the excess of analyte.

The term "at least" as used herein such as, for example, "at least a first capture antibody" means that in addition to an antibody specifically binding to the non-cleaved and Neurotoxin-cleaved substrate, one or more further antibodies with the mentioned specificity can be used in the method of the invention. Similarly, "at least a second capture antibody" means that in addition to an antibody specifically binding to the cleavage site of the Neurotoxin-cleaved substrate, one or more further antibodies with the mentioned specificity can be used in the method of the invention. Further, one or more first detection antibodies specifically binding to the first detection antibody (or first detection antibodies) can be used in the method of the invention. Similarly, one or more second detection antibodies specifically binding to the second detection antibody (or second detection antibodies) can be used in the method of the invention.

The term "first detection complex" refers to a complex comprising a first capture antibody and a first detection antibody which specifically binds to the non-cleaved and Neurotoxin-cleaved substrate, thereby allowing for the determination of the total content of Neurotoxin substrate in the cell. The amount of first detection complex can be measured by determination of the amount of specifically bound first detection antibody. This can be achieved dependent on the nature of the enzyme or the label of the first detection antibody, e.g. by measuring the intensity of fluorescence.

The term "second detection complex" refers to a complex comprising the second capture antibody and the second detection antibody which specifically binds to the cleavage site of the Neurotoxin-cleaved substrate, thereby allowing for the determination of the content of cleaved Neurotoxin substrate in the cell. The amount of second detection complex can be measured by determination of the amount of specifically bound second detection antibody. This can be achieved dependent on the nature of the enzyme or the label of the second detection antibody, e.g. by measuring the intensity of fluorescence.

It is envisioned that instead of enzyme-linked immunosorbent analysis (ELISA), any detection system can be used to practice aspects of the method of the invention, with the provision that the signal to noise ratio can distinguish to a statistically significant degree the signal from the formed antibody-antigen complexes from the background signal. Non-limiting examples of immuno-based detection systems include immunoblot analysis, like Western blotting and dot-blotting, immunoprecipitation analysis, and sandwich ELISA. The detection of the signal can be achieved using autoradiography with imaging or phosphorimaging (AU), bioluminescence (BL), fluorescence, resonance energy transfer, plane polarization, colormetric, or flow cytometry (FC). Descriptions of immuno-based detection systems are disclosed, for example, in Commonly Used Techniques in Molecular Cloning, pp. A8.1-A8-55 (Sambrook & Russell, eds., Molecular Cloning A Laboratory Manual, Vol. 3, 3.sup.rd ed. 2001); Detection Systems, pp. A9.1-A9-49 (Sambrook & Russell, eds., Molecular Cloning A Laboratory Manual, Vol. 3, 3.sup.rd ed. 2001).

In a further aspect, the cells, antibodies, Neurotoxin polypeptides and Neurotoxin substrates or any other product as referred to herein are isolated cells, antibodies, Neurotoxin polypeptides, Neurotoxin substrates or products, respectively. As used herein, the term "isolated" such as an isolated antibody refers to a molecule separated from its natural environment by the use of human intervention.

In one aspect of the method of the invention, the method is a fluorescence method.

In another aspect of the method of the invention, the Neurotoxin polypeptide is a BONT/A, BONT/B, BoNT/C1, BONT/D, BONT/E, BoNT/F or BoNT/G polypeptide or a Tetanus (TeNT) Neurotoxin polypeptide, as defined in detail elsewhere herein.

In a further aspect of the method of the invention, the Neurotoxin substrate is VAMP/Synaptobrevin, SNAP-25 or Syntaxin.

In the following, the corresponding accession number of the respective Neurotoxin substrate which can be used in the method of the invention is indicated: human SNAP-25 P60880, human Syntaxin-1A Q16623, Syntaxin-1B P61266, Syntaxin-2 P32856, Syntaxin-3 Q13277, Syntaxin-4 Q12846, Syntaxin-5 Q13190, Syntaxin-6 043752, Syntaxin-7 O15400, Syntaxin-8 Q9UNK0, Syntaxin-10 060499, Syntaxin-11 075558, Syntaxin-12 Q86Y82, Syntaxin-16 O14662, Syntaxin-17 P56962, Syntaxin-18 Q9P2W9, Syntaxin-19 Q8N4C7; human Synaptobrevin-1 P23763, Synaptobrevin-2 P63027, Synaptobrevin-3 Q15836; human synaptotagmin: Synaptotagmin-1 P21579, Synaptotagmin-2 Q8N910, Synaptotagmin-3 Q9BQG1, Synaptotagmin-4 Q9H2B2, Synaptotagmin-5 000445, Synaptotagmin-6 Q5T7P8, Synaptotagmin-8 Q8NBV8, Synaptotagmin-9 Q86SS6, Synaptotagmin-10 Q6XYQ8, Synaptotagmin-11 Q9BT88, Synaptotagmin-12 Q8IV01, Synaptotagmin-13 Q7L8C5, Synaptotagmin-14 Q8NB59, Synaptotagmin-15 Q9BQS2, Synaptotagmin-16 Q17RD7, Synaptotagmin-17 Q9BSW7, human vesicle associated membrane proteins (VAMPs): Vesicle-associated membrane protein 1 P23763, Vesicle-associated membrane protein 2 P63027, Vesicle-associated membrane protein 3 Q15836, Vesicle-associated membrane protein 4 075379, Vesicle-associated membrane protein 5 095183, Vesicle-associated membrane protein 7 P51809, Vesicle-associated membrane protein 8 Q9BV40; of synaptic vesicle glycoproteins (SV2): Synaptic vesicle glycoprotein 2A Q7L0J3, Synaptic vesicle glycoprotein 2B Q7L112, Synaptic vesicle glycoprotein 2C.

In another aspect of the invention, the cells are neuronal cells or neuronal differentiated cells selected from the group consisting of: primary neuronal cells, tumor cells which are capable of differentiating to neuronal cells such as neuroblastoma cells or cell lines as defined elsewhere herein, P19 cells or induced pluripotent stem cell (iPS)-derived neurons, preferably human induced pluripotent stem cell (iPS)-derived neurons.

In a further aspect of the method of the invention, fixing the cells is carried out by the addition of a fixation agent selected from the group consisting of: methanol, ethanol, acetone, formaldehyde or mixtures thereof. Preferably, fixing the cells is carried out by addition of ice-cold methanol (−20° C.) and incubation for about 20 minutes at −20° C.

In one aspect of the method of the invention, the first capture antibody specifically binding to the non-cleaved and Neurotoxin-cleaved substrate allows for the determination of the total amount of the Neurotoxin substrate in the cells. Suitable binding regions and epitopes of the first capture antibody within the respective Neurotoxin substrate(s) have been defined elsewhere herein.

In specific aspects of the method of the invention, the first capture antibody specifically binding to the non-cleaved and Neurotoxin-cleaved substrate is the rabbit polyclonal anti-SNAP-25 antibody S9684, the rabbit polyclonal anit-SNAP25 antibody PA5-19708 (Pierce Antibodies), or the rabbit polyclonal anti-SNAP25 antibody PA5-19701 (Pierce Antibodies).

In further aspects of the method of the invention, the second capture antibody is the mouse monoclonal antibody 20-2-5, 5-10-5, 1-10-4, 16-5-4, 6-3-8, 18-3-3, or 14-12-1 of the invention, or the mouse monoclonal antibody clone MC-6053 (R&D Systems). Preferably, the second capture antibody is the mouse monoclonal antibody 20-2-5. The corresponding sequences of the variable regions and the CDRs of the mouse monoclonal antibodies of the invention have been described elsewhere herein.

In specific aspects of the method of the invention, the first and/or second capture antibody is/are immobilized. For example, said first and/or second capture antibody is/are linked to a solid phase support. As used herein, the term "solid-phase support" is synonymous with "solid phase" and refers to any matrix that can be used for immobilizing a first and/or second capture antibody disclosed in the present specification. Non-limiting examples of solid phase supports include, e.g., a tube; a plate; a column; pins or "dipsticks"; a magnetic particle, a bead or other spherical or fibrous chromatographic media, such as, e.g., agarose, sepharose, silica and plastic; and sheets or membranes, such as, e.g., nitrocellulose and polyvinylidene fluoride (PVDF). The solid phase support can be constructed using a wide variety of materials such as, e.g., glass, carbon, polystyrene, polyvinylchloride, polypropylene, polyethylene, dextran, nylon, diazocellulose, or starch. The solid phase support selected can have a physical property that renders it readily separable from soluble or unbound material and generally allows unbound materials, such as, e.g., excess reagents, reaction by-products, or solvents, to be separated or otherwise removed (by, e.g., washing, filtration, centrifugation, etc.) from solid phase support-bound assay component. Non-limiting examples of how to make and use a solid phase supports are described in, e.g., Molecular Cloning, A Laboratory Manual, supra, (2001); and Current Protocols in Molecular Biology, supra, (2004), each of which is hereby incorporated by reference in its entirety. In one aspect, the first and/or second capture antibody is conjugated to beads. It is envisaged that the antibody-bead conjugates are small enough to be able to enter the cells through the pores caused by the permeabilization of said cells.

In specific aspects of the method of the invention, the first detection antibody is an alkaline phosphatase(AP)-conjugated antibody, a horseradish-peroxidase (HRP)-conjugated antibody or an antibody conjugated to a fluorescence dye.

In further specific aspects of the method of the invention, the second detection antibody is an alkaline phosphatase (AP)-conjugated antibody, a horseradish-peroxidase (HRP)-conjugated antibody, a glucose oxidase-conjugated antibody, a tyrosinase-conjugated antibody or a β-Galactosidase-conjugated antibody.

Preferably, the alkaline phosphatase (AP)-conjugated antibody is used as a first detection antibody for the measurement of the amount of the total (non-cleaved and cleaved) Neurotoxin substrate, such as total SNAP-25, in the cell; and the horseradish peroxidase (HRP)-conjugated antibody is used as a second detection antibody for the measurement of the amount of the cleaved Neurotoxin substrate, such as BoNT/A cleaved SNAP-25, in the cell.

In certain aspects of the method of the invention, the AP substrate is a 4-methylumbelliferryl phosphate derivative such as 6,8-Difluoro-4-methylumbelliferyl phosphate (DiFMUP), or fluorescein diphosphate (FDP).

In specific aspects of the method of the invention, the HRP substrate is Amplex UltraRed, 10-Acetyl-3,7-Dihydroxyphenoxazine (ADHP) or 3-(4-Hydroxyphenyl) propionic acid (HPPA).

In a more specific aspect of the method of the invention, the method is carried out as illustrated in FIG. 1.

The invention in a further aspect relates to a kit for carrying out the method of the invention comprising:
a) an arrangement of a first capture antibody, a second capture antibody, a first detection antibody and a second detection antibody, wherein said arrangement allows for carrying out the method of the invention;
b) means for calculating the amount of substrate cleaved by said Neurotoxin based on the amounts of the first and second detection complexes determined by the arrangement according to a); and
c) instructions for carrying out said method.

The term "kit" as used herein refers to a collection of the aforementioned means or reagents of the present invention which may or may not be packaged together. The components of the kit may be comprised by separate vials (i.e. as a kit of separate parts) or provided in a single vial. Moreover, itis to be understood that the kit of the present invention is to be used for practicing the methods referred to herein above. In one aspect, it is envisaged that all components are provided in a ready-to-use manner for practicing the method referred to herein. In a further aspect, the kit contains instructions for carrying out the said method. The instructions can be provided by a user manual in paper- or electronic form. For example, the manual may comprise instructions for interpreting the results obtained when carrying out the aforementioned methods using the kit of the present invention.

Finally, the invention relates in another aspect to a method for manufacture of a formulated Neurotoxin product for use in pharmaceutical or cosmetic applications, comprising (i) determining the biological activity of a Neurotoxin product by the method of the invention and (ii) formulating the Neurotoxin product for use in pharmaceutical or cosmetic applications. The Neurotoxin product can be formulated by various techniques dependent on the desired application purposes which are known in the art. For example, the (biologically active) Neurotoxin product can be used in combination with one or more pharmaceutically acceptable carriers as a pharmaceutical composition. The pharmaceutically acceptable carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatine, agar, pectin, acacia, magnesium stearate, stearic acid and the like. Exemplary of liquid carriers are glycerol, phosphate buffered saline solution, water, emulsions, various types of wetting agents, and the like. Suitable carriers comprise those mentioned above and others well known in the art, see, e.g., Remington's Pharmaceutical Sciences, Mack Publishing Company, Easton, Pennsylvania. In an aspect, the pharmaceutical composition can be dissolved in a diluent, prior to administration. The diluent is also selected so as not to affect the biological activity of the Neurotoxin product. Examples of such diluents are distilled water or physiological saline. In addition, the pharmaceutical composition or formulation may also include other carriers or non-toxic, non-therapeutic, non-immunogenic stabilizers and the like. Thus, the formulated Neurotoxin product can be present, in an aspect, in liquid or lyophilized form. In an aspect, it can be present together with glycerol, protein stabilizers (HSA) or non-protein stabilizers such as polyvinyl pyrrolidone (PVP), hyaluronic acid or free amino acids. In an aspect, suitable non-proteinaceous stabilizers are disclosed in WO 2005/007185 or WO 2006/020208. In one aspect, the biological activity determined according to step (i) by the method of the invention corresponds to an Botulinum toxin activity of 25, 50, 75, 100, 125, 150 or 200 U (Mouse LD50 units). The formulated Neurotoxin product may be used for human or animal therapy of various diseases or disorders in a therapeutically effective dose or for cosmetic purposes.

The disease or disorder as referred to herein is selected from the group consisting of voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxical jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitant mutational dysphonia, upper oesophageal sphincter dysfunction, vocal fold granuloma, stuttering Gilles de la Tourette syndrome, middle ear myoclonus, protectivelarynxclosure, postlaryngectomy, speechfailure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinson's, in amyotrophic lateral sclerosis, spastic conditions, in encephalitis and myelitis autoimmuneprocesses, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, myelon tumor and vaginism. A cosmetic use is selected from treatment or reduction of wrinkles like crow's feet or GFL, frowning, facial asymmetries.

All references cited in this specification are herewith incorporated by reference with respect to their entire disclosure content and the disclosure content specifically mentioned in this specification.

BRIEF DESCRIPTION OF THE DRAWINGS

Figure 1:
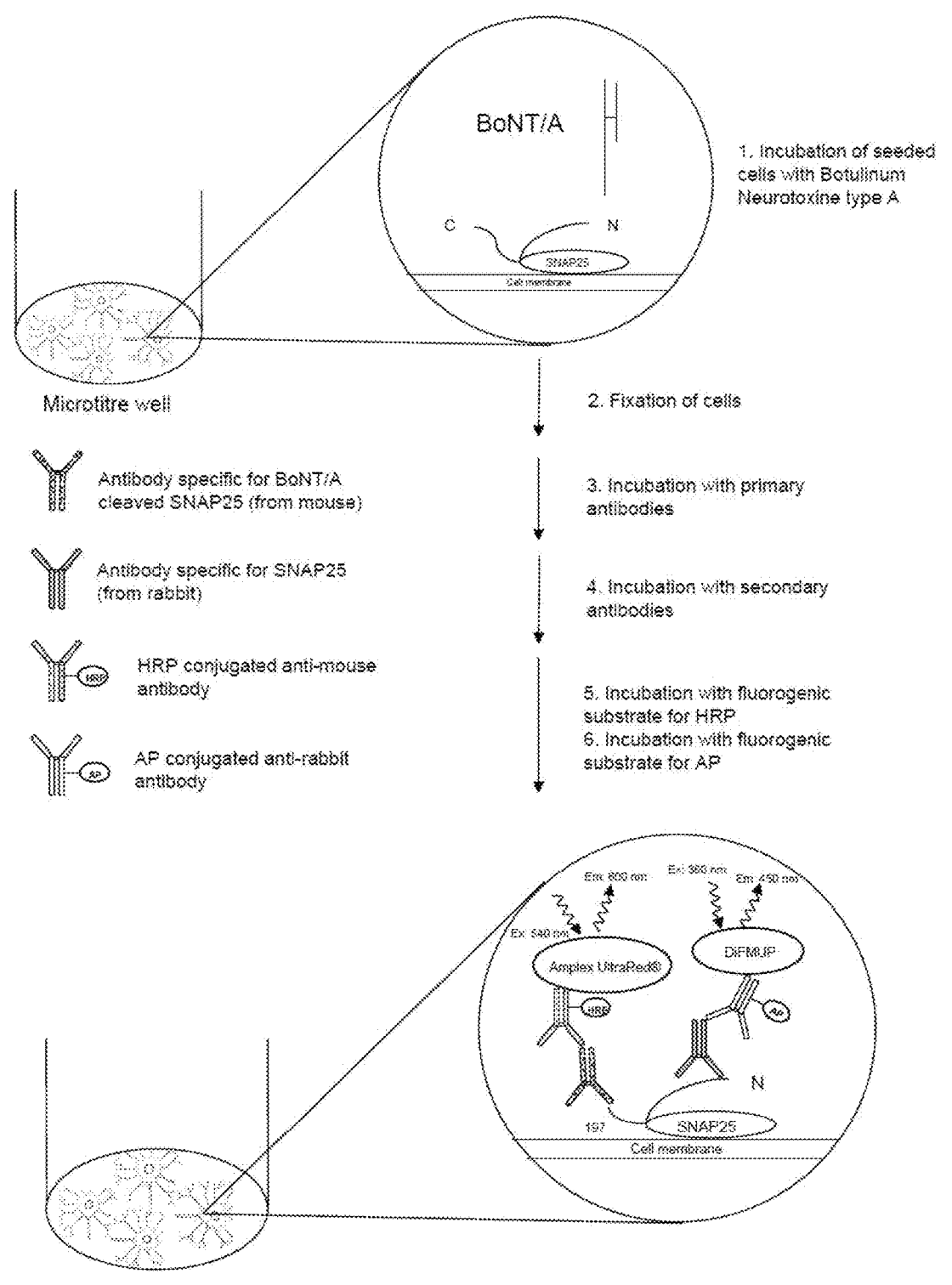

FIG. 1: Diagram representing the mode of action of the cell-based assay of the invention. Cells susceptible to Neurotoxin intoxication are seeded in multiwell plates, Thereafter, the cells are intoxicated with Neurotoxin polypeptide and after a given intoxication period the cells are fixated. The specific antibody for Neurotoxin-cleaved SNAP-25 and the specific antibody for un-cleaved SNAP-25 bind to the specific binding sites on SNAP-25. Using enzyme-coupled anti-host specific secondary antibodies, these binding events can be used to generate measurable signals which correlate with the concentration of neurotoxin cleaved SNAP-25 and the total amount of SNAP-25 within the well. With increasing BoNT/A concentration the amount of measured cleaved SNAP-25 increases resulting in a gain of signal.

FIG. 2: The two graphs represent the resulting BoNT/A calibration curves for iPS-derived neurons and SiMa cells according to Example 2. They show the dependency between respectively the concentration and activity of BoNT/A and the determined fluorescence signal (RFU) for the HRP substrate and the content of BoNT/A-cleaved SNAP-25 normalized to the total amount of SNAP-25 within the well. Upon increasing concentration and activity, respectively, of BoNT/A, more SNAP-25 is converted by the Neurotoxin, resulting in an increase in the content of cleaved SNAP-25.

FIG. 3: The graph represents the resulting BoNT/A calibration curve for iPS derived neurons according to Example 4. It shows the dependency between respectively the concentration and activity of BoNT/A and the determined fluorescence signal (RFU) for the HRP substrate and the content of BoNT/A-cleaved SNAP-25 and the content of BoNT/A-cleaved SNAP-25 normalized to the total amount of SNAP-25 within the well. Upon increasing concentration and activity, respectively, of BoNT/A, more SNAP-25 is converted by the Neurotoxin, resulting in an increase in the content of cleaved SNAP-25.

The invention will now be illustrated by the following examples which shall, however, not be construed as limiting the scope of the present invention.

EXAMPLE 1: GENERATION OF MONOCLONAL ANTIBODIES SPECIFICALLY BINDING TO THE CLEAVAGE SITE OF THE NEUROTOXIN-CLEAVED SUBSTRATE SNAP-25

Mouse monoclonal antibodies specifically binding to the cleavage site of the Neurotoxin-cleaved substrate SNAP-25 have been generated using the hybridoma standard technique. To this end, Balb/c mice (female, 8 weeks) have been immunized with SNAP-$25_{190-197}$ with a Cysteine residue at the N-terminus, "C-TRIDEANQ" (SEQ ID NO: 17). Said N-terminal Cysteine residue is not derived from the SNAP-25 amino acid sequence but has been introduced for linking the SNAP-$25_{190-197}$ peptide (SEQ ID NO: 74) to the keyhole limpet hemocyanin (KLH). Hybridoma cells have been obtained by the fusion of mouse spleen cells with the myeloma cell line SP2/0-Ag14 (SP2/0) purchased from the German Collection of Microorganisms and Cell Culture (DSMZ GmbH, Braunschweig, ACC 146); see also Hemmerlein et al., Molecular Cancer 2006, 5, 41. Antibodies specifically binding to the cleavage site of the Neurotoxin-cleaved substrate SNAP-25 were screened in ELISA. The obtained clones have been selected with respect to their specificity and affinity to BoNT/A-cleaved SNAP-25. As a negative control, the clones have been tested for their non-binding to non-cleaved SNAP-$25_{206}$. As a result, the mouse monoclonal antibodies 20-2-5, 5-10-5, 1-10-4, 16-5-4, 6-3-8, 18-3-3, and 14-12-1 were found to be highly specific for BoNT/A-cleaved SNAP-$25_{197}$, with no detectable cross-reactivity to SNAP25$_{206}$ in ELISA and Western blots. Isotyping of said monoclonal antibodies has been carried out using the mouse monoclonal antibody isotyping test kit (Serotec). As a result it has been found that mAb 20-2-5, 14-12-1, 6-3-8, and 5-10-5 are IgG1 antibodies, whereas mAb 18-3-3, 16-5-4, and 1-10-4 are IgG2a antibodies.

The corresponding amino acid sequences of the VH and VL chains and the corresponding CDR (complementarity determining region) sequences of the mentioned mouse monoclonal antibodies are indicated in the sequence listing.

EXAMPLE 2: DOUBLE-FLUORESCENCE-CB-BONT/A ACTIVITY ELISA

Fixation of Cells
1. Remove the media/toxin solution. Add 100 µl/well ice-cold methanol (−20° C.) and incubate for 20 min at −20° C.

Note: Perform all subsequent steps at room temperature.

After Cell Fixation:

1. Remove the methanol solution and add 100 µl/well PBS buffer. For longer storage (>1 day) one should add 300 µl//well PBS buffer and seal the plates with parafilm. The plates should be stored in the refrigerator.
2. Remove the PBS buffer and wash the cells 3 times with 200 µl/well of wash buffer. Each step should be performed for 1 minute with gentle shaking.
3. Remove the wash buffer and add 100 µl/well of quenching buffer and incubate for 20 minutes with gentle shaking.
4. Remove the quenching buffer and wash the cells once with 300 µl/well of wash buffer for 5 minutes under gentle shaking.
5. Remove the wash buffer, and add 200 µl/well of blocking buffer and incubate for 1 hour with gentle shaking.
6. Remove the blocking buffer, and add 100 µl/well permeabilization buffer and incubate for 15 minutes with gentle shaking.
7. Remove the permeabilization buffer and wash the cells once with 300 µl/well of PBS buffer. This step should be performed for 1 minute with gentle shaking.
8. Remove the PBS buffer and add 100 µl of the primary antibody mixture (antibody dilution in blocking buffer) to each well. Incubate overnight (16-18 h) with gentle shaking. The cells are simultaneously incubated with two primary antibodies: a mouse antibody specific for the BoNT/A-cleaved SNAP-25 and a polyclonal rabbit antibody that recognizes SNAP-25 (antibody for determining the total amount of SNAP-25 for normalization).
9. Remove the primary antibody mixture and wash the cells 4 times with 200 µl of wash buffer. Each step should be performed for 5 minutes with gentle shaking.
10. Remove the wash buffer, and add 100 µl of the secondary antibody mixture: HRP-conjugated anti-mouse and AP-conjugated anti-rabbit secondary antibodies (antibody dilution in blocking buffer) to each well and incubate for 2.5-3 hours with gentle shaking.
11. Remove the secondary antibody mixture and wash the cells 5 times with 200 µl/well of wash buffer, followed by 1 washing step with 300 µl/well of HEPES buffer. Each wash step should be performed for 5 minutes with gentle shaking.
12. Remove the PBS buffer from the plate and add 75 µl of a fluorogenic substrate for horseradish-peroxidase (HRP substrate) to each well. Incubate for 50 minutes with gentle shaking. Protect the plates from direct light.
13. Add 75 µl of a fluorogenic substrate for alkaline phosphatase (AP substrate) to each well and incubate for an additional 50 minutes at with gentle shaking. Protect the plates from direct light.
14. Read the plates using a fluorescence plate reader:

excitation at 540 nm; emission at 600 nm.excitation at 360 nm; emission at 450 nm.

15. Calculation

For normalization, the RFU value for cleaved SNAP-25 (fluorescence at 600 nm) is normalized to RFU of total SNAP-25 (450 nm) in each well. For better illustration of RFUs in a diagram all values are multiplied with a factor 1000 using the following equation:

$$RFU\ (600\ \text{nm}) RFU\ (450\ \text{nm}) \times 1000$$

Subsequently the resulting RFU values are averaged for each standard or sample.

Reagent Preparation

Wash Buffer:

0.1% Triton X-100 in 10 mM PBS buffer (pH 7.4)

PBS Buffer (10 mM):

Phosphate buffered saline (Sigma, #P5368) (pH 7.4)

Quenching Buffer:

0.6% $H_2O_2$ in 10 mM PBS buffer (pH 7.4)

Blocking Buffer:

2% BSA in 10 mM PBS buffer (pH 7.4)+0.05% Triton X-100

Permeabilization Buffer:

0.5% Triton X-100 in 10 mM PBS buffer

HEPES Buffer:

50 mM HEPES (pH 7.4)

HRP Substrate:

50 mM HEPES (pH 7.4)

0.007% $H_2O_2$ 150 pM Amplex UltraRed

AP Substrate:

25 mM Diethanolamine (pH 9.8)

2 mM $MgCl_2$

100 µl M DiFMUP

EXAMPLE 3: ILLUSTRATION OF BONT/A CALIBRATION CURVES IN THE CBA-ELISA ACCORDING TO EXAMPLE 2 OF THE PRESENT INVENTION

Cell culture and intoxication with BoNT/A of parental SiMa cells has been carried out according to the provider's manual. Similarly, cell culture and intoxication with BoNT/A of human induced pluripotent stem (iPS)cell-derived neurons (Cellular Dynamics) has been carried out according to the protocol by the manufacturer.

The ELISA has been carried out according to Example 2. As first capture antibody specifically binding to the non-cleaved and BoNT/A-cleaved SNAP-25, the rabbit polyclonal anti-SNAP-25 antibody S9684 (Sigma) has been used. This antibody allows for the detection of the total amount of SNAP-25 within the cells. As a second capture antibody specifically binding to the cleavage site of the BoNT/A-cleaved SNAP-25, the monoclonal antibody clone 20-2-5 of the invention (see Example 1) has been utilized.

Figure 2:
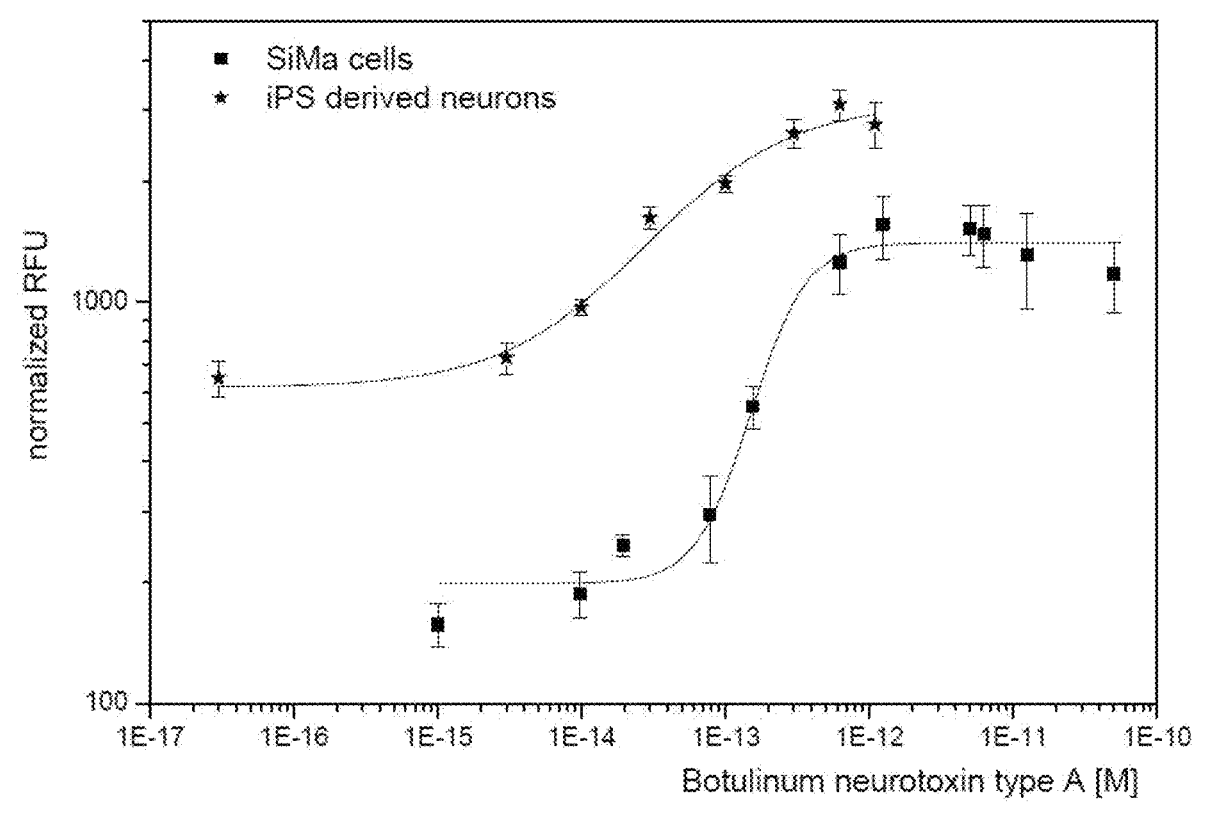

The two graphs in FIG. 2 show the obtained BoNT/A calibration curves. They demonstrate the dependency between respectively the concentration and activity of BoNT/A and the determined fluorescence signal (RFU) for the HRP substrate and the content of BoNT/A-cleaved SNAP-25 (RFU values are not blank-corrected in order to illustrate the errors of the single BoNT/A standards). Upon increasing concentration and activity, respectively, of BoNT/A, more SNAP-25 is converted by the Neurotoxin resulting in an increase in the content of cleaved SNAP-25. The dependency of the signal of the BoNT/A concentration/activity of BoNT/A is illustrated by using a 4-parameter equation.

EXAMPLE 4: DOUBLE-FLUORESCENCE-CB-BONT/A ACTIVITY ELISA

Fixation of Cells
1. Remove the media/toxin solution. Add 100 µl/well ice-cold methanol (−20° C.) and incubate for 20 min at −20° C.

Note: Perform all subsequent steps at room temperature.

After Cell Fixation:
1. Remove the methanol solution and add 100 µl/well PBS buffer. For longer storage (>1 day) one should add 300 µl//well PBS buffer and seal the plates with parafilm. The plates should be stored in the refrigerator.
2. Remove the PBS buffer and wash the cells 3 times with 200 µl/well of PBS buffer. Each step should be performed for 1 minute with gentle shaking.
3. Remove the PBS buffer and add 100 µl/well of quenching buffer and incubate for 20 minutes with gentle shaking.
4. Remove the quenching buffer and wash the cells once with 300 µl/well of PBS buffer for 3 minutes under gentle shaking.
5. Remove the PBS buffer, and add 200 µl/well of blocking buffer and incubate for 1 hour with gentle shaking.
6. Remove the blocking buffer and add 100 µl of the primary antibody mixture (antibody dilution in blocking buffer) to each well. Incubate overnight (16-18 h) with gentle shaking. The cells are simultaneously incubated with two primary antibodies: a mouse antibody specific for the BoNT/A-cleaved SNAP-25 and a polyclonal rabbit antibody that recognizes SNAP-25 (antibody for determining the total amount of SNAP-25 for normalization).
7. Remove the primary antibody mixture and wash the cells 4 times with 200 µl of PBS buffer. Each step should be performed for 3 minutes with gentle shaking.
8. Remove the PBS buffer, and add 100 µl of the secondary antibody mixture: HRP-conjugated anti-mouse and AP-conjugated anti-rabbit secondary antibodies (antibody dilution in blocking buffer) to each well and incubate for 2.5-3 hours with gentle shaking.
9. Remove the secondary antibody mixture and wash the cells 5 times with 200 µl/well of PBS buffer, followed by 1 washing step with 300 µl/well of HEPES buffer. Each wash step should be performed for 3 minutes with gentle shaking.
10. Remove the HEPES buffer from the plate and add 75 µl of a fluorogenic substrate for horseradish-peroxidase (HRP substrate) to each well. Incubate for 50 minutes with gentle shaking. Protect the plates from direct light.
11. Add 75 µl of a fluorogenic substrate for alkaline phosphatase (AP substrate) to each well and incubate for an additional 50 minutes at with gentle shaking. Protect the plates from direct light.
12. Read the plates using a fluorescence plate reader: excitation at 540 nm; emission at 600 nm. excitation at 360 nm; emission at 450 nm.
13. Calculation For normalization, the RFU value for cleaved SNAP-25 (fluorescence at 600 nm) is normalized to RFU of total SNAP-25 (450 nm) in each well. For better illustration of RFUs in a diagram all values are multiplied with a factor 1000 using the following equation:

$$RFU\ (600\ nm) RFU\ (450\ nm) \times 1000$$

Subsequently the resulting RFU values are averaged for each standard or sample.

Reagent Preparation

PBS Buffer (10 mM):
  Phosphate buffered saline (Sigma, #P5368) (pH 7.4)

Quenching Buffer:
  1.6% $H_2O_2$ in 10 mM PBS buffer (pH 7.4)

Blocking Buffer:
  2% BSA in 10 mM PBS buffer (pH 7.4)+0.05% Triton X-100

HEPES Buffer:
  50 mM HEPES (pH 7.4)

HRP Substrate:
  50 mM HEPES (pH 7.4)
  1.7 7% $H_2O_2$
  150 pM Amplex UltraRed AP Substrate:
  25 mM Diethanolamine (pH 9.8)
  2 mM $MgCl_2$
  100 µl M DiFMUP

EXAMPLE 5: ILLUSTRATION OF BONT/A CALIBRATION CURVES IN THE CBA-ELISA ACCORDING TO EXAMPLE 4 OF THE PRESENT INVENTION

Cell culture and intoxication with BoNT/A of human induced pluripotent stem (iPS) cell-derived neurons (Cellular Dynamics) has been carried out according to the protocol by the manufacturer.

The ELISA has been carried out according to Example 4. As first capture antibody specifically binding to the non-cleaved and BoNT/A-cleaved SNAP-25, the rabbit polyclonal anti-SNAP-25 antibody S9684 (Sigma) has been used. This antibody allows for the detection of the total amount of SNAP-25 within the cells. As a second capture antibody specifically binding to the cleavage site of the BoNT/A-cleaved SNAP-25, the monoclonal antibody clone 20-2-5 of the invention (see Example 1) has been utilized.

Figure 3:
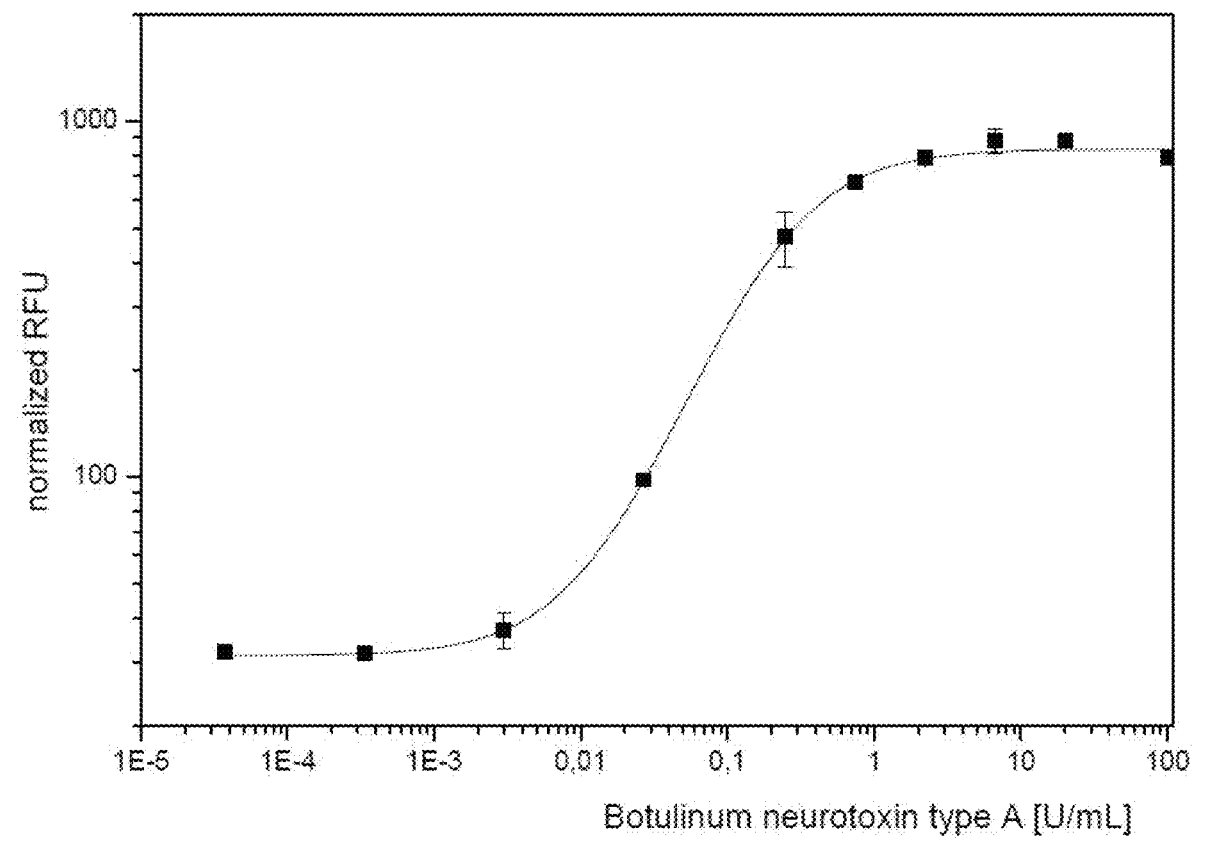

The graph shown in FIG. 3 represents the obtained BoNT/A calibration curve. It shows the dependency between respectively the concentration and activity of BoNT/A and the determined fluorescence signal (RFU) for the HRP substrate and the content of BoNT/A-cleaved SNAP-25. Upon increasing concentration and activity, respectively, of BoNT/A, more SNAP-25 is converted by the Neurotoxin resulting in an increase in the content of cleaved SNAP-25. The dependency of the signal of the BoNT/A concentration/activity of BoNT/A is illustrated by using a 4-parameter equation.

SEQUENCE LISTING

```
Sequence total quantity: 77
SEQ ID NO: 1              moltype = DNA   length = 3891
FEATURE                   Location/Qualifiers
source                    1..3891
                          mol_type = other DNA
                          organism = Clostridium botulinum
SEQUENCE: 1
atgccatttg ttaataaaca atttaattat aaagatcctg taaatggtgt tgatattgct    60
tatataaaaa ttccaaatgc aggacaaatg caaccagtaa aagcttttaa aattcataat   120
aaaatatggg ttattccaga aagagataca tttacaaatc ctgaagaagg agatttaaat   180
ccaccaccag aagcaaaaca agttccagtt tcatattatg attcaacata tttaagtaca   240
gataatgaaa aagataatta tttaaaggga gttacaaaat tatttgagag aatttattca   300
actgatcttg aagaatgtt gttaacatca atagtaaggg gaataccatt ttggggtgga   360
agtacaaatag atacagaatt aaaagttatt gatactaatt gtattaatgt gatacaacca   420
gatggtagtt atagatcaga agaacttaat ctagtaataa taggacccctc agctgatatt   480
atacagtttg aatgtaaaag ctttggacat gaagttttga atcttacgcg aaatggttat   540
ggctctactc aatacattag atttagccca gattttacat ttggttttga ggagtcactt   600
gaagttgata caaatcctct tttaggtgca ggcaaatttg ctacgatcc agcagtaaca   660
ttagcacatg aacttataca tgctggacat agattataga gaatagcaat taatccaaat   720
agggttttta aagtaaatac taatgcctat tatgaaatga gtgggttaga agtaagcttt   780
gaggaactta aacatttgg gggacatgat gcaaagttta tagatagttt acaggaaaac   840
gaatttcgtc tatattatta taataagttt aaagatatag caagtacact taataaagct   900
aaatcaatag taggtactac tgcttcatta cagtatatga aaatgttttt taaagagaaa   960
tatctcctat ctgaagatac atctggaaaa ttttcggtag ataaattaaa atttgataag  1020
ttatacaaaa tgttaacaga gatttacaca gaggataatt ttgttaagtt ttttaaagta  1080
cttaacagaa aaacatattt gaattttgat aaagccgtat ttaagataaa tatagtacct  1140
aaggtaaatt acacaatata tgatggattt aatttaagaa atacaaattt agcagcaaac  1200
tttaatggtc aaaatacaga aattaatat atgaattta ctaaactaaa aaatttact    1260
ggattgtttg aatttatta gttgctatgt gtaagaggga taataacttc taaaactaaa  1320
tcattagata aaggatacaa taaggcatta atgatttat gtatcaaagt taataattgg  1380
gacttgtttt ttagtccttc agaagataat tttactaatg atctaaataa aggagaagaa  1440
attacatctg atactaatat agaagcagca gaagaaaata ttagtttaga tttaatacaa  1500
caatattatt taacctttaa ttttgataat gaacctgaaa atatttcaat agaaaatctt  1560
tcaagtgaca ttataggcca attagaactt atgcctaata tagaaagatt tcctaatgga  1620
aaaagtatg agttagataa atatactatg ttccattatc ttcgtgctca agaatttgaa  1680
catggtaaat ctaggattgc tttaacaaat tctgttaacg aagcattatt aaatcctagt  1740
cgtgttata catttttttc ttcagactat gtaaagaaag ttaataaagc tacggaggca  1800
gctatgtttt taggctgggt agaacaatta gtatatgatt ttaccgatga aactagcgaa  1860
gtaagtacta cggataaaat tgcggatata actataatta ttccatatat aggacctgct  1920
ttaaatatag gtaatatgtt atataaagat gatttgtag gtgctttaat attttcagga  1980
gctgttattc tgttagaatt tataccagag attgcaatac ctgtattagg tacttttgca  2040
cttgtatcat atattgcgaa taaggttcta accgttcaaa caatagataa tgctttaagt  2100
aaaagaaatg aaaaatggga tgaggtctat aaatatatag taacaaattg gttagcaaag  2160
gttaatacac agattgatct aataagaaaa aaatgaaag aagctttaga aaatcaagca  2220
gaagcaacaa aggctataat aaactatcag tataatcaat atactgagga agagaaaaat  2280
aatattaatt ttaatattga tgatttaagt tcgaaactta atgagtctat aaataaagct  2340
atgattaata taaatatt tttgaatcaa tgctctgttt catatttaat gaattctatg  2400
atcccttatg gtgttaaacg gttagaagat tttgatgcta gtcttaaaga tgcattatta  2460
aagtatatat atgataatag aggaacttta attggtcaag tagatagatt aaaagataaa  2520
gttaataata cacttagtac agatatacct tttcagcttt ccaaatacgt agataatcaa  2580
agattattat ctacatttac tgaatatatt aagaatatta ttaatacttc tatattgaat  2640
ttaagatatg aaagtaatca tttaatagac ttatctaggt atgcatcaaa aataaaattt  2700
ggtagtaaag taaattttga tccaatagat aaaaatcaaa ttcaattatt taatttagaa  2760
agtagtaaaa ttgaggtaat tttaaaaaat gctattgtat ataatagtat gtatgaaaat  2820
tttagtacta gcttttggat aagaattcct aagtatttta acagtataag tctaaataat  2880
gaatatacaa taataaattg tatggaaaat aattcaggat ggaaagtatc acttaattat  2940
ggtgaaataa tctggacttt acaggatact caggaaataa aacaaagagt agtttttaaa  3000
tacagtcaaa tgattaatat atcagattat ataaacagat ggattttttgt aactatcact  3060
aataatagat aaataactc taaaatttat ataaatggaa gattaataga tcaaaaaccga  3120
atttcaaatt taggtaatat tcatgctagt aataataata tgtttaaatt agtggttgt   3180
agagatacac atagatatat ttggataaaa tattttaata ttttgataaa ggaattaaat  3240
gaaaaagaaa tcaaagattt atatgataat caatcaaatt caggtatttt aaaagacttt  3300
tggggtgatt atttacaata tgataaacca tactatatgt taaatttata tgatccaaat  3360
aaatatgtcg atgtaaataa tgtaggtatt agaggttata tgtatcttaa agggcctaga  3420
ggtagcgtaa tgactacaaa catttatta aattcaagtt tgtataggga gacaaaattt  3480
attataaaaa aatatgcttc tggaaataaa gataatattg ttagaaataa tgatcgtgta  3540
tatattaatg tagtagttaa aaataaagaa taggttag ctactaatgc atcaacggca  3600
ggcgtagaaa aaatactaag tgcattagaa atacctgatg taggaaatct aagtcaagta  3660
gtagtaatga agtcaaaaaa tgatcaagga ataacaaata atgcaaaat gaatttacaa  3720
gataataatg ggaatgatat aggcttata ggatttcatc agtttaataa tagctaaa    3780
ctagtagcaa gtaattggta ataagacaa atagaaagat ctagtaggac tttgggttgc  3840
tcatgggaat ttattcctgt agatgatgga tggggagaaa ggccactgta a           3891

SEQ ID NO: 2              moltype = AA   length = 1296
FEATURE                   Location/Qualifiers
source                    1..1296
                          mol_type = protein
                          organism = Clostridium botulinum
```

```
SEQUENCE: 2
MPFVNKQFNY KDPVNGVDIA YIKIPNAGQM QPVKAFKIHN KIWVIPERDT FTNPEEGDLN    60
PPPEAKQVPV SYYDSTYLST DNEKDNYLKG VTKLFERIYS TDLGRMLLTS IVRGIPFWGG   120
STIDTELKVI DTNCINVIQP DGSYRSEELN LVIIGPSADI IQFECKSFGH EVLNLTRNGY   180
GSTQYIRFSP DFTFGFEESL EVDTNPLLGA GKFATDPAVT LAHELIHAGH RLYGIAINPN   240
RVFKVNTNAY YEMSGLEVSF EELRTFGGHD AKFIDSLQEN EFRLYYYNKF KDIASTLNKA   300
KSIVGTTASL QYMKNVFKEK YLLSEDTSGK FSVDKLKFDK LYKMLTEIYT EDNFVKFFKV   360
LNRKTYLNFD KAVFKINIVP KVNYTIYDGF NLRNTNLAAN FNGQNTEINN MNFTKLKNFT   420
GLFEFYKLLC VRGIITSKTK SLDKGYNKAL NDLCIKVNNW DLFFSPSEDN FTNDLNKGEE   480
ITSDTNIEAA EENISLDLIQ QYYLTFNFDN EPENISIENL SSDIIGQLEL MPNIERFPNG   540
KKYELDKYTM FHYLRAQEFE HGKSRIALTN SVNEALLNPS RVYTFFSSDY VKKVNKATEA   600
AMFLGWVEQL VYDFTDETSE VSTTDKIADI TIIIPYIGPA LNIGNMLYKD DFVGALIFSG   660
AVILLEFIPE IAIPVLGTFA LVSYIANKVL TVQTIDNALS KRNEKWDEVY KYIVTNWLAK   720
VNTQIDLIRK KMKEALENQA EATKAIINYQ YNQYTEEEKN NINFNIDDLS SKLNESINKA   780
MININKFLNQ CSVSYLMNSM IPYGVKRLED FDASLKDALL KYIYDNRGTL IGQVDRLKDK   840
VNNTLSTDIP FQLSKYVDNQ RLLSTFTEYI KNIINTSILN LRYESNHLID LSRYASKINI   900
GSKVNFDPID KNQIQLFNLE SSKIEVILKN AIVYNSMYEN FSTSFWIRIP KYFNSISLNN   960
EYTIINCMEN NSGWKVSLNY GEIIWTLQDT QEIKQRVVFK YSQMINISDY INRWIFVTIT  1020
NNRLNNSKIY INGRLIDQKP ISNLGNIHAS NNIMFKLDGC RDTHRYIWIK YFNLFDKELN  1080
EKEIKDLYDN QSNSGILKDF WGDYLQYDKP YYMLNLYDPN KYVDVNNVGI RGYMYLKGPR  1140
GSVMTTNIYL NSSLYRGTKF IIKKYASGNK DNIVRNNDRV YINVVVKNKE YRLATNASQA  1200
GVEKILSALE IPDVGNLSQV VVMKSKNDQG ITNKCKMNLQ DNNGNDIGFI GFHQFNNIAK  1260
LVASNWYNRQ IERSSRTLGC SWEFIPVDDG WGERPL                           1296

SEQ ID NO: 3          moltype = DNA   length = 3876
FEATURE               Location/Qualifiers
source                1..3876
                      mol_type = other DNA
                      organism = Clostridium botulinum
SEQUENCE: 3
atgccagtta caataaataa ttttaattat aatgatccta ttgataataa taatattat     60
atgatggagc tcccatttgc gagaggtacg gggagatatt ataaagcttt taaaatcaca   120
gatcgtattt ggataatacc ggaaagatat acttttggat ataaacctga ggattttaat   180
aaaagttccg gtattttttaa tagaagtgtt tgtgaatatt atgtccaga ttacttaaat    240
actaatgata aaaagaatat attttttacaa acaatgatca agttatttaa tagaatcaaa   300
tcaaaaccat tgggtgaaaa gttattagag atgattataa atggtatacc ttatcttgga   360
gatagacgtg ttccactcga agagtttaac acaaacattg ctagtgtaac tgttaataaa   420
ttaatcagta atccaggaga agtggagcga aaaaaaggta ttttcgcaaa ttttaataa    480
tttggacctg ggccagtttt aaatgaaaat gagactatag atataggtat acaaaatcat   540
tttgcatcaa gggaaggctt cggggggtata atgcaaatga agttttgccc agaatatgta   600
agcgtattta ataatgttca agaaaacaaa ggcgcaagta tatttaatag acgtggatat   660
ttttcagatc cagccttgat attaatgcat gaacttatac atgttttaca tggattatat   720
ggcattaaag tagatgattt aaccaattgt acaaatgaaa aaaaattttt tatgcaatct   780
acagatgcta tacaggcaga agaactatat acatttggag acaagatcc agcatcata    840
actccttcta cggataaaag tatctatgat aaagttttgc aaaattttag agggatagtt   900
gatagactta acaaggtttt agtttgcata tcagatccta acattaatat taatatatat   960
aaaaataaat ttaaagataa atataaattc gttgaagatt ctgagggaaa atatagtata  1020
gatgtagaaa gtttttgataa attatataaa agcttaatgt ttggttttac agaaactaat  1080
atagcagaaa attataaaat aaaaactaga gcttcctatt ttagtgattc cttaccacca  1140
gtaaaaataa aaaaatttatt agataatgaa atctatacta gaggaaagg gtttaatata  1200
tctgataaag atatggaaaa gaaatataga ggtcagaata agctataaa taaacaagct  1260
tatgaagaaa ttagcaagga gcatttggct gtatataaga tacaaatgtg taaaagtgtt  1320
aaagctccag gaatatgtat tgatgttgat aatgaagatt tgttcttat agctgataaa  1380
aatagttttt cagatgattt atctaaaaac gaaagaatag aatataatac acagagtaat  1440
tatatagaaa atgacttccc tataaatgaa ttaattttga atactgattt aataagtaaa  1500
atagaattac aagtgaaaaa tacagaatca cttactgatt taatgtaga tgttccagta   1560
tatgaaaaac aacccgctat aaaaaaaatt tttacagatg aaaataccat ctttcaatat  1620
ttatactctc agacatttcc tctagatata agagatataa gttaacatc tttcatttgat  1680
gatgcattat tattttctaa caaagtttat tcattttttt ctatggatta tattaaaact  1740
gctaataaag tggtagaagc aggattattt gcaggttggg tgaaacagat agtaaatgat  1800
tttgtaatcg aagctaataa aagcaatact atggataaaa ttgcagatat atctctaatt  1860
gttccttata taggattagc tttaaatgta ggaaatgaaa cagctaaagg aaattttgaa  1920
aatgcttttg agattgcagg agccagtatt ctactagaat ttataccaga acttttaata  1980
cctgtagttg gagcctttt attagaatca tatattgaca ataaaaataa aattattaaa   2040
acaatagata atgctttaac taaagaaaat gaaaatgga gtgatatgta cggattaata  2100
gtagcgcaat ggctctcaac agttaatact caattttata caataaaga gggaatgtat  2160
aaggctttaa attatcaagc acaagcattg gaagaaataa taaaatacag atataatata  2220
tattctgaaa aagaaaagtc aaatattaac atcgattta atgatataaa ttctaaactt  2280
aatgagggta ttaaccaagc tatagataat ataaataatt ttataaatgg atgttctgta  2340
tcatattaa tgaaaaaat gattccatta gctgtagaaa aattactaga cttttgataat  2400
actctcaaaa aaaatttgtt aaattatata gatgaaaata attatatttt gattggaagt  2460
gcagaatatg aaaaatcaaa agtaaataaa tacttgaaaa ccattatgcc gtttgatctt  2520
tcaatatata ccaatgatac aatactaata gaaatgttta taaatataa agcgaaatt  2580
ttaataatct ttatcttaaa tttaagatat aaggataata tttaatgaa aaataattcg  2640
tatgggcaa aggtagaggt atatgatgga gtcgagctta atgataaaaa tcaatttaaa  2700
ttaactagtt cagcaaatag taagattaga gtgactcaaa atcagaatat catatttaat  2760
agtgtgttcc ttgattttag cgttagcttt tggataagaa tacctaaata taagaatgat  2820
ggtatacaaa attatattca taatgaatat acaataatta attgtatgaa aaataattcg  2880
ggctggaaaa tatctattag gggtaatagg ataatatgga ctttaattga tataaatgga  2940
```

```
aaaaccaaat  cggtattttt  tgaatataac  ataagagaag  atatatcaga  gtatataaat   3000
agatggtttt  ttgtaactat  tactaataat  ttgaataacg  ctaaaattta  tattaatggt   3060
aagctagaat  caaatacaga  tattaaagat  ataagagaag  ttattgctaa  tggtgaaata   3120
atatttaaat  tagatggtga  tatagataga  acacaattta  tttggatgaa  atatttcagt   3180
attttaata   cggaattaag  tcaatcaaat  attgaagaaa  gatataaaat  tcaatcatat   3240
agcgaatatt  taaaagattt  tgggggaaat  cctttaatgt  acaataaaga  atattatatg   3300
tttaatgcgg  ggaataaaaa  ttcatatatt  aaactaaaga  aagattcacc  tgtaggtgaa   3360
attttaacac  gtagcaaata  taatcaaaat  tctaaatata  taaattatag  agatttatat   3420
attggagaaa  aatttattat  aagaagaaag  tcaaattctc  aatctataaa  tgatgatata   3480
gttagaaaag  aagattatat  atatctagat  ttttttaatt  taaatcaaga  gtggagagta   3540
tatacctata  aatattttaa  gaaagaggaa  gaaaaattgt  ttttagctcc  tataagtgat   3600
tctgatgagt  tttacaatac  tatacaaata  aaagaatatg  atgaacagcc  aacatatagt   3660
tgtcagttgc  tttttaaaaa  agatgaagaa  agtactgatg  agataggatt  gattggtatt   3720
catcgtttct  acgaatctgg  aattgtattt  gaagagtaaa  agattattt   ttgtataagt   3780
aaatggtact  taaaagaggt  aaaaaggaaa  ccatataatt  taaaattggg  atgtaattgg   3840
cagtttattc  ctaaagatga  agggtggact  gaataaa                              3876

SEQ ID NO: 4          moltype = AA   length = 1291
FEATURE               Location/Qualifiers
source                1..1291
                      mol_type = protein
                      organism = Clostridium botulinum
SEQUENCE: 4
MPVTINNFNY  NDPIDNNNII  MMEPPFARGT  GRYYKAFKIT  DRIWIIPERY  TFGYKPEDFN    60
KSSGIFNRDV  CEYYDPDYLN  TNDKKNIFLQ  TMIKLFNRIK  SKPLGEKLLE  MIINGIPYLG   120
DRRVPLEEFN  TNIASVTVNK  LISNPGEVER  KKGIFANLII  FGPGPVLNEN  ETIDIGIQNH   180
FASREGFGGI  MQMKFCPEYV  SVFNNVQENK  GASIFNRRGY  FSDPALILMH  ELIHVLHGLY   240
GIKVDDLPIV  PNEKKFFMQS  TDAIQAEELY  TFGGQDPSII  TPSTDKSIYD  KVLQNFRGIV   300
DRLNKVLVCI  SDPNININIY  KNKFKDKYKF  VEDSEGKYSI  DVESFDKLYK  SLMFGFTETN   360
IAENYKIKTR  ASYFSDSLPP  VKIKNLLDNE  IYTIEEGFNI  SDKDMEKEYR  GQNKAINKQA   420
YEEEISKEHLA VYKIQMCKSV  KAPGICIDVD  NEDLFFIADK  NSFSDDLSKN  ERIEYNTQSN   480
YIENDPFPINE LILDTDLISK  IELPSENTES  LTDFNVDVPV  YEKQPAIKKI  FTDENTIFQY   540
LYSQTFPLDI  RDISLTSSFD  DALLFSNKVY  SFFSMDYIKT  ANKVVEAGLF  AGWVKQIVND   600
FVIEANKSNT  MDKIADISLI  VPYIGLALNV  GNETAKGNFE  NAFEIAGASI  LLEFIPELLI   660
PVVGAFLLES  YIDNKNKIIK  TIDNALTKRN  EKWSDMYGLI  VAQWLSTVNT  QFYTIKEGMY   720
KALNYQAQAL  EEIIKYRYNI  YSEKEKSNIN  IDFNDINSKL  NEGINQAIDN  INNFINGCSV   780
SYLMKKMIPL  AVEKLLDFDN  TLKKNLLNYI  DENKLYLIGS  AEYEKSKVNK  YLKTIMPFDL   840
SIYTNDTILI  EMFNKYNSEI  LNNIILNLRY  KDNNLIDLSG  YGAKVEVYDG  VELNDKNQFK   900
LTSSANSKIR  VTQNQNIIFN  SVFLDFSVSF  WIRIPKYKND  GIQNYIHNEY  TIINCMKNNS   960
GWKISIRGNR  IIWTLIDING  KTKSVFFEYN  IREDISEYIN  RWFFVTITNN  LNNAKIYING  1020
KLESNTDIKD  IREVIANGEI  IFKLDGDIDR  TQFIWMKYFS  IFNTELSQSN  IEERYKIQSY  1080
SEYLKDFWGN  PLMYNKEYYM  FNAGNKNSYI  KLKKDSPVGE  ILTRSKYNQN  SKYINYRDLY  1140
IGEKFIIRRK  SNSQSINDDI  VRKEDYIYLD  FFNLNQEWRV  YTYKYFKKEE  EKLFLAPISD  1200
SDEFYNTIQI  KEYDEQPTYS  CQLLFKKDEE  STDEIGLIGI  HRFYESGIVF  EEYKDYFCIS  1260
KWYLKEVKRK  PYNLKLGCNW  QFIPKDEGWT  E                                   1291

SEQ ID NO: 5          moltype = DNA   length = 3843
FEATURE               Location/Qualifiers
source                1..3843
                      mol_type = other DNA
                      organism = Clostridium botulinum
SEQUENCE: 5
atgccaataa  caattaacaa  ctttaattat  tcagatcctg  ttgataataa  aaatatttta    60
tatttagata  ctcatttaaa  tacattagct  aatgagcctg  aaaaagcctt  tcgcattata   120
gggaatatat  gggtaatacc  cgatagattt  tcaagagctt  ctaatccaaa  tttaaataaa   180
cctcctcgag  ttacaagccc  taaaagtggt  tattatgatc  ctaattattt  gagtactgat   240
tctgaaaaag  atacatattt  aaaagaaatt  ataaagttat  ttaaaagaat  taactctaga   300
gaaatagagg  aagaattaat  atatagactt  gcaacagaca  tacccttttc  tgggaataac   360
aatactccaa  ttaatacttt  tgattttgat  gtagattttaa acagtgttga  tgttaaaact   420
agacaaggta  acaactgggt  taaaactggt  agtataaatc  ctagtgttat  aataactgga   480
cctagagaaa  acattataga  cccagaaact  tctacgttta  aattaactaa  caatactttt   540
gcggcacaag  aaggatttgg  tgctttatca  ataaatttca  atatcacctag atttatgcta   600
acatatagta  atgcaactaa  taatgtagga  gagggtagat  tttctaagtc  tgaattttgc   660
atggatccaa  tactaatttt  aatgcatgaa  cttatcgtta  caatgcataa  tttataatgga  720
atagctatac  caaatgatca  aagaaatttca tctgtaacta  gtaatatttt  ttattctcaa   780
tataaggtga  aattagagta  tgcagaaata  tatgcatttg  gaggtccaac  tatagacctt   840
attcctaaaa  gtgcaaggaa  atattttgag  gaaaaggcat  ggattatta   tagatccata   900
gctaaaagac  ttaatagtat  aactactgca  aatccttcaa  gctttaataa  atatataggt   960
gaatataaac  aagaaactat  tagaaagtat  agattcgtag  tagaatcttc  aggtgaagtt  1020
gcagtagatc  gtaataagtt  tgctgagtta  tataaagaac  ttacacaaat  atttacagaa  1080
tttaactacg  ctaaaatata  taatgtacaa  aataggaaaa  tatatctttc  aaatgtatat  1140
actccggtta  cggcaaatat  attagacgat  aatgtttatg  atatacaaaa  tggatttaac  1200
atacctaaaa  gtaatttaaa  tgtactattt  atgggtcaaa  atttatctcg  aaatccagca  1260
ttaagaaaca  tcaatcctga  aaattatctt  tatttattta  caaaatttg   ccataaagca  1320
atagatggta  gatcattata  taataaaaca  ttagatttta  gagagctttt  agttaaaaat  1380
actgacttac  cctttatagg  tgatattagt  gatatcaaaa  ctgatatatt  tttaagcaaa  1440
gatattaatg  aagaaactga  agttatagac  tatccggaca  tgtttcagt   ggatcaagtt  1500
attctcagta  agaatacctc  agaacatgga  caactagatt  tattataccc  tattattgaa  1560
ggtgagagtc  aagtattacc  gggagagaat  caagtctttt  atgataatag  aactcaaaat  1620
```

-continued

```
gttgattatt tgaattctta ttattaccta gaatctcaaa aactaagtga taatgttgaa   1680
gatttactt ttacgacatc aattgaggaa gctttggata atagtggaaa agtatatact   1740
tactttccta aactagctga taaagtaaat acgggtgttc aaggtggttt atttttaatg   1800
tgggcaaatg atgtagttga agatttact acaaatattc taagaaaaga tacattagat   1860
aaaatatcag atgtatcagc tattattccc tatatagcac ctgcattaaa tataagtaat   1920
tctgtaagaa ggggaaattt tactgaagca tttgcagtta ccggtgtaac tatttattta   1980
gaagcgtttc aagaattac aatacctgca cttggtgcat ttgtgattta tagtaaggtt   2040
caagaaagaa acgagattat taaaactata gataattgtt tagaacaaag gattaaaaga   2100
tggaaagatt catatgaatg gatgatagga acgtggttat ccaggattac tactcaatt    2160
aataatatat gttatcaaat gtatgattct ttaaattatc aggcagatgc aatcaaagat   2220
aaatagatt agaatataa aaaatactca ggaagtgata agaaaatat aaaagtcaa     2280
gttgaaaatt taaaaatag tttagatata aaatctcgg aagcaatgaa taatatataaa   2340
aaatttatac gagaatgttc tgtaacatac ttatttaaaa atatgctccc taaagtatat   2400
gatgaattaa ataagtttga ttaaaaact aaaacagaat taattaatct tatagatagt   2460
cataatatta ttctagttgg tgaagtagat agattaaaag caaaagtaaa tgagagtttt   2520
gaaaatacaa taccctttaa tattttttca tatactaata attctttatt aaaagatata   2580
attaatgaat attcaatag tattaatgat tcaaaattt tgagcttaca aaacaaaaaa     2640
aatgctttag tggatacatc aggatataat gcagaagtga ggctagaagg tgatgttcaa   2700
gttaatacga tatatacaaa tgattttaaa ttaagtagtg caggagataa aattatagta   2760
aatttaaata ataatattt atatagcgct atttatgaga actctagtgt tagttttgg     2820
attaagatat ctaaagattt aactaattct cataatgaat atacaataat taatagtata   2880
aaacaaaatt ctgggtggaa atagtgtatt aggaatggca atatagaatg gattttacaa   2940
gatattaata gaaagtataa aagtttaatt tttgattata gtgaatcatt aagtcataca   3000
ggatatacaa ataaatggtt ttttgttact ataactaata atataatggg gtatatgaaa   3060
ctttatataa atggagaatt aaagcagagt gaaagaattg aagatttaaa tgaggttaag   3120
ttagataaaa ccatagtatt tggaatagat gagaatatag atgcttggat tgaatcaatc   3180
attagagatt taatatttt ttctaaagaa ttaagcaatg aagatattaa tattgtatat   3240
gagggacaaa tattaagaa tgttattaaa gattattggg gaaatccttt gaagtttgat   3300
acagaatatt atattattaa tgataattat atagataggt atatagcacc taaaagtaat   3360
atacttgtac ttgttcagta tccagataga tctaaattat atactggaaa tcctattact   3420
attaaatcag tatctgataa gaatccttat agtagaattt taatggaga taataatg     3480
tttcatatgt tatataatag tgggaaatat atgataataa agatactga tacaatatat   3540
gcaatagaag gaagagagtg ttcaaaaaat tgtgtatatg cattaaaatt acagagtaat   3600
ttaggtaatt atggtatagg tatatttagt ataaaaaata ttgtatctca aataaatat    3660
tgtagtcaaa ttttctctag ttttatgaaa aatacaatgc ttctagcaga tatatataaa   3720
ccttggagat ttctctttga aaatgcatac acgccagttg cagtaactaa ttatgagaca   3780
aaactattat caacttcatc tttttggaaa tttatttcta gggatccagg atgggtagag   3840
taa                                                                3843
```

SEQ ID NO: 6        moltype = AA  length = 1280
FEATURE              Location/Qualifiers
source               1..1280
                        mol_type = protein
                        organism = Clostridium botulinum
SEQUENCE: 6

```
MPITINNFNY SDPVDKNIL YLDTHLNTLA NEPEKAFRII GNIWVIPDRF SRDSNPNLNK   60
PPRVTSPKSG YYDPNYLSTD SEKDTFLKEI IKLFKRINSR EIGEELIYRL ATDIPFPGNN  120
NTPINTFDFD VDFNSVDVKT RQGNNWVKTG SINPSVIITG PRENIIDPET STFKLTNNTF  180
AAQEGFGALS IISISPRFML TYSNATNNVG EGRFSKSEFC MDPILILMHE LNHAMHNLYG  240
IAIPNDQRIS SVTSNIFYSQ YKVKLEYAEI YAFGGPTIDL IPKSARKYFE EKALDYYRSI  300
AKRLNSITTA NPSSFNKYIG EYKQKLIRKY RFVVESSGEV AVDRNKFAEL YKELTQIFTE  360
FNYAKIYNVQ NRKIYLSNVY TPVTANILDD NVYDIQNGFN IPKSNLVLF MGQNLSRNPA   420
LRKVNPENML YLFTKFCHKA IDGRSLYNKT LDCRELLVKN TDLPFIGDIS DIKTDIFLSK  480
DINEETEVID YPDNVSVDQV ILSKNTSEHG QLDLLYPIIE GESQVLPGEN QVFYDNRTQN  540
VDYLNSYYYL ESQKLSDNVE DFTFTTSIEE ALDNSGKVYT YFPKLADKVN TGVQGGLFLM  600
WANDVVEDFT TNILRKDTLD KISDVSAIIP YIGPALNISN SVRRGNFTEA FAVTGVTILL  660
EAFQEFTIPA LGAFVIYSKV QERNEIIKTI DNCLEQRIKR WKDSYEWMIG TWLSRITTQF  720
NNISYQMYDS LNYQADAIKD KIDLEYKKYS GSDKENIKSQ VENLKNSLDI KISEAMNNIN  780
KFIRECSVTY LFKNMLPKVI DELNKFDLKT KTELINLIDS HNIILVGEVD RLKAKVNESF  840
ENTIPFNIFS YTNNSLLKDI INEYFNSIND SKILSLQNKK NALVDTSGYN AEVRLEGDVQ  900
VNTIYTNDFK LSSSGDKIIV NLNNNILYSA IYENSSVSFW IKISKDLTNS HNEYTIINSI  960
KQNSGWKLCI RNGNIEWILQ DINRKYKSLI FDYSESLSHT GYTNKWFFVT ITNNIMGYMK 1020
LYINGELKQS ERIEDLNEVK LDKTIVFGID ENIDENQMLW IRDFNIFSKE LSNEDINIVY 1080
EGQILRNVIK DYWGNPLKFD TEYYIINDNY IDRYIAPKSN ILVLVQYPDR SKLYTGNPIT 1140
IKSVSDKNPY SRILNGDNIM FHMLYNSGKY MIIRDTDTIY AIEGRECSKN CVYALKLQSN 1200
LGNYIGIFS IKNIVSQNKY CSQIFSSFMK NTMLLADIYK PWRFSFENAY TPVAVTNYET 1260
KLLSTSSFWK FISRDPGWVE                                            1280
```

SEQ ID NO: 7        moltype = DNA  length = 3858
FEATURE              Location/Qualifiers
source               1..3858
                        mol_type = other DNA
                        organism = Clostridium botulinum
SEQUENCE: 7

```
atgacatggc cagtaaaaga ttttaattat agtgatcctg ttaatgacaa tgatatatta    60
tatttaagaa taccacaaaa taagttaatt actacacctg taaagctttt tatgattact   120
caaaatattt gggtaatacc agaaagattt tcatcagata ctaatccaag tttaagtaaa   180
ccgcctagac tacttcaaa gtatcaaagt tattatgatc ctagttattt atctactgat   240
gagcaaaag tacatttt aaaggatt ataaaattat ttaaagaat taatgaaaga   300
```

```
gatataggaa aaaaattaat aaattattta gtagttggtt cacctttat gggagattca   360
agtacgcctg aagatacatt tgattttaca cgtcatacta ctaatattgc agttgaaaag   420
tttgaaaatg gtagttggaa agtaacaaat attataacac caagtgtatt gatatttgga   480
ccacttccta atatattaga ctatacagca tcccttacat tgcaaggaca caatcaaat    540
ccatcatttg aagggtttgg aacattatct atactaaaga tagcacctga attttttgtta  600
acatttagtg atgtaacatc taatcaaagt tcagctgtat taggcaaatc tatatttgt    660
atggatccag taatagcttt aatgcatgag ttaacacatt ctttgcatca attgtatgga   720
ataaatatac catctgataa aaggattcgt ccacaagtta gcgagggatt ttttctcaa    780
gatggaccca acgtacaatt tgaggaatta tacacatttg gaggatcaga tgttgaaata   840
ataccctcaa ttgaaagatt acaattaaga gaaaaagcat taggtcacta taaagatata   900
gcgaaaagac ttaataatat taataaaact attccttcta gttggagtag taatatagat   960
aaatatataaa aaatatttc tgaaaagtat aattttgata agataatac aggaaattt   1020
gttgtaaata ttgataaatt caatagctta tattcagact tgactaatgt tatgtcagaa  1080
gttgtttatt cttcgcaata taatgttaaa aacaggactc attattttc aaagcattat  1140
ctacctgtat ttgcaaatat attagatgat aatattata ctataataaa cggttttaat  1200
ttaacaacta aaggttttaa tatagaaaat tcgggtcaga atatagaaag gaatcctgca  1260
ctacaaaaac ttagttcaga aagtgtagta gatttgttta caaagtatg tttaagatta   1320
acaagaagta gtagagatga ttcaacatgt attcaagtta aaaataatac attaccttat   1380
gtagctgata agatagcat ttcacaagaa atatttgaaa gtcaaattat tacagatgag    1440
actaatgtag aaaattattc agataatttt tcattagatg aatctattt agatgcaaaa    1500
gtccctacta atcctgaagc agtagatcca ctgttaccca atgttaatat ggaacctta    1560
aatgttccag gtgaagaaga tgtattttat gatgatatta ctaaagatgt tgattattta   1620
aactcttatt attatttgga agcccaaaaa ttaagtaata atgttgaaaa tattactctt   1680
acaacttcag ttgaagaagc attaggttat agcaataaga tatacacatt tttacctagc   1740
ttagctgaaa aagtgaataa aggtgttcaa gcaggtttat tcttaaattg ggcgaatgaa   1800
gtagttgagg attttactac aaatattatg aaaaaagata cattggataa aatatcagat   1860
gtatcagcca taattccata tataggacct gccttaaata taggaaattc agcattaagg   1920
ggaaacttta agcaagcatt tgcaacagct ggtgtagctt ttttgttaga aggatttcca   1980
gagtttacaa tacctgcact cggtgtattt acctttata gttctattca agaaagagag   2040
aaaattatta aaactataga aaattgttta gaacaaagag ttaagagatg gaaagattca   2100
tatcaatgga tggtatcaaa ttggttgtca agaattacta ctcgatttaa tcatataagt   2160
tatcaaatgt atgattcttt gagttatcag gcagatgcaa tcaaagctaa aatagattta   2220
gaatataaaa aatactcagg aagtgataaa gaaaatataa aaagtcaagt tgaaaattta   2280
aaaaatagtt tagatgtaaa aatctcgaaa gcaatgaata atataaataa atttatacga   2340
gaatgttctg taacatactt attttaaaaat atgctcccta agtaattga tgaattaaat   2400
aagtttgatt taaaaactaa aacagaatta attaatctta tagatagtca taatattatt    2460
ctagttggtg aagtagatag attaaaagca aaagtaaatg agagtttga aaatacaata   2520
cccttttaata ttttttcata tactaataat tctttattaa aagatatgat taatgaatat  2580
ttcaatagta ttaatgattc aaaaattttg agcttacaaa ataaaaaaaa tacttttgatg  2640
gatacatcag gatataacgc agaagtgaga gtagaaggca atgttcagct taatccaata  2700
tttccatttg actttaaatt aggtagttca ggggatgata gaggtaaagt tatagtaacc  2760
cagaatgaaa atattgtata taatgctatg tatgaaagtt ttagtattag tttttggatt   2820
aggataaata aatgggtaag taatttaccct ggatatacta gaactaagat tgttaaaaat  2880
aactcaggtt ggagtatagg tattattagt aatttttag tgtttacttt aaaacaaaat   2940
gaaaatagtg aacaagatat aaactttagt tatgatatat caagaatgc tgcgggatat  3000
aataaatggt ttttgtaac tattactacc aatatgatgg gaaatgat gatttatata    3060
aatggaaaat taatagatac tataaaagtt aaagagttaa ctggaattaa ttttagcaaa  3120
actataacat ttcaaatgaa taaaattcca aatactggct taattacctc agattctgat  3180
aacatcaata tgtggataag ggatttttat atctttgcta aagaattaga tgataaagat  3240
attaatatat tatttaatag cttgcaatat actaatgttg taaaagatta ttggggaaat  3300
gatttaagat atgataaaga atattacatg attaacgtaa tttatatgaa tagatatatg  3360
tctaaaaaag gcaatggaat tgttttttaat acacgtaaaa ataataatga cttcaatgaa  3420
ggatataaaa ttataataaa aagaattaga ggaaatacaa atgatactag agtacgagga  3480
gaaaatgtat tatattttaa tactacaatt gataacaaac aatatagttt aggtatgtat  3540
aaaccttcta gaaatctagg gactgattta gttccactag gtcattgga tcaaccaatg  3600
gatgagatac gtaaatatgg ttcgttttata atacaaccat gcaatacttt tgattactat  3660
gcatcacaat tattttgtc aagtaatgca acaacaaata ggcttggaat actatcaatt   3720
ggtagttata gtttcaaact tggagatgac tattggttta atcacgaata tttaattcct   3780
gttataaaaa tagagcatta tgcttcatta ttagaatcaa catcaactca ttgggttttt   3840
gtacctgcaa gtgaataa                                                 3858

SEQ ID NO: 8         moltype = AA  length = 1285
FEATURE              Location/Qualifiers
source               1..1285
                     mol_type = protein
                     organism = Clostridium botulinum
SEQUENCE: 8
MTWPVKDFNY SDPVNDNDIL YLRIPQNKLI TTPVKAFMIT QNIWVIPERF SSDTNPSLSK    60
PPRPTSKYQS YYDPSYLSTD EQKDTFLKGI IKLFKRINER DIGKKLINYL VVGSPFMGDS   120
STPEDTFDFT RHTTNIAVEK FENGSWKVTN IITPSVLIFG PLPNILDYTA SLTLQGQQSN   180
PSFEGFGTLS ILKVAPEFLL TFSDVTSNQS SAVLGKSIFC MDPVIALMHE LTHSLHQLYG   240
INIPSDKRIR PQVSEGFFSQ DGPNVQFEEL YTFGGSDVEI IPQIERLQLR EKALGHYKDI   300
AKRLNNINKT IPSSWSSNID KYKKIFSEKY NFDKDNTGNF VVNIDKFNSL YSDLTNVMSE   360
VVYSSQYNVK NRTHYFSKHY LPVFANILDD NIYTIINGFN LTTKGFNIEN SGQNIERNPA   420
LQKLSSESVV DLFTKVCLRL TRNSRDDSTC IQVKNNTLPY VADKDSISQE IFESQIITDE   480
TNVENYSDNF SLDESILDAK VPTNPEAVDP LLPNVNMEPL NVPGEEEVFY DDITKDVDYL   540
NSYYYLEAQK LSNNVENITL TTSVEEALGY SNKIYTFLPS LAEKVNKGVQ AGLFLNWANE   600
VVEDFTTNIM KKDTLDKISD VSAIIPYIGP ALNIGNSALR GNFKQAFATA GVAFLLEGFP   660
EFTIPALGVF TFYSSIQERE KIIKTIENCL EQRVKRWKDS YQWMVSNWLS RITTRFNHIS   720
```

```
YQMYDSLSYQ ADAIKAKIDL EYKKYSGSDK ENIKSQVENL KNSLDVKISE AMNNINKFIR     780
ECSVTYLFKN MLPKVIDELN KFDLKTKTEL INLIDSHNII LVGEVDRLKA KVNESFENTI     840
PFNIFSYTNN SLLKDMINEY FNSINDSKIL SLQNKKNTLM DTSGYNAEVR VEGNVQLNPI     900
FPFDFKLGSS GDDRGKVIVT QNENIVYNAM YESFSISFWI RINKWVSNLP GYTIIDSVKN     960
NSGWSIGIIS NFLVFTLKQN ENSEQDINFS YDISKNAAGY NKWFFVTITT NMMGNMMIYI    1020
NGKLIDTIKV KELTGINFSK TITFQMNKIP NTGLITSDSD NINMWIRDFY IFAKELDDKD    1080
INILFNSLQY TNVVKDYWGN DLRYDKEYYM INVNYMNRYM SKKGNGIVFN TRKNNNDFNE    1140
GYKIIIKRIR GNTNDTRVRG ENVLYFNTTI DNKQYSLGMY KPSRNLGTDL VPLGALDQPM    1200
DEIRKYGSFI IQPCNTFDYY ASQLFLSSNA TTNRLGILSI GSYSFKLGDD YWFNHEYLIP    1260
VIKIEHYASL LESTSTHWVF VPASE                                         1285

SEQ ID NO: 9           moltype = DNA   length = 3756
FEATURE                Location/Qualifiers
source                 1..3756
                       mol_type = other DNA
                       organism = Clostridium botulinum
SEQUENCE: 9
atgccaaaaa ttaatagttt taattataat gatcctgtta atgatagaac aattttatat    60
attaaaccag gcggttgtca agaattttat aaatcattta atattatgaa aaatatttgg   120
ataattccag agagaaatgt aattggtaca accccccaag attttcatcc gcctacttca   180
ttaaaaaatg gagatagtag ttattatgac cctaattatt tacaaagtga tgaagaaaag   240
gatagatttt taaaaatagt cacaaaaata tttaataaat tctttcagga                300
gggattttat tagaagaact gtcaaaagct aatccatatt tagggaatga ataatactcca  360
gataatcaat tccatattgg tgatgcatca gcagttgaga ttaaattctc aaatggtagc   420
caagacatac tattacctaa tgttattata atgggagcag agcctgattt atttgaaact   480
aacagttcca atatttctct aagaaataat tatatgccaa tcaccg ttttggatca       540
atagctatag taacattctc acctgaatat tcttttagat taatgataaa ttgtatgaat   600
gaatttattc aagatcctgc tcttacatta atgcatgaat aatacattc attacatgga    660
ctatatgggg ctaaagggat tactacaaag tatactataa cacaaaaaca aaatccccta   720
ataacaaata taaggggtac aaatattgaa gaattcttaa cttttggaag tactgattta   780
aacattatta ctagtgctca gtccaatgat atctatacta atcttctagc tgattataaa   840
aaaatagcgt ctaaacttag caaagtacaa gtatctaatc cactacttaa tccttataaa   900
gatgttttt aagcaaagta tggattagat aaagatgcta gcggaattta ttcggtaaat    960
ataaacaaat ttaatgatat ttttaaaaaa ttatacagct ttacgaattt tgatttacga  1020
actaaatttc aagttaaatg taggcaaact tatattggac agtataaata cttcaaactt  1080
tcaaactgt taaatgattc tatttataat atatcagaag gctataatat aaataattta   1140
aaggtaaatt ttagaggaca gaatgcaaat ttaaatccta gaattattac accaattaca  1200
ggtagaggac tagtaaaaaa aatcattaga ttttgtaaaa atattgtttc tgtaaaaggc  1260
ataaggaaat caatatgtat cgaaataaat aatggtgagt tattttttgt ggcttccgag  1320
aatagttata atgatgataa tataaatact cctaaagaaa ttgacgatac agtaacttca  1380
aataataatt atgaaaatga tttagatcag gttattttaa attttaatag tgaatcagca  1440
cctggacttt cagatgaaaa attaaattta actatccaaa atgatgctta tacccaaaa   1500
tatgattcta atggaacaag tgatataaga caacatgatg ttaaagaact taatgtattt  1560
ttctatttag atgcacagaa agtgcccgaa ggtgaaaata atgtcaatct cacctcttca  1620
attgatacag cattattaga acaacctaaa atatatacat ttttttcatc agaatttatt  1680
aataatgtca ataaacctgt gcaagcagca ttatttgtaa gctggataca acaagtgtta  1740
gtagatttta ctactgaagc taaccaaaaa agtactgtta ataaaattgc agatatttct  1800
atagttgttc catatatagg tcttgcttta aatataggaa atgaagcaca aaaaggaaat  1860
tttaaagatg cacttgaatt attaggagca ggtattttat tagaatttga acccgagctt  1920
ttaattccta caatttgtagt attcacgata aaatcttttt taggttcatc tgataataaa  1980
aataaagtta tttaaagcaat aaataatgca ttgaaagaaa gaggtgaaaa atggaaagaa  2040
gtatatagtt ttataggtatc gaattggatg actaaaatta atacacaatt aataaaaga   2100
aaagaacaaa tgtatcaagc tttcaaaaat caagtaaaatg caattaaaac aataatagaa  2160
tctaagtata atagttatac tttagaggaa aaaaatgagc ttacaaataa atatgatatt  2220
aagcaaatag aaaatgaact taatcaaaag gtttctataa caattgataa atagacagg   2280
ttcttaactg aaagttctat atcctatttta atgaaaataa taatgaagt aaaaattaat  2340
aaattaagag aatatgatga aatgtcaaaa acgtatttat tgaattatat tatacaaacat  2400
ggatcaatct tgggagagag tcagcaagaa ctaaattcta tggtaactga taccctaaat  2460
aatagtattc cttttaagct ttcttcttat acagatgata aaattttaat ttcatatttt  2520
aataaattct ttaagagaat taaaagtagt tcagttttaa atatgagata taaaaatgat  2580
aaatacgtag atacttcagg atatgattca aatatataata ttaatggaga tgtatataaa  2640
tatccaacta taaaaatcta atttggaata tataatgata aacttagtga agttaatata  2700
tctcaaaatg attacattat atatgataat aaatataaaa attttagtat tagtttttgg  2760
gtaagaattc ctaactatga taataagata gtaaatgtta ataatgaaca cactataata  2820
aattgtatga gagataataa ttcaggatgg aaagtatctc ttaatcataa tgaaataatt  2880
tggacattcg aagataatcg aggaattaat caaaaattag catttaacta tggtaacgca  2940
aatggtattt ctgattatat aaataagtgg attttttgtaa ctataactaa tgatagatta  3000
ggagattcta aactttatat taatgaattt ataaaaaatat tttaaaattta           3060
gtaatattc atgttagtga caatatatta tttaaaatag ttaattgtag ttatacaaga   3120
tatattggta ttagatattt taatattttt gataaagaat tagatgaaac agaaattcaa  3180
acttatatata gcaatgaacc taatacaaat attttgaagg attttggggg aaattatttg  3240
ctttatgaca aagaatacta tttattaaat gtgttaaaac caaataactt tattgatagg  3300
agaaaagatt ctacttttaag cattaataat ataagaagca ctattctttt agctaataga  3360
ttatagtg gaataaaagt taaaatacaa agagtaata atagtagtaac taacgataat   3420
cttgttagaa agaatgatca ggtatatatt aattttgtag ccagcaaaac tcacttattt   3480
ccattatatg ctgatacagc taccacaaat aaagagaaaa caataaaaat atcatcatct  3540
ggcaatagat taatcaagt agtagttatg aattcagtag gaaattgtac aatgaatttt   3600
aaaaataata atggaaataa tattgggttg ttaggttcaa aggcagatac tgtcgttgct  3660
agtacttggt attatacaca tatgagagat catacaaaca gcaatggatg ttttttggaac 3720
```

```
tttatttctg aagaacatgg atggcaagaa aaataa                                3756
```

SEQ ID NO: 10          moltype = AA   length = 1251
FEATURE                Location/Qualifiers
source                 1..1251
                       mol_type = protein
                       organism = Clostridium botulinum
SEQUENCE: 10
```
MPKINSFNYN DPVNDRTILY IKPGGCQEFY KSFNIMKNIW IIPERNVIGT TPQDFHPPTS      60
LKNGDSSYYD PNYLQSDEEK DRFLKIVTKI FNRINNNLSG GILLEELSKA NPYLGNDNTP     120
DNQFHIGDAS AVEIKFSNGS QDILLPNVII MGAEPDLFET NSSNISLRNN YMPSNHRFGS     180
IAIVTFSPEY SFRFNDNCMN EFIQDPALTL MHELIHSLHG LYGAKGITTK YTITQKQNPL     240
ITNIRGTNIE EFLTFGGTDL NIITSAQSND IYTNLLADYK KIASKLSKVQ VSNPLLNPYK     300
DVFEAKYGLD KDASGIYSVN INKFNDIFKK LYSFTEFDLR TKFQVKCRQT YIGQYKYFKL     360
SNLLNDSIYN ISEGYNINNL KVNFRGQNAN LNPRIITPIT GRGLVKKIIR FCKNIVSVKG     420
IRKSICIEIN NGELFFVASE NSYNDDNINT PKEIDDTVTS NNNYENDLDQ VILNFNSESA     480
PGLSDEKLNL TIQNDAYIPK YDSNGTSDIE QHDVNELNVF FYLDAQKVPE GENNVNLTSS     540
IDTALLEQPK IYTFFSSEFI NNVNKPVQAA LFVSWIQQVL VDFTTEANQK STVDKIADIS     600
IVVPYIGLAL NIGNEAQKGN FKDALELLGA GILLEFEPEL LIPTILVFTI KSFLGSSDNK     660
NKVIKAINNA LKERDEKWKE VYSFIVSNWM TKINTQFNKR KEQMYQALQN QVNAIKTIIE     720
SKYNSYTLEE KNELTNKYDI KQIENELNQK VSIAMNNIDR FLTESSISYL MKIINEVKIN     780
KLREYDENVK TYLLNYIIQH GSILGESQQE LNSMVTDTLN NSIPFKLSSY TDDKILISYF     840
NKFFKRIKSS SVLNMRYKND KYVDTSGYDS NININGDVYK YPTNKNQFGI YNDKLSEVNI     900
SQNDYIIYDN KYKNFSISFW VRIPNYDNKI VNVNNEYTII NCMRDNNSGW KVSLNHNEII     960
WTFEDNRGIN QKLAFNYGNA NGISDYINKW IFVTITNDRL GDSKLYINGN LIDQKSILNL    1020
GNIHVSDNIL FKIVNCSYTR YIGIRYFNIF DKELDETEIQ TLYSNEPNTN ILKDFWGNYL    1080
LYDKEYYLLN VLKPNNFIDR RKDSTLSINN IRSTILLANR LYSGIKVKIQ RVNNSSTNDN    1140
LVRKNDQVYI NFVASKTHLF PLYADTATTN KEKTIKISSS GNRFNQVVVM NSVGNCTMNF    1200
KNNNGNNIGL LGFKADTVVA STWYYTHMRD HTNSNGCFWN FISEEHGWQE K             1251
```

SEQ ID NO: 11          moltype = DNA   length = 3843
FEATURE                Location/Qualifiers
source                 1..3843
                       mol_type = other DNA
                       organism = Clostridium botulinum
SEQUENCE: 11
```
atgccagttg taataaatag ttttaattat aatgaccctg ttaatgatga gacaatttta      60
tacatgcaga aaccatatga agaaagaagt agaaaatatt ataaagcttt tgagattatg     120
cctaatgttt ggataatgcc tgagagagat acaataggaa ctaagcctga tgagtttatg     180
gtgccggatt cattaaagaa cggaagtagt gcttattatg atcctaatta tttaaccact     240
gatgctgaaa aagatagata tttaaaaaca atgataaaat tatttaatag aattaatagt     300
aatcctacag ggaaagtttt gttagaagaa gtatcaaatg ctagaccata tttaggagat     360
gatgacacgc taattaatga attccttcca gttaatgtaa ctacaagtgt taatataaaa     420
ttttcaactg atgttgaaag ttcaataata tcgaatcttc ttgtattggg agcaggacct     480
gatatattta aagcttactg taccccccti gtaaggttta ataagtcaga taaattaatt     540
gaaccaagta atcatggttt tggatcaatt aatatcttga catttttcacc tgagtatgaa     600
catatttttta atgatattag tggagggaat cataatagta cagaatcatt tattgcagat     660
cctgcaattt cactagctca tgaattgata catgcactac atggattata cggggctaag     720
gcagttactc ataaagagtc tctagtagca gagcgaggac ctcttatgat agccgaaaag     780
cccataaggc tagaagaatt tttaactttt ggaggtgagg atttaaatat cattcctagt     840
gctatgaagg aaaaaatata taacgatctt ttagctaact gtaaaaaat agctactaga     900
cttagagaag ttaatacggc tcctcctgga tatgatatta tgaatataaa agattatttt     960
caatggaagt atggactaga tagaaatgca gatggaagtt atactgtgaa tagaaataaa    1020
tttaatgaaa tttataaaaa attatatagc tttacagaga ttgacttagc aaataaattt    1080
aaagtaaaat gtagaaatac ttattttatt aaatatgatt ttgtaaaagt tccaaatttg    1140
ttagatgatg atatttatac tgtatcagag gggtttaata taggtaattt agcagtaaac    1200
aatcgcggac aaaatataaa tttaaatcct aaaattattg attccattcc agataaaggt    1260
ttagtggaaa agattattaa attttgtaag agcattattc ctagaaaagg tacgaagcag    1320
tcaccgtcac tatgcattag agtaaataat agggagttat ttttgtgg ttcagaaagt      1380
agctataatg aaagtgatat taatacacct aaagaaattg acgatacaac aaatctaaat    1440
aataattata gaaataattt agatgaagtt attttagatt ataatagtga gacaatacct    1500
caaatatcaa atcgaacatt aaatacactt gtacaagaca atagttatgt gccaagatat    1560
gattctaatg aacaagtgaa atagaggaa tatgatgttg ttgactttaa tgtatttttc    1620
tatttacatg cacaaaaagt accagaaggt gaaccaatat taagtttaac ttcttcaatt    1680
gatacagcat tattgaaaga atccaaagta tatacatttt tttcttcaga gtttatcgat    1740
actatcaata aacctgtaaa tgcagcacta tttatagatt ggataagcaa agtaatgaaga    1800
gattttacca ctgaagctac acaaaaaagt actgttgata gattgcaga catatctta    1860
attgtaccct atgtaggtct tgctttgaat atagttattg aggcagaaaa aggaaattt    1920
gaggaggcat tgaattatt aggagcgggt attttgaat aattttgtgcc agagcttaca    1980
attcctgtaa ttttagtgtt tacgataaaa tcctatatag attcatatga gaataaaaat    2040
aaagcaatta aagcaataaa taattcatta atcgaaagag aagcaaagtg aaagaaata    2100
tatagttgga tagtatcaaa ttggcttact agaattaata cgcaatttaa taaagaaaa    2160
gagcaaaatg tcaggccttt acaaaatcaa gtagatgcaa taaaaacagc aataggaata    2220
aaatatata attatactc aatgagaaaa aaagtagata aatccaaaa taattcaat     2280
aatatagaag aagaattgaa taaaaaagtg tctttagcaa tgaaaatat agaaagattt    2340
atgcagaaaa gttctatatc ttatttaatg aaatttaataa atgaagccga agttggaaa    2400
ttaaaagaat atgatataaaca tgttaagagc gatttattag actatattct ctaccataaa    2460
tttaatccttg agagcagac aaaggaaatta attgatttgg tgactagtac tttgaatagt    2520
agtattccat ttgaacttt ttcatatact aatgataaaa ttcctaatat atattttaat    2580
```

```
agattatata aaaaaattaa agatagttct attttagata tgcgatatga aaataataaa   2640
tttatagata tctctggata tggttcaaat ataagcatta atggaaacgt atatatttat   2700
tcaacaaata gaaatcaatt tggaatatat agtggtaggc ttagtgaagt taatatagct   2760
caaaataatg atattatata caatagtaga tatcaaaatt ttagtattag tttctgggta   2820
accattccta aacactacag acctatgaat cgtaatcggg aatacactat aataaattgt   2880
atggggaata ataattcggg atggaaaata tcacttagaa ctattagaga ttgtgaaata   2940
atttggactt tacaagatac ttccggaaat aaggaaaaat taattttag gtatgaagaa    3000
cttgctagta tatctgatta tataaataaa tggattttg taactattac taataataga    3060
ttaggcaatt ctagaattta catcaatgga aatttaatag ttgaaaaatc aatttcgaat   3120
ttaggtgata ttcatgttag tgataatata ttatttaaaa ttgttggttg tgatgatgaa   3180
acgtatgttg gtataagata ttttaaagtt tttaatacgg aattagataa aacagaaatt   3240
gagactttat atagtaatga gccagatcca agtatcttaa aagactattg gggaaattat   3300
ttgctatata ataaaaaata ttattattc aatttactaa gaaaagataa gtatattact    3360
cggaattcag gcatttaaa tattaatcaa caaagaggtg ttactggagg catatctgtt    3420
tttttgaact ataaattata tgaaggagta gaagttatta taagaaaaaa tgctcctata   3480
gatatatcta atacagataa ttttgttaga aaaaacgatc tagcatacat taatgtagta   3540
gatcatggtg tagaatatcg gttatatgct gatatatca ttacaaaatc agagaaaata    3600
ataaaattaa taagaacatc taatccaaac gatgcttag gtcaaattat agttatgat     3660
tcaataggaa ataattgcac aatgaatttt caaaacaatg atgggagcaa tataggatta   3720
ctaggttttc attcagatga tttggttgct agtagttggt attataacca tatacgaaga   3780
aacactagca gtaatggatg cttttggagt tttattctta aagagcatgg ttggaaagaa   3840
taa                                                                 3843

SEQ ID NO: 12           moltype = AA  length = 1280
FEATURE                 Location/Qualifiers
source                  1..1280
                        mol_type = protein
                        organism = Clostridium botulinum
SEQUENCE: 12
MPVVINSFNY NDPVNDETIL YMQKPYEERS RKYYKAFEIM PNVWIMPERD TIGTKPDEFQ   60
VPDSLKNGSS AYYDPNYLTT DAEKDRYLKT MIKLFNRINS NPTGKVLLEE VSNARPYLGD  120
DDTLINEFLP VNVTTSVNIK FSTDVESSII SNLLVLGAGP DIFKAYCTPL VRFNKSDKLI  180
EPSNHGFGSI NILTFSPEYE HIFNDISGGN HNSTESFIAD PAISLAHELI HALHGLYGAK  240
AVTHKESLVA ERGPLMIAEK PIRLEEFLTF GGEDLNIIPS AMKEKIYNDL LANYEKIATR  300
LREVNTAPPG YDINEYKDYF QWKYGLDRNA DGSYTVNRNK FNEIYKKLYS FTEIDLANKF  360
KVKCRNTYFI KYGFVKVPNL LDDDIYTVSE GFNIGNLAVN NRGQNINLNP KIIDSIPDKG  420
LVEKIIKFCK SIIPRKGTKQ SPSLCIRVNN RELFFVASES SYNESDINTP KEIDDTTNLN  480
NNYRNNLDEV ILDYNSETIP QISNRTLNTL VQDNSYVPRY DSNGTSEIEE YDVVDFNVFF  540
YLHAQKVPEG ETNISLTSSI DTALLEESKV YTFFSSEFID TINKPVNAAL FIDWISKVIR  600
DFTTEATQKS TVDKIADISL IVPYVGLALN IVIEAEKGNF EEAFELLGAG ILLEFVPELT  660
IPVILVFTIK SYIDSYENKN KAIKAINNSL IEREAKWKEI YSWIVSNWLT RINTQFNKRK  720
EQMYQALQNQ VDAIKTAIEY KYNNYTSDEK NRLESKYNIN NIEEELNKKV SLAMKNIERF  780
MTESSISYLM KLINEAEVGK LKEYDKHVKS DLLDYILYHK LILGEQTKEL IDLVTSTLNS  840
SIPFELSSYT NDKILIIYFN RLYKKIKDSS ILDMRYENNK FIDISGYGSN ISINGNVYIY  900
STNRNQFGIY SGRLSEVNIA QNNDIIYNSR YQNFSISFWV TIPKHYRPMN RNREYTIINC  960
MGNNNSGWKI SLRTIRDCEI IWTLQDTSGN KEKLIFRYEE LASISDYINK WIFVTITNNR 1020
LGNSRIYING NLIVEKSISN LGDIHVSDNI LFKIVGCDDE TYVGIRYFKV FNTELDKTEI 1080
ETLYSNEPDP SILKDYWGNY LLYNKKYYLF NLLRKDKYIT RNSGILNINQ QRGVTGGISV 1140
FLNYKLYEGV EVIIRKNAPI DISNTDNFVR KNDLAYINVV DHGVEYRLYA DISITKSEKI 1200
IKLIRTSNPN DSLGQIIVMD SIGNNCTMNF QNNDGSNIGL LGFHSDDLVA SSWYYNHIRR 1260
NTSSNGCFWS FISKEHGWKE                                            1280

SEQ ID NO: 13           moltype = DNA  length = 3894
FEATURE                 Location/Qualifiers
misc_feature            20
                        note = n is a, c, g, or t
source                  1..3894
                        mol_type = other DNA
                        organism = Clostridium botulinum
SEQUENCE: 13
atgccagtta atataaaaan ctttaattat aatgacccta ttaataatga tgacattatt     60
atgatggaac cattcaatga cccagggcca ggaacatatt ataaagcttt taggattata   120
gatcgtattt ggatagtacc agaaaggttt acttatggat ttcaacctga ccaatttaat   180
gccagtacag gagtttttag taaagatgtc tacgatcaac acgatccaac ttatttaaaa   240
accgatgctg aaaagataa attttaaaa acaatgatta aatttattaa tagaattaat    300
tcaaaaccat caggacagag attactggat atgatagtag atgctatacc ttatcttgga   360
aatgcatcta caccgcccga caatttgca gcaaatgttg caaatgtatc tattaataaa    420
aaattatcc aacctggagc tgaagatcaa ataaaaggtt taatgacaaa tttaataata    480
tttggaccag gaccagttct aagtgataat tttactgata tatgattat gaatggccat    540
tccccaatat cagaaggatt tggtgcaaga atgatgataa gattttgtcc tagttgttta   600
aatgtattta ataatgttca ggaaaataaa gatcatccta tatttagtag acgcgcgtat   660
tttgcagatc cagctctaac gttaatgcat gaacttatac atgtgttaca tggattatat   720
ggaattaaga taagtaattt accaattact ccaaatacaa aagaattttt catgcaacat   780
agcagcctg tacaagcaga agaactatat acattcggaa ctagtgttta                840
agtccttcta cggatatgaa tatttataat aaagcgttac aaaatttca agatatagct    900
aataggctta atattgtttc aagtgcccaa gggagtggaa ttgatatttc cttatataaa   960
caaatatata aaaataaata tgattttgtt gaagatccta atggaaaata tagtgtagat  1020
aaggataagt ttgataaatt atataaggcc ttaatgtttg ctttactga aactaatcta   1080
gctggtgaat atgaataaaa aactaggtat tcttatttta gtgaatattt gccaccgata  1140
```

-continued

```
aaaactgaaa aattgttaga caatacaatt tatactcaaa atgaaggctt taacatagct  1200
agtaaaaatc tcaaaacgga atttaatggt cagaataagg cggtaaataa agaggcttat  1260
gaagaaatca gcctagaaca tctcgttata tatagaatag caatgtgcaa gcctgtaatg  1320
tacaaaaata ccggtaaatc tgaacagtgt attattgtta ataatgagga tttatttttc  1380
atagctaata aagatagttt ttcaaaagat ttagctaaga cagaaactat agcatataat  1440
acacaaaata atactataga aaataatttt tctatagatc agttgatttt agataatgat  1500
ttaagcagtg gcatagactt accaaatgaa aacacagaac catttacaaa ttttgacgac  1560
atagatatcc ctgtgtatat taaacaatct gctttaaaaa aattttttgt ggatggagat  1620
agcctttttg aatatttaca tgctcaaaca tttccttcta atatagaaaa tctacaacta  1680
acgaattcat taaatgatgc tttaagaaat aataataaag tctatacttt ttttctaca   1740
aaccttgttg aaaaagctaa tacagttgta ggtgcttcac ttttttgtaaa ctgggtaaaa  1800
ggagtaatag atgattttac atctgaatcc acacaaaaaa gtactataga taaagtttca  1860
gatgtatcca taattattcc ctatatagga cctgctttga atgtaggaaa tgaaacagct  1920
aaagaaaatt ttaaaaatgc tttttgaaata ggtgggagccg ctatcttaat ggagtttatt  1980
ccagaactta ttgtacctat agttggattt tttacattag aatcatatgt aggaaataaa  2040
gggcatatta ttatgacgat atccaatgct ttaaagaaaa gggatcaaaa atggacagat  2100
atgtatggtt tgatagtatc gcagtggctc tcaacggtta atactcaatt ttatacaata  2160
aaagaaagaa tgtacaatgc tttaaataat caatcacaag caatagaaaa aataatagaa  2220
gatcaatata atagatatag tgaagaagat aaaaatgaata ttaacattga ttttaatgat  2280
atagattta aacttaatca aagtataaat ttagcaataa acaatataga tgattttata  2340
aaccaatgtt ctatatcata tctaatgaat agaatgattc cattagctgt aaaaaagtta  2400
aaagacttttg atgataatct taagagagat ttattggaat atatagatac aaatgaacta  2460
tatttacttg atgaagtaaa tattctaaaa tcaaaagtaa atagacacct aaaagacagt  2520
ataccatttg atcttcact atataccaag gacacaattt taatacaagt ttttaataat  2580
tatattagta atattagtag taatgctatt ttaagtttaa gttatagagg tgggcgttta  2640
atagattcat ctggatatgg tgcaactatg aatgtaggtt cagatgttat ctttaatgat  2700
ataggaaatg gtcaatttaa attaaataat tctgaaaata gtaatattac ggcacatcaa  2760
agtaaattcg ttgtatatga tagtatgttt gataattta gcattaactt ttgggtaagg  2820
actcctaaat ataataataa tgatatacaa acttatcttc aaaatgagta tacaataatt  2880
agttgtataa aaaatgactc aggatggaaa gtatctatta agggaaatag aataatagga  2940
acattaatag atgttaatgc aaaatctaaa tcaatatttt tcgaatatag tataaaagat  3000
aatatatcag attatataaa taaatggttt ccataacta ttactaatga tagattaggt  3060
aacgcaaata tttatataaa tggaagtttg aaaaaaagtg aaaaaatttt aaacttagat  3120
agaattaatt ctagtaatga tatagacttc aaattaatta attgtacaga tactactaaa  3180
tttgtttgga ttaaggattt taatattttt ggtagagaat taaatgctac agaagtatct  3240
tcactatatt ggattcaatc atctacaaat acttttaaaag atttttgggg gaatccttta  3300
agatacgata cacaatacta tctgtttaat caaggtatgc aaaatatcta tataaagtat  3360
tttagtaaag cttctatggg ggaaactgca ccacgtacaa actttaataa tgcagcaata  3420
aattatcaaa atttatatct tggtttacga tttattataa aaaaagcatc aaattctcga  3480
aatataaata atgataatat agtcagagaa ggagattata tatatcttaa tattgataat  3540
atttctgatg aatcttacag agtatatgtt ttggtgaatt ctaaagaaat tcaaactcaa  3600
ttattttag cacccataaa tgatgatcct acgttctatg atgtactaca aataaaaaaa  3660
tattatgaaa aacaacata taattgtcag atactttgcg aaaaagatac taaaacttt   3720
gggctgtttg gaattggtaa atttgttaaa gattatggat atgtttggga tacctatgat  3780
aattattttt gcataagtca gtggtatctc agaagaaatat ctgaaaatat aaataaatta  3840
aggttgggat gtaattggca attcattccc gtggatgaag gatggacaga ataa        3894
```

SEQ ID NO: 14          moltype = AA    length = 1297
FEATURE                Location/Qualifiers
SITE                   7
                         note = MISC_FEATURE - Xaa can be any naturally occurring amino acid
source                 1..1297
                         mol_type = protein
                         organism = Clostridium botulinum
SEQUENCE: 14

```
MPVNIKXFNY NDPINNDDII MMEPFNDPGP GTYYKAFRII DRIWIVPERF TYGFQPDQFN   60
ASTGVFSKDV YEYYDPTYLK TDAEKDKFLK TMIKLFNRIN SKPSGQRLLD MIVDAIPYLG  120
NASTPPDKFA ANVANVSINK KIIQPGAEDQ IKGLMTNLII FGPGPVLSDN FTDSMIMNGH  180
SPISEGFGAR MMIRFCPSCL NVFNNVQENK DTSIFSRRAY FADPALTLMH ELIHVLHGLY  240
GIKISNLPIT PNTKEFFMQH SDPVQAEELY TFGGHDPSVI SPSTDMNIYN KALQNFQDIA  300
NRLNIVSSAQ GSGIDISLYK QIYKNKYDFV EDPNGKYSVD KDKFDKLYKA LMFGFTETNL  360
AGEYGIKTRY SYFSEYLPPI KTEKLLDNTI YTQNEGFNIG SKNLKTEFNG QNKAVNKEAY  420
EEISLEHLVI YRIAMCKPVM YKNTGKSEQC IIVNNEDLFF IANKDSFSKD LAKAETIAYN  480
TQNNTIENNF SIDQLILDND LSSGIDLPNE NTEPFTNFDD IDIPVYIKQS ALKKIFVDGD  540
SLFEYLHAQT FPSNIENLQL TNSLNDALRN NKVYTFFST NLVEKANTVV GASLFVNWVK  600
GVIDDFTSES TQKSTIDKVS DVSIIIPYIG PALNVGNETA KENFKNAFEI GGAAILMEFI  660
PELIVPIVGF FTLESYVGNK GHIIMTISNA LKKRDQKWTD MYGLIVSQWL STVNTQFYTI  720
KERMYNALNN QSQAIEKIIE DQYNRYSEED KMNINIDFND IDFKLNQSIN LAINNIDDFI  780
NQCSISYLMN RMIPLAVKKL KDFDDNLKRD LLEYIDTNEL YLLDEVNILK SKVNRHLKDS  840
IPFDLSLYTK DTILIQVFNN YISNISSNAI LSLSYRGGRL IDSSGYGATM NVGSDVIFND  900
IGNGQFKLNN SENSNITAHQ SKFVVYDSMF DNFSINFWVR TPKYNNNDIQ TYLQNEYTII  960
SCIKNDSGWK VSIKGNRIIW TLIDVNAKSK SIFFEYSIKD NISDYINKWF SITITNDRLG 1020
NANIYINGSL KKSEKILNLD RINSSNDIDF KLINCTDTTK FVWIKDFNIF GRELNATEVS 1080
SLYWIQSSTN TLKDFWGNPL RYDTQYYLFN QGMQNIYIKY FSKASMGETA PRTNFNNAAI 1140
NYQNLYGLR FIIKKASNSR NINNDNIVRE GDYIYLNIDN ISDESYRVYV LVNSKEIQTQ 1200
LFLAPINDDP TFYDVLQIKK YYEKTTYNCQ ILCEKDTKTF GLFGIGKFVK DYGYVWDTYD 1260
NYFCISQWYL RRISENINKL RLGCNWQFIP VDEGWTE                          1297
```

| SEQ ID NO: 15 | moltype = DNA length = 4400 |
|---|---|
| FEATURE | Location/Qualifiers |
| source | 1..4400 |
| | mol_type = other DNA |
| | organism = Clostridium tetani |

SEQUENCE: 15

```
tagcattaaa aaaattagaa cctatagtaa ataaattaat taatatatag ttttttataat   60
ttaattatga ataatattct taagataaaa agtaaatttt taaaaattta aattttcagt  120
ttacaaaaaa taacctgatt atgttatatg taattgtaaa aaacatataa aaaatcagaa  180
aaatttagga ggtatattat taatggatta aataataatt ttttaattta cttttgatta  240
ataaatatta aatgtttatt ttaattagga gatgatacgt atgccaataa ccataaataa  300
ttttagatat agtgatcctg ttaataatga tacaattatt atgatggagc caccatactg  360
taagggtcta gatatctatt ataaggcttt caaaataaca gatcgtattt ggatagtgcc  420
ggaaaggtat gaatttggga caaaacctga agattttaac ccaccatctt cattaataga  480
aggtgcatct gagtattacg atccaaatta tttaaggact gattctgata agatagatt  540
tttacaaacc atggtaaaac tgtttaacag aattaaaaac aatgtagcag gtgaagcctt  600
attagataag ataataaatg ccatacctta ccttggaaat tcatattcct tactagacaa  660
gtttgataca aactctaatt cagtatcttt taatttatta gaacaagacc ccagtggagc  720
aactacaaaa tcagcaatgc tgacaaattt aataatattt ggacctgggc ctgttttaaa  780
taaaaatgag gttagaggta ttgtattgag ggtagataat aaaaaattact tcccatgtag  840
agatggttttt ggctcaataa tgcaaatggc attttgccca gaatatgtac ctacctttga  900
taatgtaata gaaaatatta cgtcactcac tattggcaaa agcaaatatt ttcaagatcc  960
agcattacta ttaatgcacg aacttataca tgtactacat ggtttatacg gaatgcaggt 1020
atcaagccat gaaattattc catccaaaca agaaatttat atgcagcata catatccaat 1080
aagtgctgaa gaactattca cttttggcgg acaggatgct aatcttataa gtattgatat 1140
aaaaaacgat ttatatgaaa aaactttaaa tgattataaa gctatagcta acaaacttag 1200
tcaagtcact agctgcaatg atcccaacat tgatattgat agctacaaac aaatatatca 1260
acaaaaatat caattcgata agatagcaa tggacaatat attgtaaatg aggataaatt 1320
tcagatacta tataatagca taatgtatgg ttttacagag attgaattgg gaaaaaaatt 1380
taatataaaa actagacttt cttattttag tatgaatcat gaccctgtaa gaattccaaa 1440
tttattagat gatacaattt acaatgatac agaaggattt aatatagaaa gcaaagatct 1500
gaaatctgaa tataaaggac aaaaatgag ggtaaataca aatgcttta gaaatgttga 1560
tggatcaggc ctagtttcaa aacttattgg cttatgtaaa aaaattatac caccaacaaa 1620
tataagagaa aatttatata atagaactgc atcattaaca gatttaggag gagaattatg 1680
tataaaaatt aaaaatgaag atttaactttt tatagctgaa aaaaatagct tttcagaaga 1740
accatttcaa gatgaaatag ttagttataa tacaaaaaat aaaccattaa attttaatta 1800
ttcgctagat aaaattattg tagattataa tctacaaagt aaaattacat tacctaatga 1860
taggacaacc ccagttacaa aaggaattcc atatgctcca gaatataaaa gtaatgctgc 1920
aagtacaata gaaatacata atattgatga caatacaata tatcaatatt tgtatgctca 1980
aaaatctcct acaactctac aaagaataac tatgactaat tctgttgatg acgcattaat 2040
aaaattccacc aaaatatatt catattttcc atctgtaatc agtaaagtta accaaggtgc 2100
acaaggaatt ttattcttac agtgggtgag agatataatt gatgatttta ccaatgaatc 2160
ttcacaaaaa actactactcc ataaaatttc agatgtatcc actattgttc cttatatagg 2220
acccgcatta aacattgtaa aacaaggcta tgagggaaac tttataggcg ctttagaaac 2280
taccggagtg gtttttatta tagaatatat tccagaaatt acttaccag taattgcagc 2340
tttatctata gcagaaagta gcacacaaaa agaaagata taaaaacaa tagataactt 2400
tttagaaaaa agatatgaaa aatggattga agtatataaa ctagtaaaag caaaatggtt 2460
aggcacagtt aatacgcaat tccaaaaaag aagttatcaa atgtatagat ctttagaata 2520
tcaagtagat gcaataaaaa aaataataga ctatgaatat aaaatatatt caggacctga 2580
taaggaacaa attgccgacg aaattaataa tctgaaaaac aaacttgaag aaaaggctaa 2640
taaagcaatg ataaacataa atatatttat gagggaaagt tctagatcat ttttagttaa 2700
tcaaatgatt aacgaagcta aaagcagtt attagagttt gatactcaaa gcaaaaatat 2760
tttaatgcag tatataaag caaattctaa attttataggt ataactgaac taaaaaatt 2820
agaatcaaaa ataacaaag ttttttcaac accaattcca tttcttatt ctaaaaatct 2880
ggattgttgg gttgataatg aagaagatat agatgttata ttaaaaaaga gtacaatttt 2940
aaatttagat attaataatg atattatatc agatatatct gggttttaat catctgtaat 3000
aacatatcca gatgctcaat tggtgcccgg aataaatggc aaagcaatac atttagtaaa 3060
caatgaatct tctgaagtta tagtgcataa agctatggat attgaatata atgatatgtt 3120
taatttttt accgttagct tttggttgag ggttcctaaa gtatctgcta gtcatttaga 3180
acaaatatggc acaaatgagt attcaataat tagctctatg aaaaaacata gtctatcaat 3240
aggatctggt tggagtgtat cacttaaagg taataactta atatggactt taaaagattc 3300
cgcgggagaa gttagacaaa taacttttag ggatttaccct gataaattta atgcttattt 3360
agcaaataaa tgggttttta taactattac taatgataga ttatcttctg ctaatttgta 3420
tataaatgga gtacttatgg gaagtgcaga aattactggt taggagcta ttagagagga 3480
taataatata acattaaaac tagatagatg taataataat aatcaatacg tttctattga 3540
taaatttagg atattttgca aagcattaaa tccaaaagag attgaaaaat tatacacaag 3600
ttatttatct ataaccttttt taagagactt ctggggaaac cctttacgat atgatacaga 3660
atattattta ataccagtag cttctagttc taaagatgtt caattgaaaa ataacaga 3720
ttatatgtat ttgacaaatg cgccatcgta tactaacgga aaattgaata tatattag 3780
aaggttatat aatggactaa aatttattat aaaaagatat acacctaata tgaaataga 3840
ttcttttgtt aaatcaggtg attttattaa attatatgta tcatataaca ataatgagca 3900
cattgtaggt tatccgaaag atggaaatgc ctttaataat cttgatagaa ttctaagagt 3960
aggttataat gccccaggta tccctctttta taaaaaaatg gaagcagtaa aattgcgtga 4020
tttaaaaacc tattctgtac aacttaaatt atatgatgaa aagatgcat ctttaggact 4080
agtaggtacc cataatggtc aaataggcaa cgatccaaat agggatatat taattgcaag 4140
caactggtac tttaatcatt taaaagataa aattttagga tgtgattggt actttgtacc 4200
tacagatgaa ggatgggacaa atgattaaac agattgatat gttcatgatt actctatata 4260
aaaaattaaa taatataaca atctagctat attatttttg attattttct taatatatac 4320
taataaaaata atcaaaatag agcctatctt aaattactga agggctgtgt caaaataaga 4380
```

```
ttttgacaca gcctctactt                                                  4400

SEQ ID NO: 16          moltype = AA  length = 1315
FEATURE                Location/Qualifiers
source                 1..1315
                       mol_type = protein
                       organism = Clostridium tetani
SEQUENCE: 16
MPITINNFRY SDPVNNDTII MMEPPYCKGL DIYYKAFKIT DRIWIVPERY EFGTKPEDFN        60
PPSSLIEGAS EYYDPNYLRT DSDKDRFLQT MVKLFNRIKN NVAGEALLDK IINAIPYLGN       120
SYSLLDKFDT NSNSVSFNLL EQDPSGATTK SAMLTNLIIF GPGPVLNKNE VRGIVLRVDN       180
KNYFPCRDGF GSIMQMAFCP EYVPTFDNVI ENITSLTIGK SKYFQDPALL LMHELIHVLH       240
GLYGMQVSSH EIIPSKQEIY MQHTYPISAE ELFTFGGQDA NLISIDIKND LYEKTLNDYK       300
AIANKLSQVT SCNDPNIDID SYKQIYQQKY QFDKDSNGQY IVNEDKFQIL YNSIMYGFTE       360
IELGKKFNIK TRLSYFSMNH DPVKIPNLLD DTIYNDTEGF NIESKDLKSE YKGQNMRVNT       420
NAFRNVDGSG LVSKLIGLCK KIIPPTNIRE NLYNRTASLT DLGGELCIKI KNEDLTFIAE       480
KNSFSEEPFQ DEIVSYNTKN KPLNFNYSLD KIIVDYNLQS KITLPNDRTT PVTKGIPYAP       540
EYKSNAASTI EIHNIDDNTI YQYLYAQKSP TTLQRITMTN SVDDALINST KIYSYFPSVI       600
SKVNQGAQGI LFLQWVRDII DDFTNESSQK TTIDKISDVS TIVPYIGPAL NIVKQGYEGN       660
FIGALETTGV VLLLEYIPEI TLPVIAALSI AESSTQKEKI IKTIDNFLEK RYEKWIEVYK       720
LVKAKWLGTV NTQFQKRSYQ MYRSLEYQVD AIKKIIDYEY KIYSGPDKEQ IADEINNLKN       780
KLEEKANKAM ININIPMRES SRSFLVNQMI NEAKKQLEEF DTQSKNILMQ YIKANSKFIG       840
ITELKKLESK INKVFSTPIP FSYSKNLDCW VDNEEDIDVI LKKSTILNLD INNDIISDIS       900
GFNSSVITYP DAQLVPGING KAIHLVNNES SEVIVHKAMD IEYNDMFNNF TVSFWLRVPK       960
VSASHLEQYG TNEYSIISSM KKHSLSIGSG WSVSLKGNNL IWTLKDSAGE VRQITFRDLP      1020
DKFNAYLANK WVFITITNDR LSSANLYING VLMGSAEITG LGAIREDNNI TLKLDRCNNN      1080
NQYVSIDKFR IFCKALNPKE IEKLYTSYLS ITFLRDFWGN PLRYDTEYYL IPVASSSKDV      1140
QLKNITDYMY LTNAPSYTNG KLNIYYRRLY NGLKFIIKRY TPNNEIDSFV KSGDFIKLYV      1200
SYNNNEHIVG YPKDGNAFNN LDRILRVGYN APGIPLYKKM EAVKLRDLKT YSVQLKLYDD      1260
KNASLGLVGT HNGQIGNDPN RDILIASNWY FNHLKDKILG CDWYFVPTDE GWTND           1315

SEQ ID NO: 17          moltype = AA  length = 9
FEATURE                Location/Qualifiers
REGION                 1..9
                       note = peptide used for immunization
source                 1..9
                       mol_type = protein
                       organism = synthetic construct
SEQUENCE: 17
CTRIDEANQ                                                                9

SEQ ID NO: 18          moltype = AA  length = 114
FEATURE                Location/Qualifiers
source                 1..114
                       mol_type = protein
                       organism = Mus musculus
SEQUENCE: 18
EVNLVESGGD LVKPGGSLKL SCAVSGFTFS GYAMSWVRQT PEKRLEWVAS IATNGSTYYP        60
DTVKGRFTIF RDNARNILYL QMSSLRSEDT AIYYCTRLRG FDNWGQGTTL TVSS             114

SEQ ID NO: 19          moltype = AA  length = 112
FEATURE                Location/Qualifiers
source                 1..112
                       mol_type = protein
                       organism = Mus musculus
SEQUENCE: 19
DVLMTQIPLS LPVSLGDQAS ISCRSSQNIV HSNGNTYLEW YLQKSGQSPK LLIYKVFKRL        60
SGVPDRFSGS GSGTDFTLRI SRVEAEDLGV YYCFQGSHVP YTFGGGTKLE IK               112

SEQ ID NO: 20          moltype = AA  length = 10
FEATURE                Location/Qualifiers
source                 1..10
                       mol_type = protein
                       organism = Mus musculus
SEQUENCE: 20
GFTFSGYAMS                                                               10

SEQ ID NO: 21          moltype = AA  length = 16
FEATURE                Location/Qualifiers
source                 1..16
                       mol_type = protein
                       organism = Mus musculus
SEQUENCE: 21
SIATNGSTYY PDTVKG                                                        16

SEQ ID NO: 22          moltype = AA  length = 4
FEATURE                Location/Qualifiers
source                 1..4
                       mol_type = protein
```

```
                        organism = Mus musculus
SEQUENCE: 22
GFDN                                                                     4

SEQ ID NO: 23           moltype = AA  length = 16
FEATURE                 Location/Qualifiers
source                  1..16
                        mol_type = protein
                        organism = Mus musculus
SEQUENCE: 23
RSSQNIVHSN GNTYLE                                                        16

SEQ ID NO: 24           moltype = AA  length = 7
FEATURE                 Location/Qualifiers
source                  1..7
                        mol_type = protein
                        organism = Mus musculus
SEQUENCE: 24
KVFKRLS                                                                  7

SEQ ID NO: 25           moltype = AA  length = 9
FEATURE                 Location/Qualifiers
source                  1..9
                        mol_type = protein
                        organism = Mus musculus
SEQUENCE: 25
FQGSHVPYT                                                                9

SEQ ID NO: 26           moltype = AA  length = 119
FEATURE                 Location/Qualifiers
source                  1..119
                        mol_type = protein
                        organism = Mus musculus
SEQUENCE: 26
DVQLQESGPG LVKPSQSLSL TCTVTGFSIT SDYAWNWIRQ FPGNKLEWMG YISYKYGTRY         60
NPSLKGRISI TRDTSKNQFF LQLNSLTTED TAIYYCARRG TDGYGFAYWG QGTLVTVSA          119

SEQ ID NO: 27           moltype = AA  length = 111
FEATURE                 Location/Qualifiers
source                  1..111
                        mol_type = protein
                        organism = Mus musculus
SEQUENCE: 27
DIVLTQSPAS LGVSLGQRAT ISCRASESVS SSGYSYIHWY QQRPGQPPKL LIFLASNLES         60
GVPARFSGSG SGTDFTLNIH PVEEEDAATY YCQHSRELPL TFGAGTKLEL K                  111

SEQ ID NO: 28           moltype = AA  length = 11
FEATURE                 Location/Qualifiers
source                  1..11
                        mol_type = protein
                        organism = Mus musculus
SEQUENCE: 28
GFSITSDYAW N                                                             11

SEQ ID NO: 29           moltype = AA  length = 16
FEATURE                 Location/Qualifiers
source                  1..16
                        mol_type = protein
                        organism = Mus musculus
SEQUENCE: 29
YISYKYGTRY NPSLKG                                                        16

SEQ ID NO: 30           moltype = AA  length = 9
FEATURE                 Location/Qualifiers
source                  1..9
                        mol_type = protein
                        organism = Mus musculus
SEQUENCE: 30
GTDGYGFAY                                                                9

SEQ ID NO: 31           moltype = AA  length = 15
FEATURE                 Location/Qualifiers
source                  1..15
                        mol_type = protein
                        organism = Mus musculus
SEQUENCE: 31
RASESVSSSG YSYIH                                                         15

SEQ ID NO: 32           moltype = AA  length = 7
```

```
FEATURE                 Location/Qualifiers
source                  1..7
                        mol_type = protein
                        organism = Mus musculus
SEQUENCE: 32
LASNLES                                                                  7

SEQ ID NO: 33           moltype = AA  length = 9
FEATURE                 Location/Qualifiers
source                  1..9
                        mol_type = protein
                        organism = Mus musculus
SEQUENCE: 33
QHSRELPLT                                                                9

SEQ ID NO: 34           moltype = AA  length = 114
FEATURE                 Location/Qualifiers
source                  1..114
                        mol_type = protein
                        organism = Mus musculus
SEQUENCE: 34
EVKLVESGGD LVKPGGSLKL SCAVSGFSLN TYAMSWVRQT PEQRLEWVAS ISTNGSTYHS          60
DSVKGRFTIS RYNARNILYL QMSSLRSEDS AIYYCTRLRG FDYWGQGTTL TVSS              114

SEQ ID NO: 35           moltype = AA  length = 112
FEATURE                 Location/Qualifiers
source                  1..112
                        mol_type = protein
                        organism = Mus musculus
SEQUENCE: 35
DILMTQTPLS LSVSLGDQAS ISCRSSQNIV HSNGNTYLEW YLQKPGQSPK PLIYKLSKRF          60
SGVPDRFSGS GSGTYFTLKI SRVEAEDLGV YYCFQGSHVP YTFGGGTKLE IK                112

SEQ ID NO: 36           moltype = AA  length = 10
FEATURE                 Location/Qualifiers
source                  1..10
                        mol_type = protein
                        organism = Mus musculus
SEQUENCE: 36
GFSLNTYAMS                                                               10

SEQ ID NO: 37           moltype = AA  length = 16
FEATURE                 Location/Qualifiers
source                  1..16
                        mol_type = protein
                        organism = Mus musculus
SEQUENCE: 37
SISTNGSTYH SDSVKG                                                        16

SEQ ID NO: 38           moltype = AA  length = 8
FEATURE                 Location/Qualifiers
source                  1..8
                        mol_type = protein
                        organism = Mus musculus
SEQUENCE: 38
TRLRGFDY                                                                  8

SEQ ID NO: 39           moltype = AA  length = 16
FEATURE                 Location/Qualifiers
source                  1..16
                        mol_type = protein
                        organism = Mus musculus
SEQUENCE: 39
RSSQNIVHSN GNTYLE                                                        16

SEQ ID NO: 40           moltype = AA  length = 7
FEATURE                 Location/Qualifiers
source                  1..7
                        mol_type = protein
                        organism = Mus musculus
SEQUENCE: 40
KLSKRFS                                                                   7

SEQ ID NO: 41           moltype = AA  length = 9
FEATURE                 Location/Qualifiers
source                  1..9
                        mol_type = protein
                        organism = Mus musculus
SEQUENCE: 41
```

```
FQGSHVPYT                                                                    9

SEQ ID NO: 42           moltype = AA   length = 114
FEATURE                 Location/Qualifiers
source                  1..114
                        mol_type = protein
                        organism = Mus musculus
SEQUENCE: 42
EVKLVESGGD LVKPGGSLKL SCAASGFTFN TYAMSWVRQT PEKRLEWVAS ISSNGSTYHP     60
ESVKGRFTIS RDIARNILNL QMSSLRSEDT AIYYCSRLRG FDYWGQGTTL TVSS           114

SEQ ID NO: 43           moltype = AA   length = 112
FEATURE                 Location/Qualifiers
source                  1..112
                        mol_type = protein
                        organism = Mus musculus
SEQUENCE: 43
DVLMTQTPLS LPVSLGDQAS ISCRSSQSIV HSNGNTYLEW YLQKPGQSPK PLIYKVFKRF     60
SGVPDRFSGS GSGTDFTLKI SRVEAEDLGV YYCFQGSHVP YTFGGGTKLE IK             112

SEQ ID NO: 44           moltype = AA   length = 10
FEATURE                 Location/Qualifiers
source                  1..10
                        mol_type = protein
                        organism = Mus musculus
SEQUENCE: 44
GFTFNTYAMS                                                                   10

SEQ ID NO: 45           moltype = AA   length = 16
FEATURE                 Location/Qualifiers
source                  1..16
                        mol_type = protein
                        organism = Mus musculus
SEQUENCE: 45
SISSNGSTYH PESVKG                                                            16

SEQ ID NO: 46           moltype = AA   length = 8
FEATURE                 Location/Qualifiers
source                  1..8
                        mol_type = protein
                        organism = Mus musculus
SEQUENCE: 46
SRLRGFDY                                                                     8

SEQ ID NO: 47           moltype = AA   length = 16
FEATURE                 Location/Qualifiers
source                  1..16
                        mol_type = protein
                        organism = Mus musculus
SEQUENCE: 47
RSSQSIVHSN GNTYLE                                                            16

SEQ ID NO: 48           moltype = AA   length = 7
FEATURE                 Location/Qualifiers
source                  1..7
                        mol_type = protein
                        organism = Mus musculus
SEQUENCE: 48
KVFKRFS                                                                      7

SEQ ID NO: 49           moltype = AA   length = 9
FEATURE                 Location/Qualifiers
source                  1..9
                        mol_type = protein
                        organism = Mus musculus
SEQUENCE: 49
FQGSHVPYT                                                                    9

SEQ ID NO: 50           moltype = AA   length = 114
FEATURE                 Location/Qualifiers
source                  1..114
                        mol_type = protein
                        organism = Mus musculus
SEQUENCE: 50
EVKLVEFGGG LVEPRGSLKL SCAASGFTFS TYAMSWVRQT PEKRLEWVAS IASNGSTYYP     60
DSVRGRFTIS RDNARNILYL QMSSLRSEDT AMYYCSRLRG FDYWGQGSTL TVSS           114

SEQ ID NO: 51           moltype = AA   length = 112
FEATURE                 Location/Qualifiers
```

```
source                  1..112
                        mol_type = protein
                        organism = Mus musculus
SEQUENCE: 51
DVLMTQIPLS LPVSLGDQAS ISCRSSQSIV HSNGNTYLEW YLQKPGQSPS LLIYKVFKRL    60
SGVPDRFSGS GSGTEFTLKI NRVEAEDLGV YYCFQGSHVP YTFGGGTKLE IK           112

SEQ ID NO: 52           moltype = AA  length = 10
FEATURE                 Location/Qualifiers
source                  1..10
                        mol_type = protein
                        organism = Mus musculus
SEQUENCE: 52
GFTFSTYAMS                                                           10

SEQ ID NO: 53           moltype = AA  length = 16
FEATURE                 Location/Qualifiers
source                  1..16
                        mol_type = protein
                        organism = Mus musculus
SEQUENCE: 53
SIASNGSTYY PDSVRG                                                    16

SEQ ID NO: 54           moltype = AA  length = 8
FEATURE                 Location/Qualifiers
source                  1..8
                        mol_type = protein
                        organism = Mus musculus
SEQUENCE: 54
SRLRGFDY                                                              8

SEQ ID NO: 55           moltype = AA  length = 16
FEATURE                 Location/Qualifiers
source                  1..16
                        mol_type = protein
                        organism = Mus musculus
SEQUENCE: 55
RSSQSIVHSN GNTYLE                                                    16

SEQ ID NO: 56           moltype = AA  length = 7
FEATURE                 Location/Qualifiers
source                  1..7
                        mol_type = protein
                        organism = Mus musculus
SEQUENCE: 56
KVFKRLS                                                               7

SEQ ID NO: 57           moltype = AA  length = 9
FEATURE                 Location/Qualifiers
source                  1..9
                        mol_type = protein
                        organism = Mus musculus
SEQUENCE: 57
FQGSHVPYT                                                             9

SEQ ID NO: 58           moltype = AA  length = 114
FEATURE                 Location/Qualifiers
source                  1..114
                        mol_type = protein
                        organism = Mus musculus
SEQUENCE: 58
EVKLVESGGG LVKPGGSLKL SCAASGFTFR SYAVSWVRQT PEKRLEWVAS ISTNGSTYYP    60
DSMKGRFTIS RDTARNILYL EMNSLRSEDT AMYYCARLRG FDYWGQGTPL TVSS         114

SEQ ID NO: 59           moltype = AA  length = 112
FEATURE                 Location/Qualifiers
source                  1..112
                        mol_type = protein
                        organism = Mus musculus
SEQUENCE: 59
DVLMTQTPLS LPVSLGDQAS ISCRSSQSIV HSNGNTYLEW YLQKPGQSPK LLIYKVSKRF    60
SGVPDRFSGS GSGTDFTLKI TRVEAEDLGV YYCFQGSHVP YTFGGGTKLE IK           112

SEQ ID NO: 60           moltype = AA  length = 10
FEATURE                 Location/Qualifiers
source                  1..10
                        mol_type = protein
                        organism = Mus musculus
SEQUENCE: 60
```

```
-continued

GFTFRSYAVS                                                            10

SEQ ID NO: 61        moltype = AA  length = 16
FEATURE              Location/Qualifiers
source               1..16
                     mol_type = protein
                     organism = Mus musculus
SEQUENCE: 61
SISTNGSTYY PDSMKG                                                     16

SEQ ID NO: 62        moltype = AA  length = 7
FEATURE              Location/Qualifiers
source               1..7
                     mol_type = protein
                     organism = Mus musculus
SEQUENCE: 62
RLRGFDY                                                                7

SEQ ID NO: 63        moltype = AA  length = 16
FEATURE              Location/Qualifiers
source               1..16
                     mol_type = protein
                     organism = Mus musculus
SEQUENCE: 63
RSSQSIVHSN GNTYLE                                                     16

SEQ ID NO: 64        moltype = AA  length = 7
FEATURE              Location/Qualifiers
source               1..7
                     mol_type = protein
                     organism = Mus musculus
SEQUENCE: 64
KVSKRFS                                                                7

SEQ ID NO: 65        moltype = AA  length = 9
FEATURE              Location/Qualifiers
source               1..9
                     mol_type = protein
                     organism = Mus musculus
SEQUENCE: 65
FQGSHVPYT                                                              9

SEQ ID NO: 66        moltype = AA  length = 114
FEATURE              Location/Qualifiers
source               1..114
                     mol_type = protein
                     organism = Mus musculus
SEQUENCE: 66
EVKLVESGGD LVKPGGSLKL SCAASGFTLS DYAMSWVRQS PEERLEWVAS ISTNGSTYYP      60
DSVKGRFTIS RDNARNILSL QMSSLRSEDT AIYYCTRLRG FDNWGQGTLL TVSS           114

SEQ ID NO: 67        moltype = AA  length = 112
FEATURE              Location/Qualifiers
source               1..112
                     mol_type = protein
                     organism = Mus musculus
SEQUENCE: 67
DVLMTQTPLS LPVSLGDQAS ISCRSSQNIV HSNGNTYLEW YLQKSGQSPK LLMYKVSKRL      60
SGVPDRFSGR GSGTDFTLKI SRVEAEDLGV YYCFQGSHVP YTFGGGTKLE IK             112

SEQ ID NO: 68        moltype = AA  length = 10
FEATURE              Location/Qualifiers
source               1..10
                     mol_type = protein
                     organism = Mus musculus
SEQUENCE: 68
GFTLSDYAMS                                                            10

SEQ ID NO: 69        moltype = AA  length = 16
FEATURE              Location/Qualifiers
source               1..16
                     mol_type = protein
                     organism = Mus musculus
SEQUENCE: 69
SISTNGSTYY PDSVKG                                                     16

SEQ ID NO: 70        moltype = AA  length = 8
FEATURE              Location/Qualifiers
source               1..8
```

```
                        mol_type = protein
                        organism = Mus musculus
SEQUENCE: 70
TRLRGFDN                                                                        8

SEQ ID NO: 71           moltype = AA  length = 16
FEATURE                 Location/Qualifiers
source                  1..16
                        mol_type = protein
                        organism = Mus musculus
SEQUENCE: 71
RSSQNIVHSN GNTYLE                                                              16

SEQ ID NO: 72           moltype = AA  length = 7
FEATURE                 Location/Qualifiers
source                  1..7
                        mol_type = protein
                        organism = Mus musculus
SEQUENCE: 72
KVSKRLS                                                                         7

SEQ ID NO: 73           moltype = AA  length = 9
FEATURE                 Location/Qualifiers
source                  1..9
                        mol_type = protein
                        organism = Mus musculus
SEQUENCE: 73
FQGSHVPYT                                                                       9

SEQ ID NO: 74           moltype = AA  length = 8
FEATURE                 Location/Qualifiers
source                  1..8
                        mol_type = protein
                        organism = Mus musculus
SEQUENCE: 74
TRIDEANQ                                                                        8

SEQ ID NO: 75           moltype = AA  length = 7
FEATURE                 Location/Qualifiers
source                  1..7
                        mol_type = protein
                        organism = Mus musculus
SEQUENCE: 75
RIDEANQ                                                                         7

SEQ ID NO: 76           moltype = AA  length = 6
FEATURE                 Location/Qualifiers
source                  1..6
                        mol_type = protein
                        organism = Mus musculus
SEQUENCE: 76
IDEANQ                                                                          6

SEQ ID NO: 77           moltype = AA  length = 5
FEATURE                 Location/Qualifiers
source                  1..5
                        mol_type = protein
                        organism = Mus musculus
SEQUENCE: 77
DEANQ                                                                           5
```

The invention claimed is:

1. A kit for directly determining the biological activity of a *Clostridium botulinum* toxin serotype A (BoNT/A) Neurotoxin polypeptide in cells, comprising
   i) a first isolated capture antibody which specifically binds to a non-cleaved BoNT/A Neurotoxin substrate SNAP-25 and a BoNT/A Neurotoxin-cleaved substrate SNAP-25;
   ii) a second isolated capture antibody which specifically binds to the cleavage site of the BoNT/A Neurotoxin-cleaved substrate SNAP-25 and does not bind non-cleaved BoNT/A Neurotoxin substrate SNAP-25, under conditions which allow for binding of the first and second isolated capture antibodies to the substrates, and wherein the second isolated capture antibody is a mouse monoclonal antibody clone 20-2-5 comprising a complementarity determining region (CDR) heavy chain variable region 1 having the sequence of SEQ ID NO:20; a CDR heavy chain variable region 2 having the sequence of SEQ ID NO:21; a CDR heavy chain variable region 3 having the sequence of SEQ ID NO:22; a CDR light chain variable region 1 having the sequence of SEQ ID NO:23; a CDR light chain variable region 2 having the sequence of SEQ ID NO:24; and a CDR light chain variable region 3 having the sequence of SEQ ID NO: 25;
   iii) a first isolated detection antibody which specifically binds to the first isolated capture antibody under conditions which allow for binding of the first isolated detection antibody to the first isolated capture antibody, thus capable of forming first detection complexes; and iv) a second isolated detection antibody which specifically binds to the second isolated capture antibody under conditions which allow for binding of the second isolated detection antibody to the second isolated capture antibody, thus capable of forming second detection complexes; and v) instructions for directly determining the biological activity of the BoNT/A Neurotoxin polypeptide in cells based on the amount of SNAP-25 substrate cleaved by the BoNT/A Neurotoxin polypeptide as determined based on the amounts of the first and second detection complexes.

2. The kit of claim 1, wherein the cells susceptible to BoNT/A Neurotoxin intoxication are neuronal cells or neuronal differentiated cells selected from the group consisting of primary neuronal cells, tumor cells which are capable of differentiating to neuronal cells, neuroblastoma cells, P19 cells and induced pluripotent stem (IPS) cell-derived neurons.

3. The kit of claim 1, wherein the first isolated capture antibody which specifically binds to the non-cleaved BoNT/A Neurotoxin substrate SNAP-25 and the BoNT/A Neurotoxin-cleaved substrate SNAP-25 is a rabbit polyclonal anti-SNAP-25 antibody S9684, a rabbit polyclonal anit-SNAP25 antibody PA5-19708, or a rabbit polyclonal anti-SNAP25 antibody PA5-19701.

4. The kit of claim 1, further comprising a mouse monoclonal antibody MC-6053.

5. The kit of claim 1, wherein the first and/or second isolated capture antibody is immobilized to a solid phase support.

6. The kit of claim 1, wherein the first isolated detection antibody is an alkaline phosphatase (AP)-conjugated antibody, a horseradish-peroxidase (HRP)-conjugated antibody or an antibody conjugated to a fluorescent dye.

7. The kit of claim 6, wherein a substrate for the HRP-conjugated antibody is selected from the group consisting of a fluorogenic substrate for horseradish-peroxidase, 10-Acetyl-3,7-Dihydroxyphenoxazine (ADHP) and 3-(4-Hydroxyphenyl) propionic acid (HPPA).

8. The kit of claim 6, wherein a substrate for the AP-conjugated antibody is selected from the group consisting of 4-methylumbelliferryl phosphate derivative selected from 6,8-Difluoro-4-methylumbelliferyl phosphate (DiFMUP) and fluorescein diphosphate (FDP).

9. The kit of claim 1, wherein the second isolated detection antibody is an alkaline phosphatase (AP)-conjugated antibody, a horseradish-peroxidase (HRP)-conjugated antibody, a glucose oxidase-conjugated antibody, a tyrosinase-conjugated antibody or a β-Galactosidase-conjugated antibody.

10. The kit of claim 9, wherein a substrate for the HRP-conjugated antibody is selected from the group consisting of a fluorogenic substrate for horseradish-peroxidase, 10-Acetyl-3,7-Dihydroxyphenoxazine (ADHP) and 3-(4-Hydroxyphenyl) propionic acid (HPPA).

11. The kit of claim 9, wherein a substrate for the AP-conjugated antibody is selected from the group consisting of 4-methylumbelliferryl phosphate derivative selected from 6,8-Difluoro-4-methylumbelliferyl phosphate (DiFMUP) and fluorescein diphosphate (FDP).

* * * * *